(12) United States Patent
Kosak

(10) Patent No.: US 11,344,069 B2
(45) Date of Patent: *May 31, 2022

(54) PUMPING/NURSING GARMENT

(71) Applicant: Simple Wishes LLC, Dallas, TX (US)

(72) Inventor: Joy Kosak, Moraga, CA (US)

(73) Assignee: Simple Wishes LLC, Dallas, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/551,295

(22) Filed: Aug. 26, 2019

(65) Prior Publication Data

US 2020/0154793 A1 May 21, 2020

Related U.S. Application Data

(63) Continuation of application No. 16/201,718, filed on Nov. 27, 2018, now Pat. No. 10,420,378, which is a (Continued)

(51) Int. Cl.
*A41C 3/04* (2006.01)
*A61M 1/06* (2006.01)
*A41F 1/00* (2006.01)

(52) U.S. Cl.
CPC ............... *A41C 3/04* (2013.01); *A41F 1/006* (2013.01); *A61M 1/062* (2014.02); *A61M 2209/088* (2013.01)

(58) Field of Classification Search
CPC ....... A41C 3/04; A41C 3/0007; A41C 3/0028; A41C 3/0035; A41C 3/12
(Continued)

(56) References Cited

U.S. PATENT DOCUMENTS

| 623,413 A | 4/1899 | Murray |
| 949,414 A | 2/1910 | Cunningham |

(Continued)

FOREIGN PATENT DOCUMENTS

| AU | 2011100651 A4 | 7/2011 |
| AU | 2013203882 † | 10/2014 |

(Continued)

OTHER PUBLICATIONS

Office Action for U.S. Appl. No. 12/453,073, dated Sep. 23, 2011, 11 pages.

(Continued)

*Primary Examiner* — Gloria M Hale
(74) *Attorney, Agent, or Firm* — Cooley LLP

(57) ABSTRACT

Apparatus are described herein for providing a garment (e.g. a bra) that can be used by a wearer during extraction of breast milk using a breast pump. In some embodiments, a garment can include an inner panel that defines one or more openings and an outer panel that can cover the openings. Each of the openings can receive a portion of a breast pump, and the inner panel can provide support to the breast pump during milk extraction. The outer panel can be removably coupled to the inner panel with a clasp such that the outer panel can be at least partially removed from the inner panel to gain access to the opening(s). In some embodiments, the inner panel can be removably coupled to another portion of the garment such that the inner panel can be partially removed and/or fully removed from the remaining portions of the garment.

20 Claims, 62 Drawing Sheets

Related U.S. Application Data continuation of application No. 15/873,456, filed on Jan. 17, 2018, now Pat. No. 10,426,203.

(60) Provisional application No. 62/548,706, filed on Aug. 22, 2017, provisional application No. 62/448,622, filed on Jan. 20, 2017.

(58) Field of Classification Search
USPC .......................................................... 450/36
See application file for complete search history.

(56) References Cited

U.S. PATENT DOCUMENTS

| | | | |
|---|---|---|---|
| 2,305,051 A | 11/1940 | Witkower | |
| 2,436,430 A | 2/1948 | Hart | |
| 2,492,862 A | 12/1949 | Harvey | |
| 2,522,010 A | 9/1950 | Woodruff | |
| 2,585,338 A | 2/1952 | Meares | |
| 2,613,355 A | 10/1952 | Coleman | |
| 2,679,048 A | 5/1954 | Alberts | |
| 2,738,509 A | 3/1956 | Bauder | |
| 3,002,515 A | 10/1961 | Glogover | |
| 4,335,728 A | 6/1982 | Fildan | |
| 4,640,287 A | 2/1987 | Anderson et al. | |
| 4,648,404 A | 3/1987 | Clark | |
| 4,878,879 A | 11/1989 | Kunstadter | |
| 4,911,677 A | 3/1990 | White | |
| 5,098,330 A | 3/1992 | Greenberg | |
| 5,334,082 A | 8/1994 | Barker | |
| 5,341,514 A | 8/1994 | Dale | |
| 5,380,238 A | 1/1995 | Crew-Gee | |
| 5,395,280 A | 3/1995 | Greenberg | |
| 5,514,166 A | 5/1996 | Silver et al. | |
| 5,575,768 A | 11/1996 | Lockridge et al. | |
| 5,616,125 A | 4/1997 | Jelks | |
| 5,624,296 A * | 4/1997 | Weber-Unger | A41C 3/04 2/101 |
| 5,690,537 A | 11/1997 | Kalmus | |
| 6,004,186 A | 12/1999 | Penny | |
| 6,027,396 A | 2/2000 | Yonchar | |
| 6,086,451 A | 7/2000 | Fernandes | |
| 6,227,936 B1 | 5/2001 | Mendoza | |
| 6,247,996 B1 | 6/2001 | Fields | |
| 6,319,092 B1 | 11/2001 | Leyhe et al. | |
| 6,438,758 B1 | 8/2002 | Burkard et al. | |
| 6,440,100 B1 | 8/2002 | Prentiss | |
| 6,705,920 B1 | 3/2004 | Engel | |
| 6,854,132 B1 | 2/2005 | Polzin | |
| 6,866,558 B2 | 3/2005 | Luciano et al. | |
| 6,887,217 B1 | 5/2005 | Logan | |
| 6,974,361 B2 | 12/2005 | Cravaack et al. | |
| 7,232,359 B1 | 6/2007 | Richardson | |
| 7,306,505 B2 | 12/2007 | Barbour et al. | |
| 7,507,141 B2 | 3/2009 | Ward et al. | |
| 7,591,706 B2 | 9/2009 | Barbour et al. | |
| 8,192,247 B2 † | 6/2012 | Abbaszadeh | |
| 8,323,070 B2 | 12/2012 | Abbaszadeh | |
| 8,523,629 B2 | 9/2013 | Pundyk | |
| 9,167,855 B2 | 10/2015 | Abbaszadeh | |
| 9,498,005 B2 | 11/2016 | Abbaszadeh | |
| 9,872,524 B2 | 1/2018 | Abbaszadeh | |
| 9,894,942 B2 | 2/2018 | Burrell | |
| 10,212,972 B2 | 2/2019 | Abbaszadeh | |
| 10,420,377 B2 * | 9/2019 | Abbaszadeh | A61M 1/062 |
| 10,420,378 B2 * | 9/2019 | Kosak | A41C 3/04 |
| 10,426,203 B2 * | 10/2019 | Kosak | A41C 3/04 |
| 10,772,361 B2 | 9/2020 | Abbaszadeh | |
| 10,905,173 B1 | 2/2021 | Kosak et al. | |
| 2002/0062512 A1 | 5/2002 | Gustafson et al. | |
| 2003/0027491 A1 | 2/2003 | Cravaack et al. | |
| 2003/0167037 A1 | 9/2003 | Fialkoff | |
| 2003/0191433 A1 | 10/2003 | Prentiss | |
| 2003/0232573 A1 | 12/2003 | Plew | |
| 2004/0016039 A1 | 1/2004 | Caprio | |
| 2006/0025039 A1 | 2/2006 | Barbour et al. | |
| 2006/0211336 A1 | 9/2006 | Brigham | |
| 2007/0161330 A1 | 7/2007 | Whitehead et al. | |
| 2008/0022434 A1 | 1/2008 | Adelman | |
| 2008/0039781 A1 | 2/2008 | Bjorge | |
| 2008/0146118 A1 | 6/2008 | Solberg et al. | |
| 2008/0262420 A1 | 10/2008 | Dao et al. | |
| 2009/0286452 A1 | 11/2009 | Grayson | |
| 2010/0031418 A1 | 2/2010 | Op't Hof | |
| 2010/0068971 A1 * | 3/2010 | Hendrickson | A41C 3/04 450/31 |
| 2010/0159801 A1 | 6/2010 | Abbaszadeh | |
| 2010/0159802 A1 | 6/2010 | Abbaszadeh | |
| 2010/0261410 A1 * | 10/2010 | Hirtz | A41C 3/04 450/36 |
| 2011/0081826 A1 * | 4/2011 | Hendrickson | A41C 3/0028 450/36 |
| 2011/0092134 A1 | 4/2011 | Alva | |
| 2011/0237156 A1 | 9/2011 | Boonen et al. | |
| 2011/0314587 A1 * | 12/2011 | Ritchie | A41C 3/04 2/104 |
| 2012/0129427 A1 * | 5/2012 | Perez | A41C 3/04 450/36 |
| 2012/0184179 A1 | 7/2012 | Blitz | |
| 2013/0095727 A1 | 4/2013 | Abbaszadeh | |
| 2014/0087625 A1 | 3/2014 | Ironi | |
| 2014/0220460 A1 | 8/2014 | Alva | |
| 2014/0273737 A1 | 9/2014 | Cortese et al. | |
| 2014/0364035 A1 * | 12/2014 | Abbaszadeh | A41C 3/04 450/36 |
| 2014/0364036 A1 * | 12/2014 | Abbaszadeh | A61M 1/06 450/36 |
| 2016/0015092 A1 | 1/2016 | Abbaszadeh | |
| 2016/0095967 A1 | 4/2016 | Weston | |
| 2016/0150834 A1 | 6/2016 | Boele et al. | |
| 2017/0172502 A1 * | 6/2017 | Rofe | G01L 1/2256 |
| 2017/0265530 A1 | 9/2017 | Donlon et al. | |
| 2017/0280786 A1 | 10/2017 | Abbaszadeh | |
| 2017/0280787 A1 | 10/2017 | Burrell | |
| 2018/0064177 A1 | 3/2018 | Akerson et al. | |
| 2018/0064178 A1 * | 3/2018 | Akerson | A61B 5/4288 |
| 2018/0132542 A1 * | 5/2018 | Abbaszadeh | A41C 3/144 |
| 2018/0206559 A1 * | 7/2018 | Kosak | A41F 1/006 |
| 2018/0255840 A1 | 9/2018 | Abbaszadeh | |
| 2018/0352884 A1 * | 12/2018 | Vanos | A41C 3/0028 |
| 2019/0014829 A1 * | 1/2019 | Kim | A41C 3/0007 |
| 2019/0142078 A1 | 5/2019 | Kosak | |
| 2019/0208839 A1 * | 7/2019 | Amos | A41D 1/215 |
| 2019/0261698 A1 * | 8/2019 | Akerson | A41C 3/005 |
| 2019/0289926 A1 | 9/2019 | Abbaszadeh | |
| 2020/0154792 A1 | 5/2020 | Abbaszadeh | |

FOREIGN PATENT DOCUMENTS

| | | |
|---|---|---|
| CN | 104223390 A | 12/2014 |
| CN | 204907978 U | 12/2015 |
| EP | 2810573 | 8/2016 |
| ER | 881406 A | 4/1943 |
| FR | 919893 A | 3/1947 |
| GB | 2536541 † | 9/2016 |
| GB | 2536541 A | 9/2016 |
| GN | 201479956 U | 5/2010 |
| KR | 2011-0001216 | 2/2011 |
| KR | 20110001216 † | 2/2011 |
| WO | WO 2007/053073 | 5/2007 |
| WO | WO 2008/005713 | 1/2008 |
| WO | WO 2010/080122 | 7/2010 |
| WO | WO 2011/135092 | 11/2011 |

OTHER PUBLICATIONS

International Search Report and Written Opinion for International Application No. PCT/US2009/006618, dated Mar. 8, 2010, 9 pages.
Office Action for U.S. Appl. No. 12/585,829, dated Aug. 24, 2011, 10 pages.
Office Action for U.S. Appl. No. 13/692,204, dated Oct. 1, 2014, 9 pages.

(56) References Cited

OTHER PUBLICATIONS

Office Action for U.S. Appl. No. 13/692,204, dated Jul. 3, 2013, 6 pages.
Office Action for U.S. Appl. No. 13/692,204, dated Apr. 8, 2014, 6 pages.
Office Action for U.S. Appl. No. 14/867,979, dated Nov. 5, 2015, 8 pages.
Office Action for U.S. Appl. No. 14/867,979, dated Apr. 4, 2016, 6 pages.
Office Action for U.S. Appl. No. 15/357,596, dated Dec. 31, 2018, 12 pages.
Extended European Search Report for European Application No. 14171552.4, dated Sep. 9, 2014, 6 pages.
Office Action for European Application No. 14171552.4, dated Dec. 3, 2015, 4 pages.
Office Action for U.S. Appl. No. 14/172,812, dated Jun. 16, 2016, 7 pages.
First Office Action for Chinese Application No. 201410077245.4, dated Dec. 7, 2016, 31 pages.
Second Office Action for Chinese Application No. 201410077245.4, dated Oct. 30, 2017, 29 pages.
Third Office Action for Chinese Application No. 201410077245.4, dated Jul. 9, 2018, 34 pages.
Fourth Office Action for Chinese Application No. 201410077245.4, dated Mar. 21, 2019, 27 pages.
Extended European Search Report for European Application No. 14171556.5, dated Sep. 10, 2014, 5 pages.
Office Action for U.S. Appl. No. 14/172,826, dated May 20, 2016, 8 pages.
Office Action for U.S. Appl. No. 14/172,826, dated Dec. 29, 2016, 5 pages.
Office Action for U.S. Appl. No. 14/172,826, dated Apr. 10, 2017, 15 pages.
Extended European Search Report for European Application No. 16179769.1, dated Feb. 10, 2017, 8 pages.
Office Action for U.S. Appl. No. 15/873,317, dated Jun. 29, 2018, 9 pages.
International Search Report and Written Opinion for International Application No. PCT/US2016/043326, dated Nov. 28, 2016, 19 pages.
Office Action for U.S. Appl. No. 15/873,456, dated Mar. 21, 2019, 14 pages.
International Search Report and Written Opinion for International Application No. PCT/US2018/014245, dated Jun. 12, 2018, 15 pages.
Office Action for U.S. Appl. No. 16/201,718, dated Mar. 21, 2019, 11 pages.
Nursing Bra Express, "Pump Up the Band Hands Free Nursing Bra," [online], [Retrieved on Mar. 2, 2013], [Retrieved from the Internet: URL: <http://www.nursingbraexpress.com/nursing-bras/pump-band-hands-free-nursing-bra>.
Decision on Rejection for Chinese Application No. 201410077245.4, dated Aug. 5, 2019, 26 pages.
Office Action for U.S. Appl. No. 15/872,360, dated Dec. 30, 2019, 14 pages.
Office Action for U.S. Appl. No. 16/550,902, dated Sep. 17, 2020, 12 pages.
First Office Action for Chinese Application No. 201880007431.7, dated Jul. 3, 2020, 29 pages.
Office Action for European Application No. 18713053.9, dated Oct. 26, 2020, 4 pages.
Screen captures from YouTube video clip entitled "EverBeautyBra™ by LactaMed™," uploaded Apr. 23, 2018 by user "LactaMed Inc". Retrieved from the Internet: <URL: https://www.youtube.com/watch?v=-KUuqkxejIM>, 2 pages.
LactaMed, "EverBeautyBra™ Hands Free Pumping and Nursing Bra in One," 2020, [Online], Retrieved from the Internet: URL: <https://lactamed.com/products/everbeautybra-all-in-one?_pos=5&_sid=3f52c4eee&_ss=r>, 8 pages.
Melissa Holland, BeliBea Bra Instagram Post, dated Oct. 19, 2016, at https://www.instagram.com/p/BLwbn4UhvsE/ retrieved on Aug. 20, 2020.†
Melissa Holland, AbcKidsExpo2016, dated Oct. 18, 2016, at https://www.instagram.com/p/BLtigR3hRt6/ retrieved on Aug. 20, 2020.†

\* cited by examiner
† cited by third party

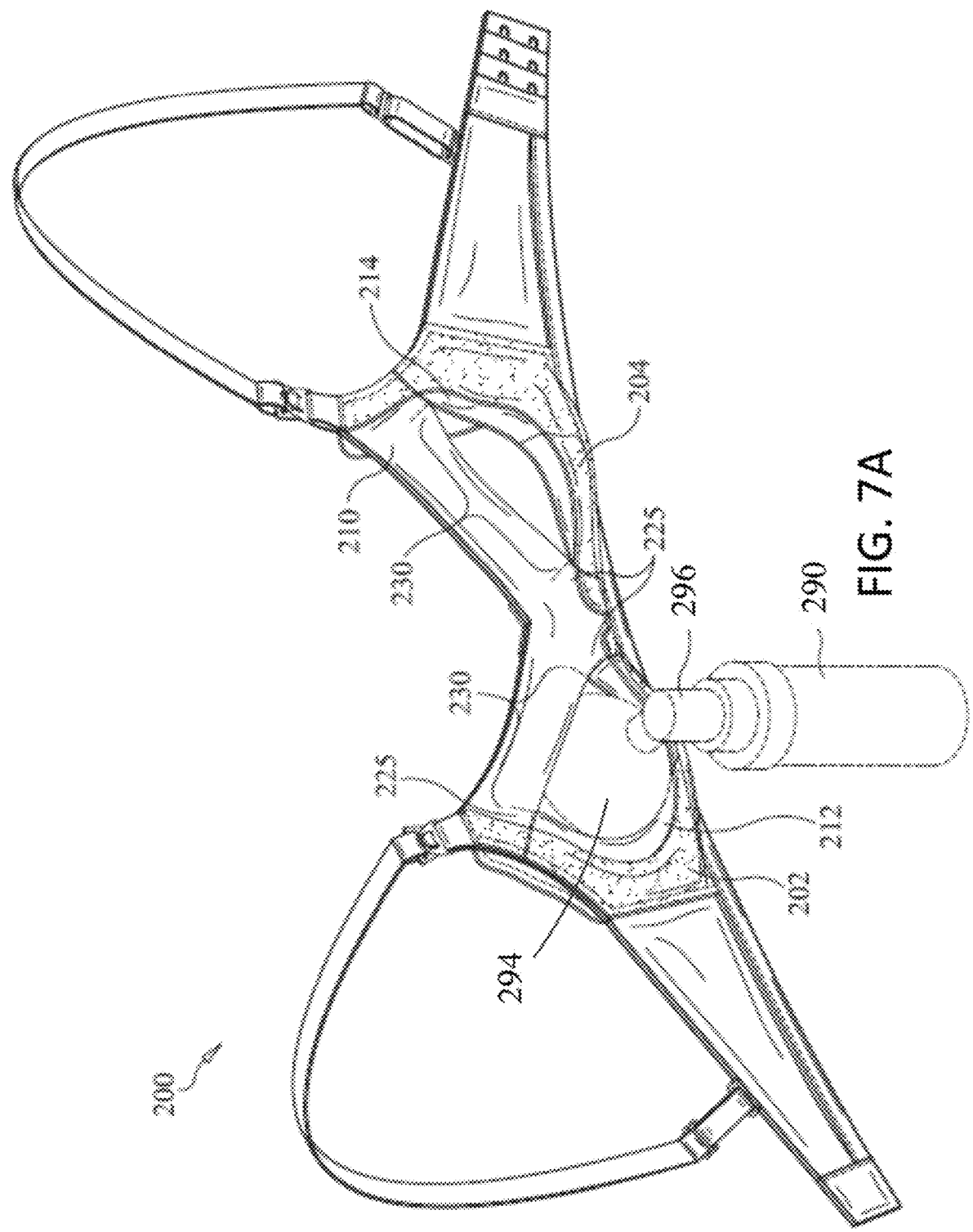

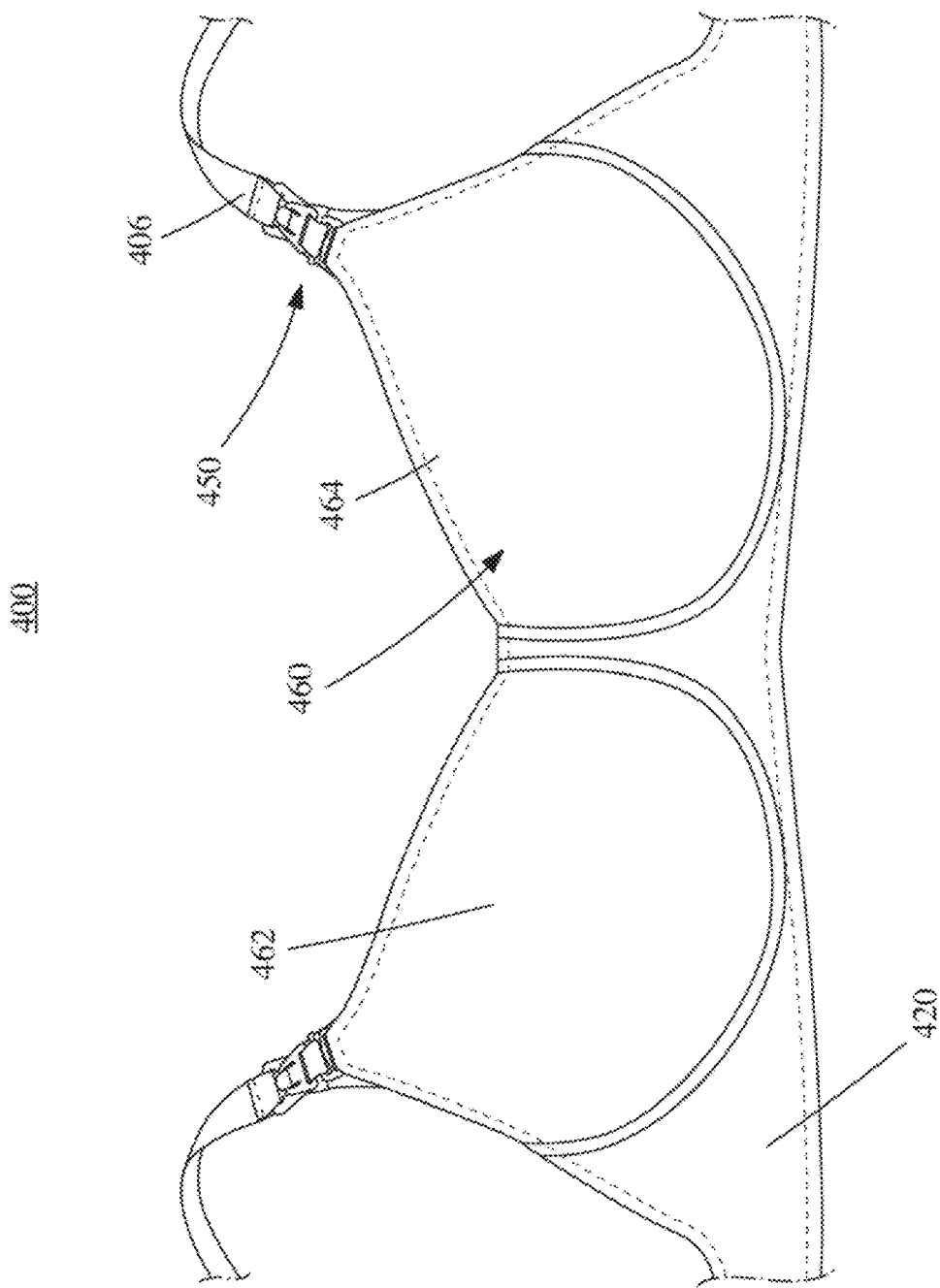

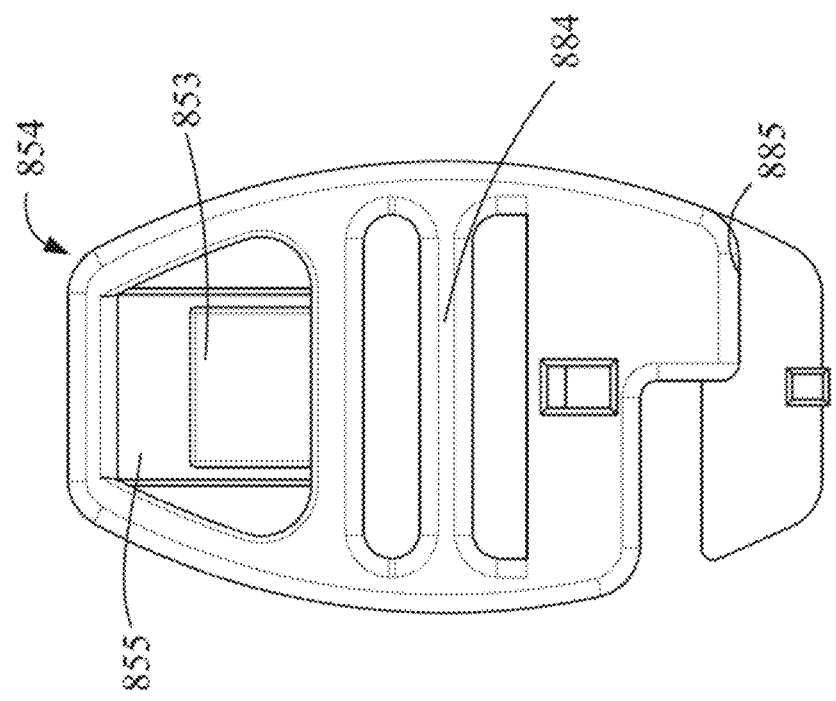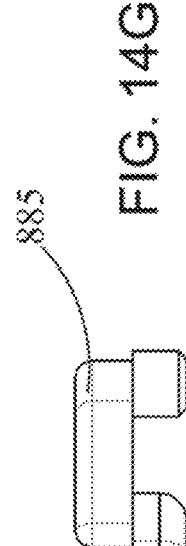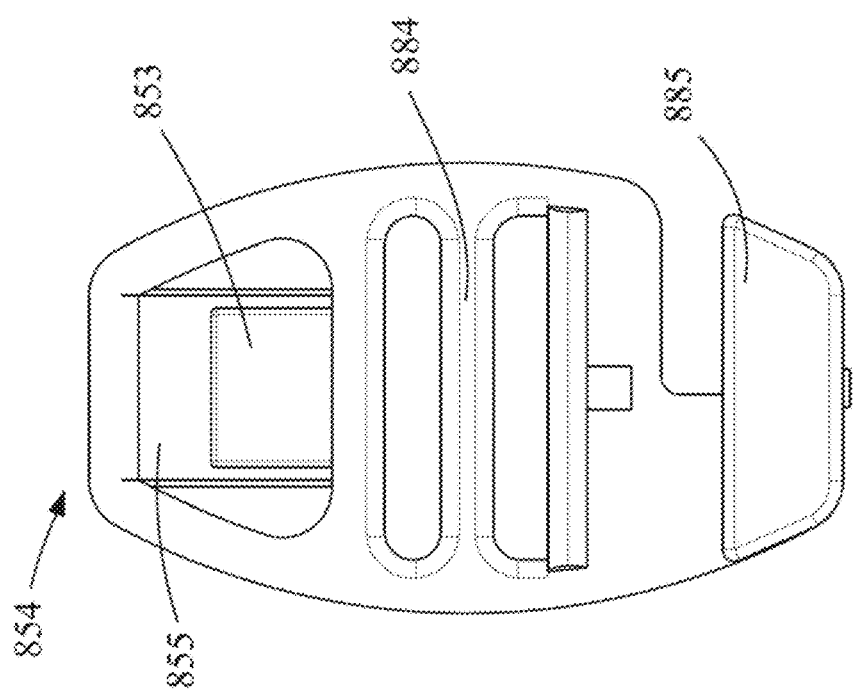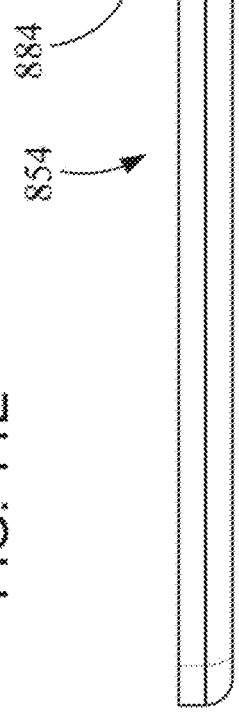

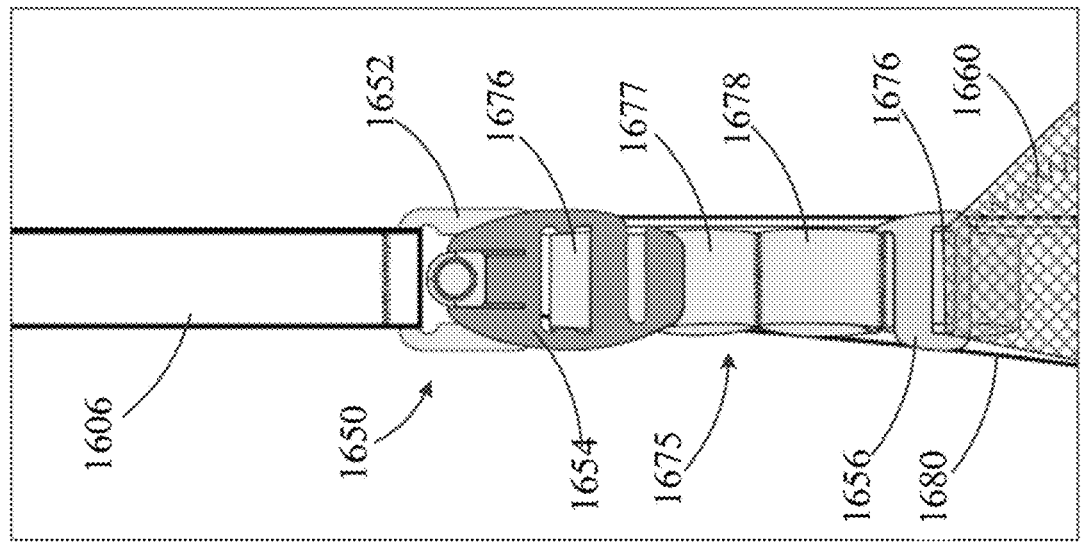
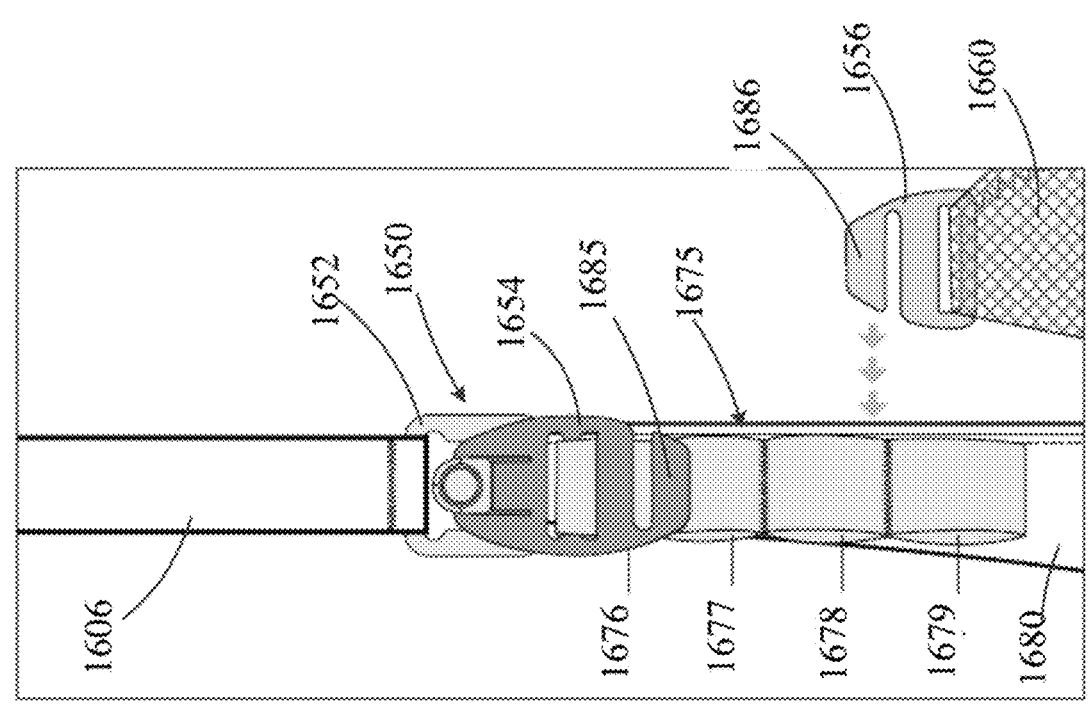
FIG. 39B
FIG. 39A

PUMPING/NURSING GARMENT

CROSS-REFERENCE TO RELATED APPLICATIONS

This application is a continuation of U.S. patent application Ser. No. 16/201,718 filed Nov. 27, 2018, now U.S. Pat. No. 10,420,378, which is a continuation of U.S. patent application Ser. No. 15/873,456, filed Jan. 17, 2018, now U.S. Pat. No. 10,426,203, which claims priority to U.S. Provisional Patent Application No. 62/448,622, filed Jan. 20, 2017 and U.S. Provisional Patent Application No. 62/548,706, filed Aug. 22, 2017, each of the disclosures of which is incorporated by reference in its entirety.

This application is related to U.S. patent application Ser. No. 15/872,360, filed Jan. 16, 2018, which is a continuation of International Application No. PCT/US16/43326, filed Jul. 21, 2016, which claims priority to U.S. Provisional Application No. 62/196,080, filed Jul. 23, 2015; and is related to U.S. patent application Ser. No. 16/283,165, filed Feb. 22, 2019, which is a continuation of U.S. patent application Ser. No. 15/873,317, now U.S. Pat. No. 10,212,972, filed Jan. 17, 2018, which is a continuation of U.S. patent application Ser. No. 14/172,826, now U.S. Pat. No. 9,872,524, entitled "Pumping/Nursing Bra," filed Feb. 4, 2014, which claims priority to U.S. patent application Ser. No. 14/172,812, entitled "Pumping/Nursing Bra," filed Feb. 4, 2014 (now abandoned), which claims priority to U.S. Provisional Application No. 61/832,592, filed on Jun. 7, 2013, each of the disclosures of which is hereby incorporated by reference in its entirety. This application is also related to U.S. patent application Ser. No. 16/550,902, filed Aug. 26, 2019, which is a continuation of U.S. patent application Ser. No. 15/357,596, filed Nov. 21, 2016, now U.S. Pat. No. 10,420,377, which is a continuation of U.S. patent application Ser. No. 14/867,979, filed Sep. 29, 2015, now U.S. Pat. No. 9,498,005 which is a continuation of U.S. patent application Ser. No. 13/692,204, filed Dec. 3, 2012, now U.S. Pat. No. 9,167,855, which is a continuation of U.S. patent application Ser. No. 12/585,829, filed Sep. 25, 2009, now U.S. Pat. No. 8,323,070, which claims priority to U.S. Provisional Application No. 61/193,731, filed Dec. 19, 2008.

This application is also related to U.S. Provisional Application No. 62/879,135, filed Jul. 26, 2019, entitled "Pumping/Nursing Garment," the disclosure of which is hereby incorporated by reference in its entirety.

BACKGROUND

Embodiments described herein relate to a bra that can provide support to a breast pumping device while the wearer of the bra is pumping breast milk using the breast pumping device.

A breast pump may be used to express milk from a breast. Implementations of breast pumps have a pump body to express the milk and a milk container to receive the milk. The pump body of a breast pump may have a breast shield or a flange having a funnel shape with a cup portion that fits over at least a portion of a breast.

A let-down cushion or let-down massage cushion of a breast pump may fit between a breast shield or a flange of a pump body of the breast pump and a breast. The let-down cushion may fit within the breast shield or flange and have an edge that folds over an edge of the breast shield or the flange of the pump body. The let-down cushion may flex in and out to massage the areola of a breast to help stimulate milk flow. A seal may be formed between the let-down cushion and a breast to create suction and encourage breast milk expression.

To use a breast pump, a user manually holds the breast flange, shield, or pump body over a breast. While using the breast pump, the wearer is not able to use their hands for other tasks. It may be desirable to express milk from both breasts simultaneously, but doing so, requires the user to hold both breast pump bodies against oneself and is both awkward, and does not allow the user to do other tasks. As such, garments that assist in supporting the breast pump body for milk expression are needed to allow a wearer to use their hands for other tasks during milk expression with a breast pump.

SUMMARY

Apparatus are described herein for providing a garment (e.g. a bra) that can be used by a wearer during extraction of breast milk using a breast pump, and/or during breast feeding. In some embodiments, a garment can include an inner panel and an outer panel. The inner panel can include a first portion to cover a first breast of a wearer that defines an opening and a second portion to cover a second breast of the wearer that defines a second opening. Each of the openings can be used to gain access to the breast to, for example, insert a portion of a breast pump and dispose the portion of the breast pump in contact with the breast. The outer panel can be removably coupled to the inner panel with a clasp such that the outer panel can be at least partially removed from the inner panel to gain access to the opening(s). The inner panel can be removably coupled to another portion of the garment with the clasp, such that the inner pan& and the outer panel can both be removably coupled to the other portion of the garment.

BRIEF DESCRIPTION OF THE DRAWINGS

FIGS. 7A and 79 each depict the garment of FIG. 2A being used to support a breast pumping device.

FIG. 89 is an enlarged view of the region 8B of FIG. 8A.

FIG. 10 is a front view of a garment, according to an embodiment.

FIG. 14E is a front view of a second portion of the engagement mechanism of FIG. 14A; FIG. 14F is a back view of the second portion of the engagement mechanism of FIG. 14A; and FIG. 14G is a side view of the second portion of the engagement mechanism of FIG. 14A.

FIG. 39A is a front view of a portion of the garment of FIG. 36 with the third portion of the engagement mechanism and the outer panel detached from the second portion of the engagement mechanism.

FIG. 39B is a front view of a portion of the garment of FIG. 36 with the third portion of the engagement mechanism coupled to a selected loop of the extender of the garment of FIG. 36.

DETAILED DESCRIPTION

Figure 1:
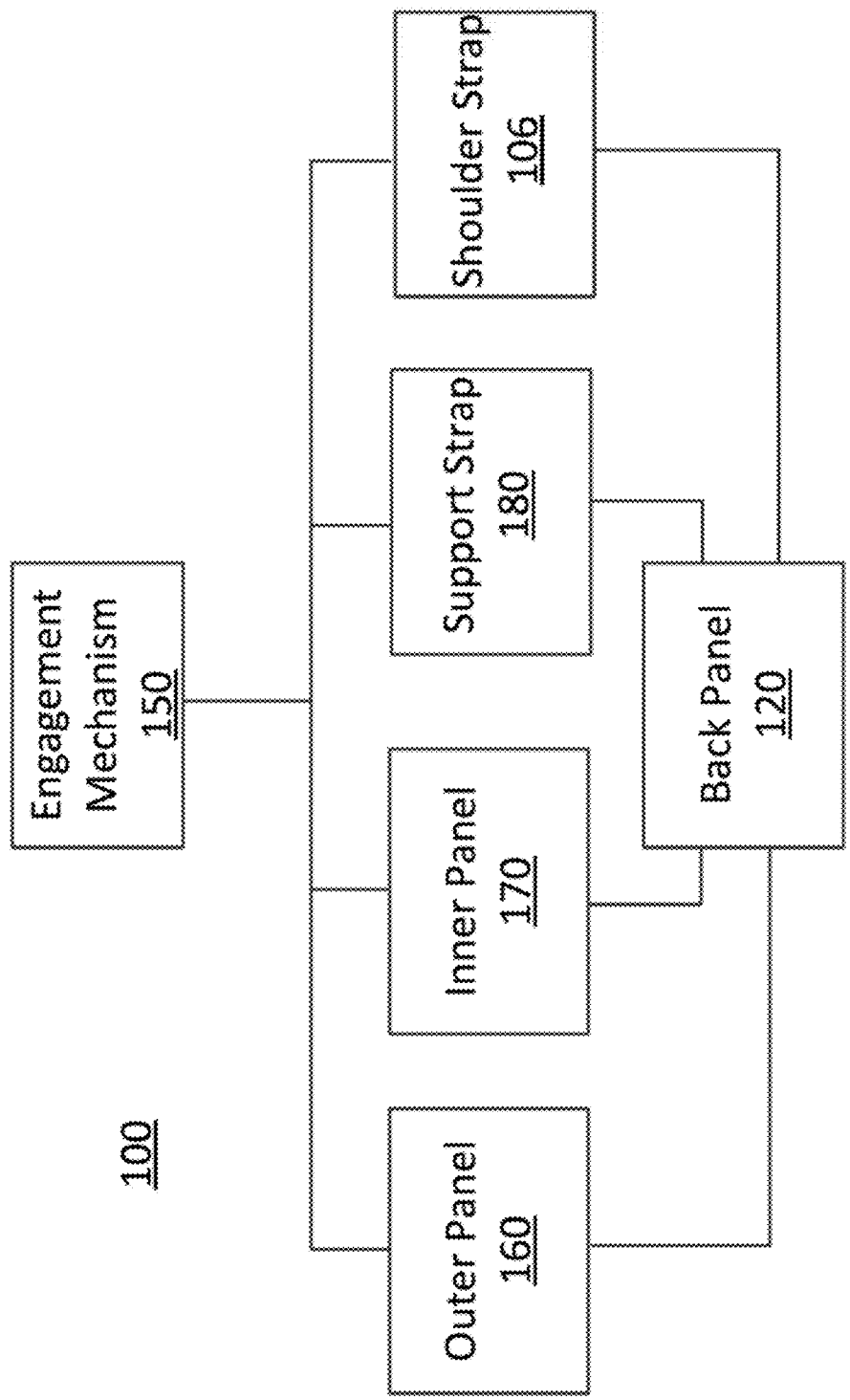
FIG. 1 is a schematic illustration of a garment, according to an embodiment.

Apparatuses, articles, processes for manufacture, garments, bustiers, breast pumping bras, and nursing bras that provide support to a wearer and/or at least a portion of a breast pump to aid with milk expression using a breast pump are described herein. For example, a garment, such as a bra, a tank top, a nightgown, or a bustier, may provide support for the weight of a breast pump body, milk container, and/or a wearer's breast, help secure the breast pump body in place, and/or stabilize the breast pump body for milk expression. Various embodiments may provide support to aid with creation of a tight seal between the wearer's breast and at least a portion of a breast pump body for milk expression (e.g., a breast shield and/or a let-down cushion of a breast pump body). The wearer of the garment may be able to pump breast milk without having to manually hold the breast pump body against themselves.

Garments in accordance with some embodiments may have openings formed/defined between layers of material that are fastened together and/or to panels of the garment to provide openings for access to a wearer's breasts. In particular, the garment may have an inner panel (e.g., a pumping panel) having two openings providing access to the wearer's breasts that are formed between respective sets of layers of material. The layers of material can be coupled together such that at least a portion of the layers of material overlap each other, or alternatively can be coupled together in an abutting or edge-to-edge relationship. In some embodiments, the layers of material can be coupled together such that a portion of the layers overlap each other and a portion of the layers are coupled together in an abutting or edge-to-edge manner. Each opening is between the corresponding set of layers of material and the layers of material are fastened together in such a manner to define/provide the respective opening.

In some embodiments, the garment may have an exterior surface of one or more panels of material that cover the inner panel. When the panels of material and the layers of material that cover an opening are moved, the wearer can insert a portion of the breast pump body through the opening, and the layers of material and/or the panels of material of the garment can aid in supporting the breast pump body and/or the wearer's breast. In some embodiments, the materials used for the inner and the exterior panels may be a fabric capable of being stretched to allow for pushing the material out of the way to insert the pump body portion. The fabric may also have some elasticity to fit snugly under and/or around the pump body portion for support and be capable of returning to the panel's original shape. In some embodiments, the garment may have elastic edges to prevent the garment from slipping down as well as providing additional support for the wearer's breasts.

In some embodiments, a garment (e.g., a bra) described herein can include an inner pumping panel with layers of material and an outer panel that can at least partially cover the inner pumping panel. A first portion of the layers of material of the inner pumping panel may be disposed on a left side of the bra to cover a portion of the wearer's left breast and can be fastened together such that at least a portion of the layers of material overlap and define a first opening. A second portion of the layers of material of the inner pumping panel may be disposed on a right side of the bra to cover a portion of the wearer's right breast, and can be fastened together such that at least a portion of the layers of material overlap and define a second opening. The first and second openings are each disposed at an oblique angle relative to a bottom edge of the bra and are sized and positioned to help support at least a portion of a breast pump disposable through the first and/or second opening Some embodiments may have one or more loops of a material (e.g., elastic, fabric, etc.) attached to the garment. Each loop may be designed to secure a portion of a breast pump in place (e.g., a loop to hook or fit around a breast shield to aid in the support of the breast pump body and milk container for pumping milk).

Some embodiments may have adjustable straps that may be selectively attached to the garment. For example, the garment can have a top line on the garment with corresponding attachment mechanisms to those found on the strap thereby allowing the strap to be attached thereto. For example, the top line may be a piece of material (e.g., an elastic band) attached to an edge of a panel (e.g., an inner panel) and the corresponding attachment mechanisms may be sewn to the garment with stitching between the elastic band and the fabric of the garment. The one or more attachment mechanisms (e.g., corresponding attachment mechanisms to the attachment mechanisms found on the strap) may be sewn in to the garment for selectively attaching a strap in one of a multiple different positions to support a breast pump body.

By way of further example, a neck strap can optionally be used and may extend around the back of the wearer's neck and be attached to the top line of the garment. The garment (e.g., a top line of a pumping/nursing bra) may have one or more selective attachment mechanisms (e.g., loops or hooks allowing for attachment of the strap to the garment). Multiple selective attachment mechanisms may be provided on the garment to provide multiple different positions for the strap. Attachment mechanisms may include, for example, hooks that may be selectively attached to a loop (e.g., a fabric, metal, or plastic loop), snaps, buttons and button holes, ribbon ties, lace ties, string ties, and/or any other attachment mechanism that can be selectively attached or detached. For example, a wearer could use a ribbon, lace, heavy string, etc. that could be threaded through a loop on the topline and tied where the two ends join. There may be a single strap and/or multiple straps that extend from one area of the bra to another as opposed to fitting around the neck. For example, a single strap could attach at the front topline, extend over the shoulder and hook at the topline below the underarm or back.

In some embodiments, the neck strap may have a single hook that can be attached to the garment or multiple hooks that may be attached to the garment. The neck strap may be used, for example, to ensure that the garment remains in place during breast pumping, particularly when the breast pump bottle becomes heavier as the container, which is used with the breast pump to collect milk, fills with milk. For example, a neck strap may encircle the neck of the wearer and have at least one hook attached to the top line of the garment to ensure that the garment remains in place during the use of a breast pump with at least one of the wearer's breasts. The neck strap may be used with or without shoulder straps of the garment, in some embodiments, a neck strap can include a comfort strap portion that has a width that is greater than a width of a typical strap to provide further comfort to the user. For example, the comfort strap portion can extend around the user's neck. In some embodiments, the comfort strap portion of the neck strap can be padded and/or can be formed with a material to provide softer comfort to the user's neck. In some embodiments, the width of the comfort portion can vary. For example, the width can be tapered or narrower at the ends of the comfort portion than at a center of the comfort portion.

In some embodiments, a pocket or a channel may be provided on a shoulder strap that contains and/or houses a cord or a strap with a hook or an attachment piece to connect to another area of the garment, as shown and described for example in International Application No. PCT/US16/43326 incorporated by reference above. The cord may be elastic to allow for the cord to be stretched and/or the cord may be stored within the pocket or channel rolled up into a coil, so that the cord can be extended and retracted. The cord may also have a slider to lengthen and shorten the strap as needed.

In some embodiments, the garment can include openings or holes along a perimeter top edge of the garment and the fastening mechanisms of the straps can be received therein to couple the straps to the garment. Such an embodiment is described in more detail below with reference to specific embodiments.

In some embodiments, a garment as described herein can be used in conjunction with a wearable breast pump and/or a wearable milk collection device. In such a garment, the garment can include an extender in place of the inner panel and the extender can be used to selectively adjust the position of the outer layer (e.g., the bra cup) to accommodate the wearable breast pump. The wearable breast pump or collection device can be positioned between the user's breast and the outer panel of the garment. The extenders can be attached to a portion of the engagement mechanism (e.g., engagement mechanism 150) on both the right side and left side of the garment. The outer panel of the garment (e.g., the right outer panel and the left outer panel) can be removably and selectively coupled to the extender to adjust the position and size of the outer panel in relation to the user's breast and the wearable breast pump or collection device.

Such adjustment of the size and position of the outer panel (e.g., the bra cup) may be desirable, for example, to prevent stretching of the cup portion (e.g., outer panel) of the garment during use of the wearable breast pump or milk collection device. Because such devices are disposed between the breast and the cup portion of the garment, and due to the size of some such devices, the cup portion of the garment may stretch or lose its form or shape during use of such devices and may then provide reduced support to the user's breast. Examples of such a garment are described in more detail below with reference to FIGS. 18A-21C and FIGS. 36-39C.

Other objects and advantages of the present invention will become apparent from the following detailed description when viewed in conjunction with the accompanying drawings, which set forth certain embodiments of the invention. It should be understood, however, that the disclosed embodiments are merely exemplary of the invention, which may be embodied in various forms. Therefore, the details disclosed herein are not to be interpreted as limiting, but merely as a basis for teaching one skilled in the art how to make and/or use the invention.

FIG. 1 is a schematic illustration of a garment 100. The garment 100 can be, for example, in the form of a bra, to be worn around a chest or upper torso of a wearer, typically a woman, who may desire to express milk from one or both breasts using a breast pump. The garment 100 can include an outer panel 160, an inner panel 170, one or more support straps 180, one or more shoulder straps 106 and a back panel 120. In some embodiments, each shoulder strap 106 can be coupled to the outer panel 160, the inner panel 170, and the support straps 180 via an engagement mechanism 150 (also referred to herein as a "clasp"). The support straps ISO can be coupled on a first end to the back panel 120, and on a second end to one of the shoulder straps 106 via the engagement mechanism 150. In alternative embodiments, the support straps 180 can be attached to a lower band of the garment (not shown) rather than to the back panel 120. In some embodiments, the back panel 120 and a lower band can be formed integrally. Each of the shoulder straps 106 can have a first end coupled to the support strap 180 (via the engagement mechanism 150) and a second end coupled to the back panel 120 and/or a lower band or other portion of the garment 100, via, for example, stitching. The outer panel 160 and the inner panel 170 can be attached to the back panel 120 and/or along a bottom band of the garment 100, for example, along a bottom edge of the outer panel 160 and/or along a bottom edge of the inner panel 170, via, for example, sewing/stitching. Similarly, the outer panel 160 and the inner panel 170 can be coupled together along at least a portion of a bottom edge and/or along at least a portion of a top edge of the outer panel 160 and the inner panel 170.

The inner panel 170 and the outer panel 160 can each include one or more panels each formed with one or more layers of material. For example, the outer panel 160 can include a right outer panel (not shown in FIG. 1) and a left outer panel (not shown in FIG. 1). The inner panel 170 can include a right inner panel (not shown in FIG. 1) and a left inner panel (not shown in FIG. 1). The right inner panel and the left inner panel can be shaped and sized for coverage of a wearer's right breast and left breast, respectively. Each of the right inner panel and the left inner panel can include a first portion and a second portion that are coupled together such that a portion is unattached and can define an opening between the first portion and the second portion. In some embodiments, the first portion and the second portion can include an overlapping portion, which can define the opening. The first portion and the second portion can be separated by, for example, moving the first portion and the second portion away from each other, thereby creating the opening and providing access to the user's breast. A breast pump can then be inserted through the opening and the inner panel 170 can help support the breast pump during milk extraction.

In some embodiments, the inner panel 170 can include one or more holes or apertures defined in an upper edge of the inner panel 170. In some embodiments, a separate component defines the holes and is coupled to the inner panel 170. The holes are described in more detail, fir example, with reference to holes 243 described below with reference to FIGS. 5A-5D. A center strap (not shown in FIG. 1) can be attached to the inner panel 170 via selective releasable engagement with any of the holes. The center strap can be the same or similar in structure and/or function to the center strap 246 described below.

The engagement mechanism 150 can be used to allow the outer panel 160, the inner panel 170, the shoulder strap 106 and the support strap 180 to be releasably coupled to one another in various configurations. For example, in some embodiments, at least a portion of the outer panel 160 can be releasably coupled to and decoupled from the inner panel 170, and at least a portion of the inner panel 170 can be releasably coupled to and decoupled from the support strap 180 and the shoulder strap 106. When the outer panel 160 is coupled to the inner panel 170, the inner panel 170 and the outer panel 160 can collectively be coupled to and decoupled from the support strap 180 and shoulder strap 106.

In some embodiments, the engagement mechanism 150 can include two or more portions (not shown in FIG. 1), with each of the two or more portions associated with at least one of the outer panel 160, the inner panel 170, the support strap 180 and the shoulder strap 106. Thus, the outer panel 160, the inner panel 170, the support strap 180 and the shoulder strap 106 can be coupleable to and decoupleable from one another via the two or more portions of the engagement mechanism 150. For example, in some embodiments, the engagement mechanism 150 can include a first portion that can be releasably coupled to a second portion, and the second portion can be releasably coupled to a third portion. In some embodiments, the engagement mechanism 150 can include a first portion and a second portion. The first portion can be coupled to the support strap 180 and shoulder strap 106 and the second portion can be coupled to the inner panel 170. In such an embodiment, a separate coupling mechanism can be used to releasably couple the outer panel 160 to the inner panel 170. For example, a coupling mechanism such as a snap mechanism, a hook and loop coupling, VELCRO, etc.

In some embodiments, the engagement mechanism 150 can include a first portion fixedly coupled to the support strap 180 and fixedly coupled to the shoulder strap 106, a second portion fixedly coupled to the inner panel 170 and a third portion fixedly coupled to the outer panel 160. In such an embodiment, the second portion of the engagement mechanism 150 can be releasably coupled to the first portion to couple the inner panel 170 to the support strap 180 and the shoulder strap 106. The third portion of the engagement mechanism 150 can be releasably coupled to the second portion to releasably couple the outer panel 160 to the inner panel 170.

In some embodiments, the two or more portions of the clasp 150 can include mating features. The mating features can include, for example, complementary mating shapes or any other suitable coupling mechanisms such that the two or more portions of the clasp 150 are releasably coupleable to and decoupleable from one another. The outer panel 160, the inner panel 170, the support strap 180 and the shoulder strap 106 can each be fixedly coupled to a portion of the clasp 150 via any suitable coupling mechanism. For example, in some embodiments, a portion of the outer panel 160, the inner panel 170, the support strap 180 and/or the shoulder strap 106 can be fixedly coupled to a portion of the clasp 150 with stitching as described in more detail herein.

In use, the garment 100 can be worn around a chest or upper torso of a wearer. If access to a breast of the wearer is desired, such as for breast pumping, the outer panel 160 (e.g., the right outer panel and/or the left outer panel) can be detached from the inner panel 170 (e.g., the right inner panel and/or the left inner panel) by detaching or uncoupling the third portion from the second portion of the engagement mechanism, 150. The outer panel 160 can then be moved (e.g., folded down) such that the inner panel 170 is accessible. As described above, the first portion and the second portion of the inner panel (e.g., the right inner panel and/or the left inner panel) can be separated (e.g., stretched or folded) to create an opening through which the wearer's breast is accessible and a portion of a breast pump can be inserted. If further access to the breast of the wearer is desired, for example, for nursing, the inner panel 170 can be detached from the support strap 180 and shoulder strap 106 by removing/detaching the second portion of the engagement mechanism 150 from the first portion of the engagement mechanism 150. Because the support strap 180 and shoulder strap 106 remain coupled to the back panel 120, the garment 100 can still be held in place on the body of the wearer via the shoulder straps 106 and support straps 180. In some embodiments, the outer panel 160 and the inner panel 170 can be detached from shoulder strap 106 and support strap 180 simultaneously without decoupling the outer panel 160 from the inner panel 170. When desired, the inner panel 170 and the outer panel 160 can be reattached to shoulder strap 106 and support strap 180 by recouping the second portion to the first portion of the clasp 150, and the outer panel 160 can be recoupled to the inner panel 170.

Figure 2A:
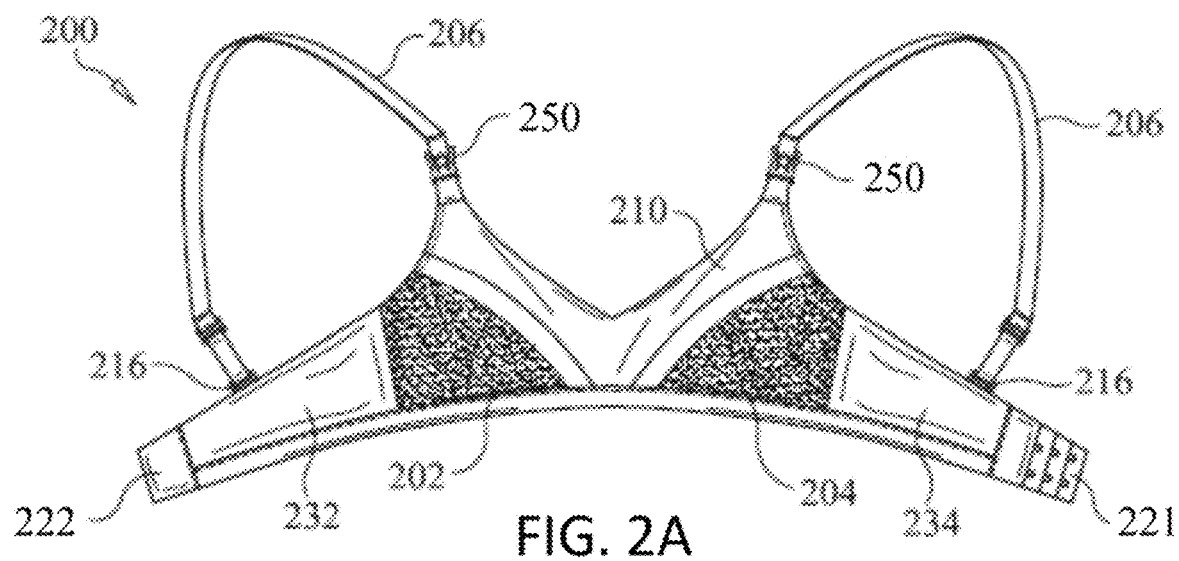
FIG. 2A is a front view of a garment, according to an embodiment.

FIGS. 2A-2E illustrate various different views of a garment 200 in the form of a bra, to be worn around a chest or upper torso of a wearer, typically a woman, who may desire to express milk from one or both breasts using a breast pump. FIG. 2A illustrates a front view of an assembled garment 200, which can include an inner panel or pumping panel, an exterior panel, and a back panel. The inner panel, exterior panel and back panel can each include one or more separate panel material portions to, for example, form a right side panel and a left side panel of the garment 200. For example, the exterior panel can include a left side panel and a right side panel. In addition, one or more layers of material can be used to form each of the inner panel (pumping panel), exterior panel and/or back panel. For example, the inner panel can include two, three, four or more layers of material coupled together.

The exterior panel can include a first panel 202 and a second panel 204 (e.g., a right side panel and a left side panel, respectively). The pumping panel can include multiple layers of material that are coupled together in such a manner to define an opening or hole as described in more detail below. The layers of material can be coupled together such that at least a portion of the layers of material overlap each other. In some alternative embodiments, the layers of material may not overlap, but instead can be coupled together in an abutting or edge-to edge relationship to each other. In one embodiment, the layers of material include a center layer 210 (see, e.g., FIG. 2A), a left inner layer 214 (see, e.g., FIG. 2B) and a right inner layer 212 (see, e.g., FIG. 2B). The garment 200 can include first and second shoulder straps 206 (also referred to as "shoulder straps") having a fastening mechanism 216 coupled to a first end, and a second end of each of first and second shoulder straps 206 being attachable to first and second engagement mechanisms 250. The garment 200 also includes closures 221 and 222, a first wrap-around panel 232, and a second wrap-around panel 234. For ease of discussion, center layer of material 210 may also be referred to herein as "center layer 210."

The components of garment 200 (e.g., panels and/or layers) may be made from any appropriate material, including, but not limited to, fabric, cotton, spandex, elastic, polyester, rayon, and mesh. Where appropriate, one or more of the components may be fabricated to stretch or be temporarily reshaped and/or repositioned. In some embodiments, first panel 202 and second panel 204 may be made from a lightweight material that may, in some instances, include a decorative design or accent (e.g., lace or decorative pattern). The first panel 202 and/or the second panel 204 may serve to, for example, smooth the exterior surface of garment 200 to provide a seamless appearance when worn under another garment (e.g., shirt or blouse). In some embodiments, first panel 202 and/or second panel 204 may assist in the positioning, support, and/or retention of a portion of a breast pump, such as a breast shield 294 of a breast pump 290 (shown in FIGS. 7A and 7B), within an opening 230. Additionally, or alternatively, first panel 202 and/or second panel 204 may assist in the positioning, support, and/or retention of a portion of a pumping container, such as a pumping container of the breast pump 290 (shown in FIGS. 7A and 7B) within opening 230, and/or a breast pad, such as breast pad 240, which will be discussed in greater detail below with regard to FIGS. 4A-4C.

First and second wrap around panels 232 and 234 may be affixed to a portion of, for example, the exterior panel or the pumping panel or the back panel, or any combination of these panels, and may serve to wrap around the body of a wearer (typically the side and back) so that the garment 200 may close around the wearer via closures 221 and 222 in a manner similar to known garments/brassieres.

Figure 2B:
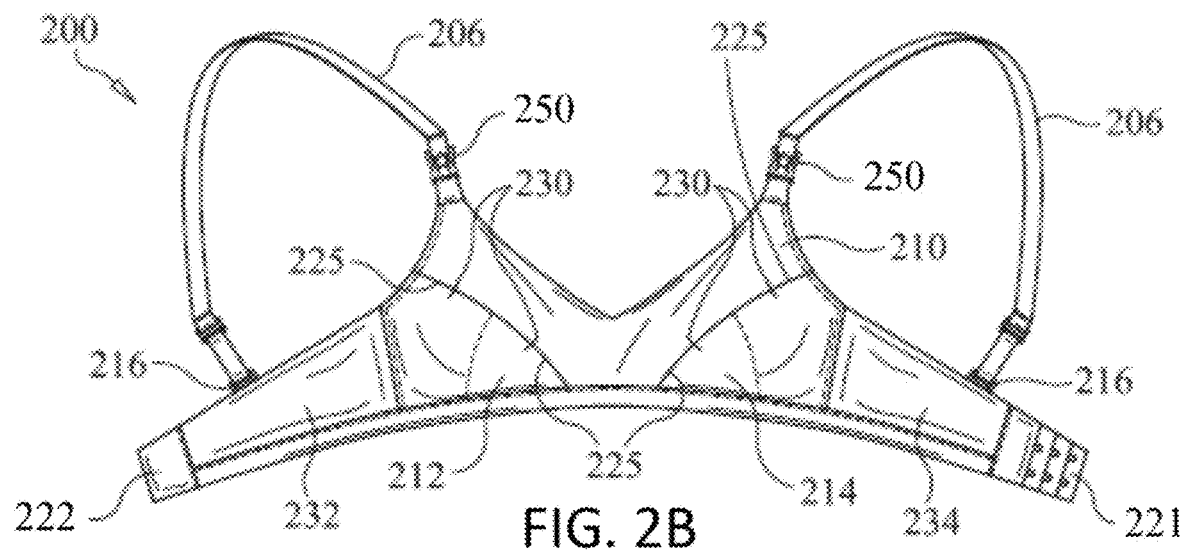
FIG. 2B is a front view of the garment of FIG. 2A with an outer layer removed to illustrate a front view of an inner layer of the garment.

FIG. 2B illustrates a front view of garment 200, without first panel 202 and second panel 204 of the exterior panel to expose a left inner layer 214 and a right inner layer 212. The left inner layer 214 may be situated on the left side of garment 200 (covering the left breast), within the pumping panel, and arranged to partially overlap a portion of center layer 210 positioned on the left side of the garment 200. Left inner layer 214 may be partially affixed (e.g., via sewing, chemical bonding, heat bonding, etc.) to center layer 210 at upper and/or lower affixed regions 225. A region, between the upper and lower affixed regions 225, where the left inner layer 214 and the center layer 210 are not affixed to one another defines an opening 230 between the left inner layer 214 and the center layer 210.

The right inner layer 212 may be situated on the right side of garment 200 (covering the right breast) and arranged to partially overlap a portion of center layer 210 positioned on the right side of the garment 200. Right inner layer 212 may be partially affixed (e.g., via sewing, chemical bonding, heat bonding, etc.) to center layer 210 at upper and/or lower affixed regions 225. A region between the upper and lower affixed regions 225 where the right inner layer 212 and the center layer 210 are not affixed to one another defines an opening 230 between the right inner layer 212 and the center layer 210.

In this embodiment, an attachment line (e.g., stitching) of the affixed regions 225 between the right inner layer 212 and the center layer 210 and between the left inner layer 214 and the center layer 210 (e.g., overlapping material portions) and/or opening(s) 230 are obliquely oriented at an angle relative to the bottom edge of the garment 200. Exemplary angles for the attachment line of the partially overlapping and/or overlapped left inner layer 214 and center layer 210 may include any angle within the range of about 30° to about 80° relative to the bottom edge of the garment 200. Exemplary angles for the attachment line of the partially overlapping and/or overlapped right inner layer 212 and center layer 210 may include any angle within the range of about 100° to about 150° (i.e., about 30° to about −80°) relative to the bottom edge of the garment 200. Thus, each of the openings 230 is angled in a direction upwardly from a center of the garment. In some embodiments, the oblique orientation of the opening 230 may be substantially (+/−10%) 45° or 135° for the opening 230 on the first and second side of garment 200, respectively. In some alternative embodiments, the angle of the attachment lines and openings 230 can be angled in an opposite direction. For example, the attachment line on the right side of the bra can angle downwardly from a top edge of the bra toward the wrap around panel 234 (e.g., at an angle in the range of about 30° to about 80° relative to the bottom edge of the garment 200) and the attachment line on the left side of the bra can angle downwardly from a top edge of the bra toward the wrap around panel 232 (e.g., at an angle in the range of about 100° to about 150° relative to the bottom edge of the garment 200).

Opening(s) 230 may be sized and positioned within the garment 200 to allow at least a portion of a breast pump, such as the breast shield 294 of the breast pump, to be inserted into the opening(s) 230 and contact the wearer's breast(s). In one embodiment, insertion of the breast shield 294 into opening 230 may be achieved by separating a portion of the center layer 210 positioned between affixed regions 225 from the left inner layer 214 and/or the right inner layer 212. The separation may be achieved by lifting, pushing and/or pulling the center layer 210, the left inner layer 214, and/or the right inner layer 212 into a desired configuration. The overlapping portions of right inner layer 212 and center layer 210 and left inner layer 214 and center layer 210 defining the openings 230 provide a width or depth of material that defines a passageway to support at least a portion of the breast pump (e.g., breast shield 294) inserted therethrough.

The oblique angle of the opening(s) 230 can provide flexibility and movement of the portion of the breast pump along the oblique angle of the opening 230 to, for example, align with a nipple of the wearer's breast or breasts. Thus, a user/wearer can have improved ability to position the breast pump at a desired angle and/or orientation within the opening 230. For example, the oblique angle of the opening 230 can allow the wearer to reposition the breast pump left-to-right and/or up/down within the opening 230. The oblique opening 230 can also provide increased support of the breast pump as the pumping container (e.g., milk bottle) increases in weight from collection of the expressed milk. In some embodiments, first panel 202 and/or second panel 204 may be moved or repositioned by a wearer to access opening(s) 230. In some cases, first panel 202 and/or second panel 204 may be removed, either from garment 200, or pulled down to expose center layer 210, left inner layer 214, right inner layer 212 and/or opening 230. In some embodiments, garment 200 may not include first panel 202 and/or second panel 204. In these embodiments, movement of the center layer 210, left inner layer 214, and/or right inner layer 212 may expose opening 230.

Figure 2C:
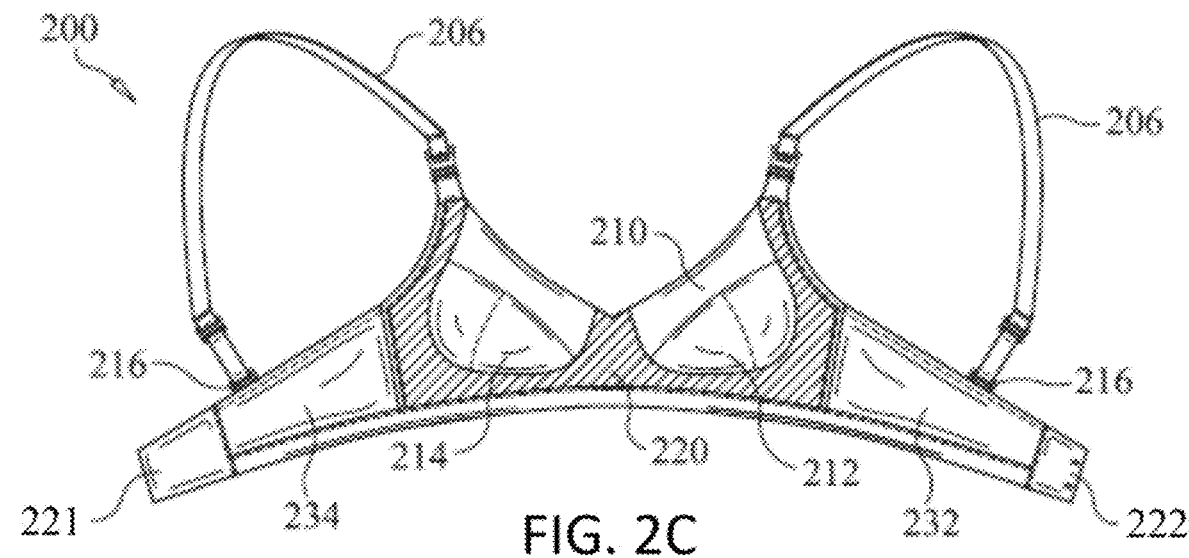
FIG. 2C is a back view of the garment of FIG. 2A.

FIG. 2C illustrates a back or rear view of garment 200, which shows an optional back panel 220. Back panel 220 may serve to provide structural support for the garment 200 as well as the wearer's breasts when worn. In some embodiments, back panel 220 may be made of a material, or layers of material, that are more stiff than, for example, center layer 210, the left inner layer 214, the right inner layer 212, first panel 202, and/or second panel 204. Back panel 220 may be configured in a "w"-type of shape, wherein there is material for the back panel 220 in the center and sides and two curve-shaped cutout sections with no material. The curve-shaped cutout sections may be configured to align with and fit underneath/around the wearer's breasts. It will be understood by those of skill in the art that "material" as used herein is not limited to a single panel or layer of fabric and may be any combination materials or layers of material.

It should be noted that in some instances, garment 200 may not include optional back panel 220. In these instances, for example, a bottom edge of first wrap around panel 232, center layer 210, left inner layer 214, right inner layer 212, and/or second wrap around panel 234 may be affixed to one another and/or to a strap (not shown) or other mechanism for facilitating the construction of garment 200 and/or the attachment of closures 221 and 222. Additionally, when back panel 220 is not included in garment 200, first and second portions of engagement mechanisms 250 (described in detail below with reference to FIGS. 3A and 3B) may be attached to, for example, center layer 210, left inner layer 214, and/or right inner layer 212, respectively.

Additionally, center layer 210, left inner layer 214, right inner layer 212, and back panel 220 may include one or more different layers, pieces of fabric, panels, etc. affixed (e.g., sewn, chemically bonded, etc.) to one another.

Figure 2D:
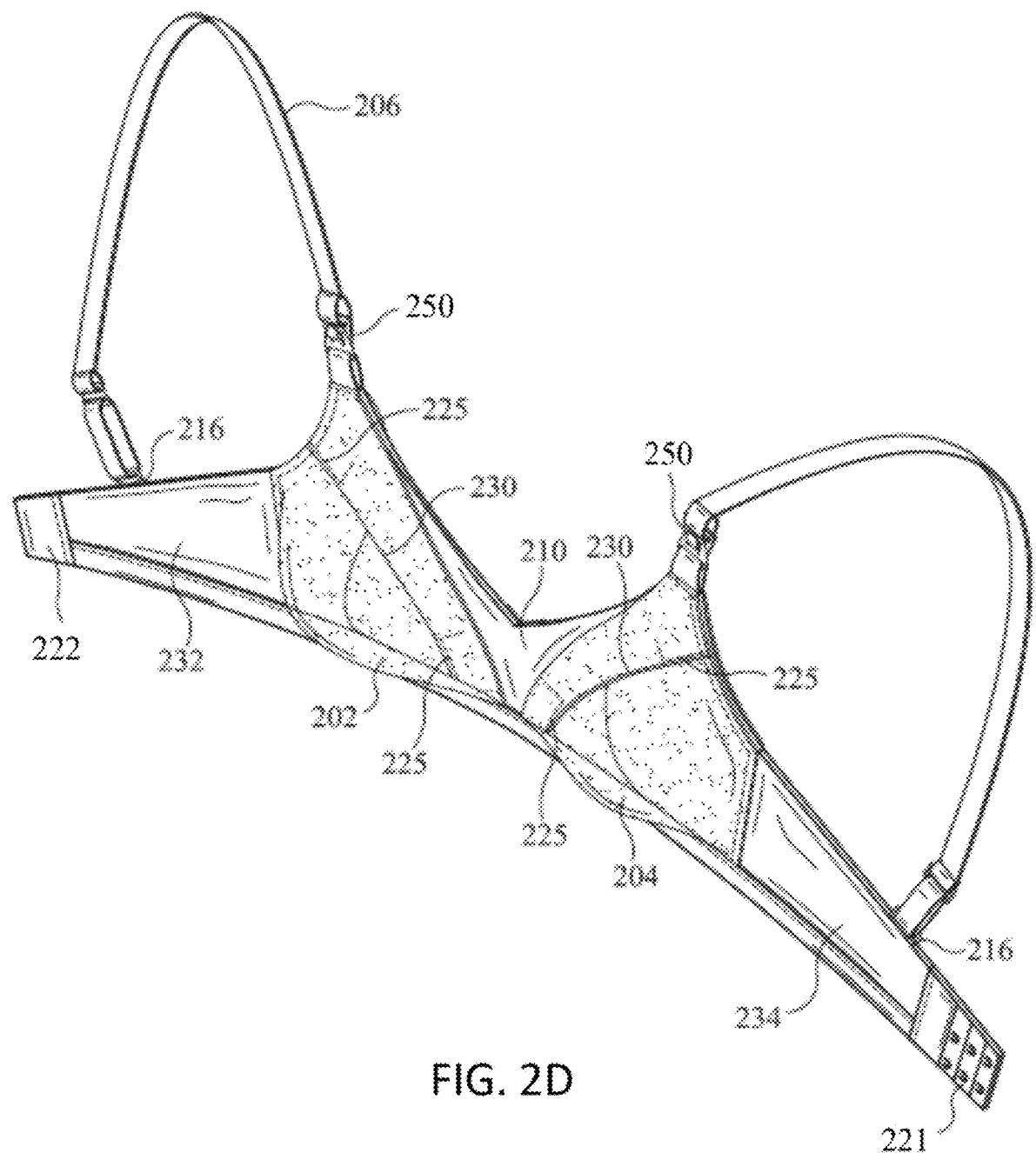
FIG. 2D is a front perspective view of the garment of FIG. 2A.
Figure 2E:
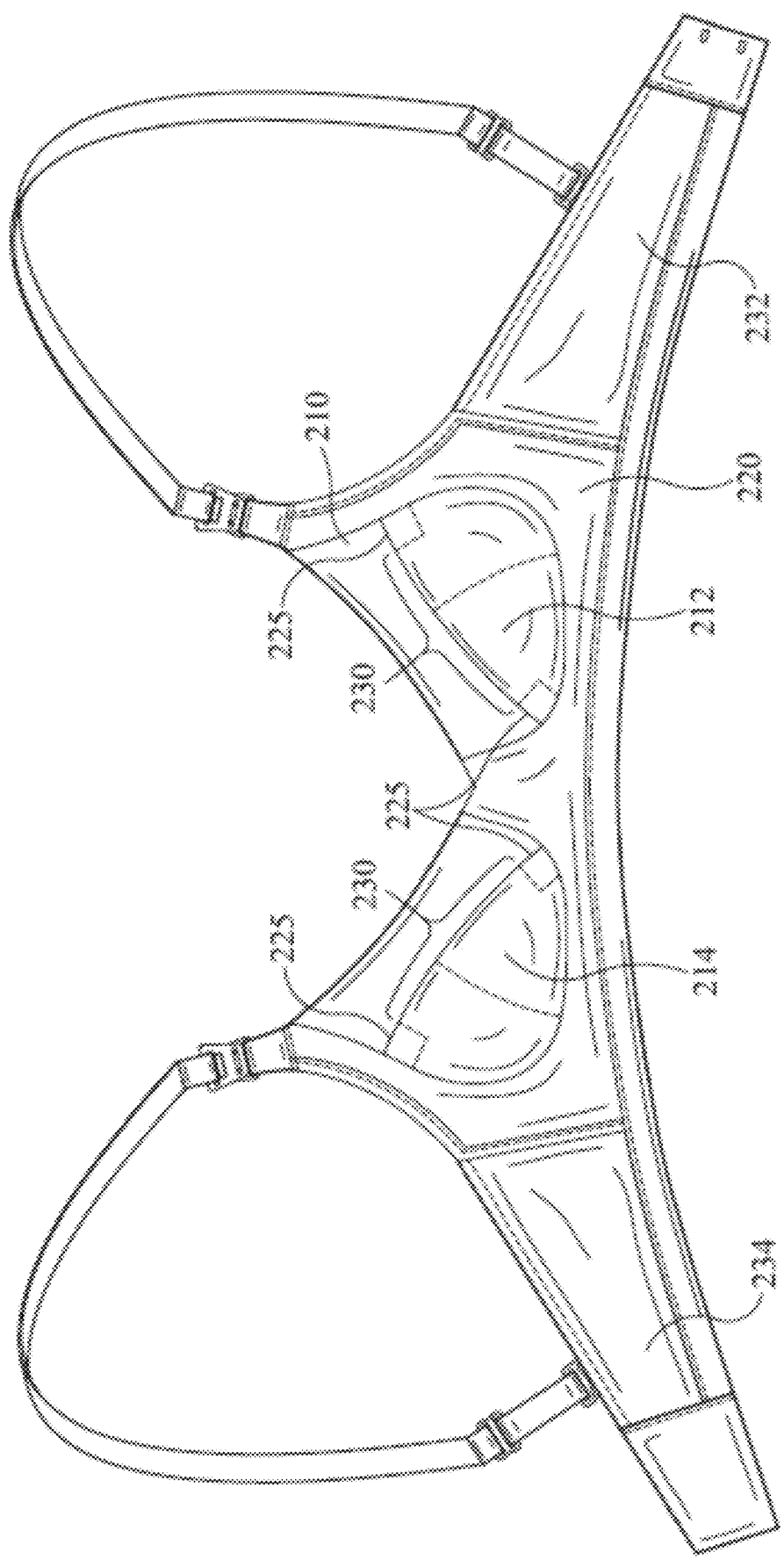
FIG. 2F is a back view of the garment of FIG. 2A illustrating affixed regions and openings of the garment that can receive a portion of a breast pumping device therethrough.

FIG. 2D provides a perspective illustration of the garment 200 showing how first panel 202, second panel 204, center layer 210, left inner layer 214, and/or right inner layer 212 may extend perpendicularly or substantially perpendicularly, outward from a planar surface of garment 200 to, for example, accommodate a three dimensional shape of a wearer's breasts. Additionally, FIG. 2D also illustrates that upper and/or lower affixed regions 225 are sewn and a region therebetween allows for opening 230. FIG. 2E provides an alternative rear view of garment 200 showing affixed regions 225 and openings 230.

Figure 3A:
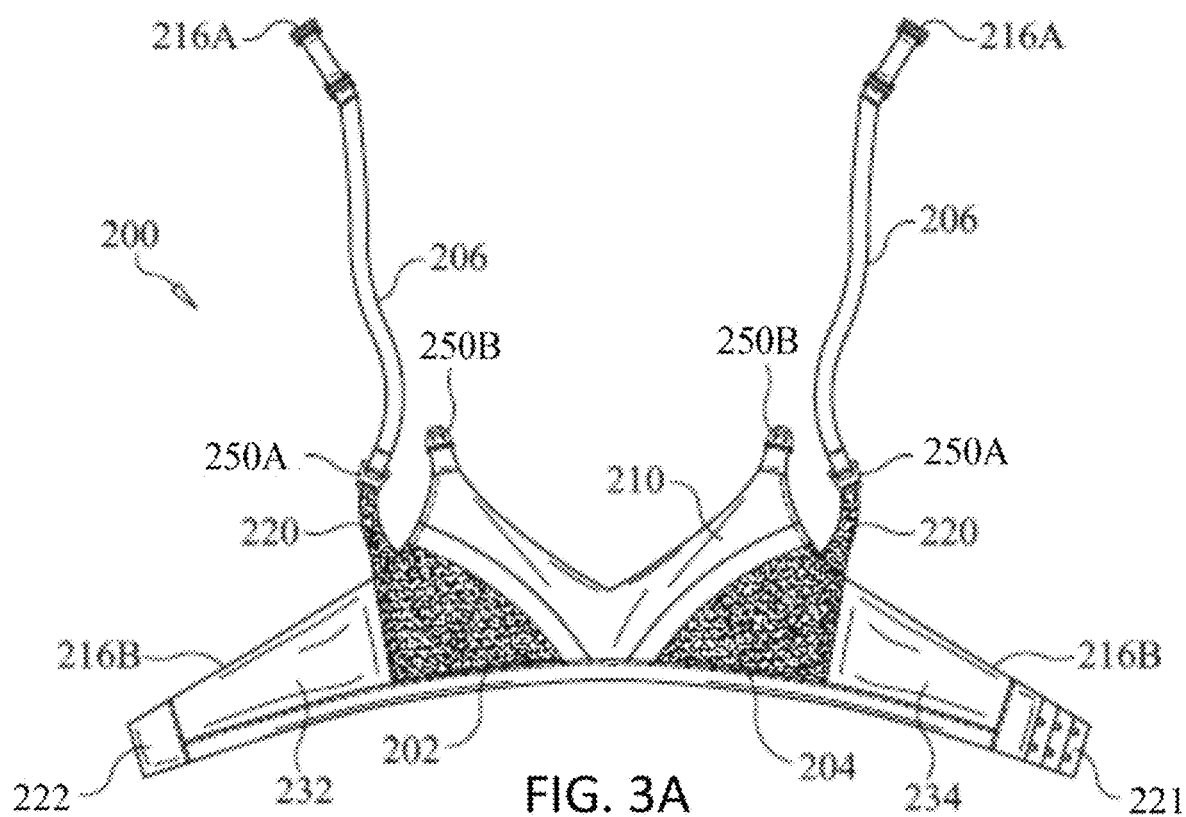
FIG. 3A is a front view of the garment of FIG. 2A with an engagement mechanism in a disengaged configuration.
Figure 3B:
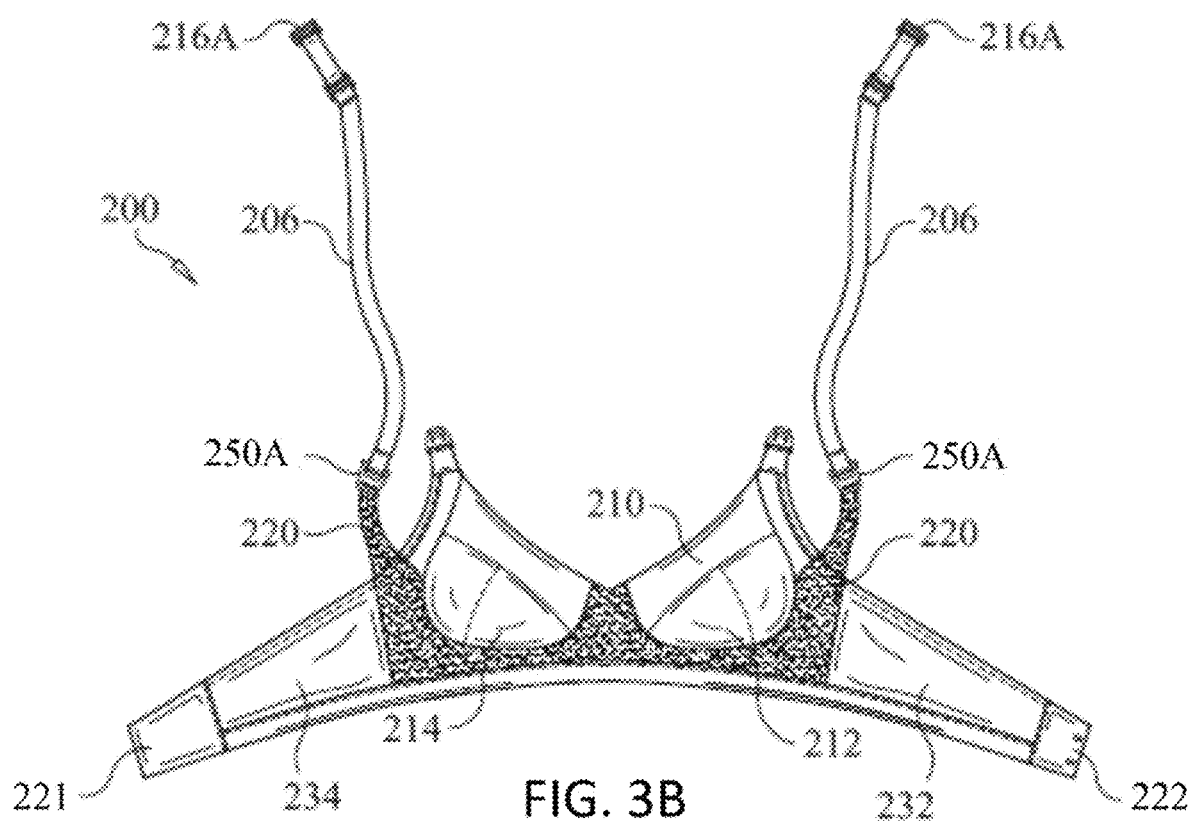
FIG. 3B is a rear view of the garment of FIG. 3A the configuration of FIG. 3A.

In some embodiments, as shown in FIG. 3A, the engagement mechanisms 250 include a first engagement member 250A that can be coupled to (or engage or attach to) a second engagement member 250B (FIGS. 3A and 3B illustrate the first and second engagement members decoupled or disengaged from each other). Engagement members 250A can be attached to the back panel as shown in FIGS. 3A and 3B. Engagement members 250B can be coupled to the center layer 210 as shown in FIG. 3A. The first and second engagement members 250A and 250B and/or an extension portion of back panels 220 may each be affixed to a shoulder strap 206 sized and shaped to enable a wearer to put on and take off garment 200 as well as provide support for the wearer's breasts and garment 200 when worn. Shoulder straps 206 can include a first fastening member 216A, which will be discussed in greater detail below with reference to FIGS. 5A-5D.

FIG. 3B illustrates a back or rear view of garment 200, which shows the extension portions of back panel 220 affixed to engagement members 250A when the engagement members 250A and 250B are not engaged together. When engagement members 250A and 250B are not engaged together, a portion of center layer 210, left inner layer 214, right inner layer 212, first panel 202, and/or second panel 204 may be decoupled from the back panel 220 as shown. In this way, when worn by the wearer, the decoupled engagement members 250A and a portion of garment 200 affixed thereto may be repositioned or moved to expose a portion of the wearer's underlying breast(s).

Figure 4A:
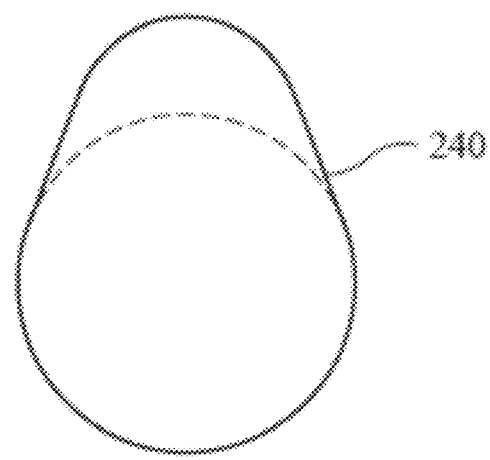
FIG. 4A is a front view of an optional breast pad of the garment of FIG. 2A.
Figure 4B:
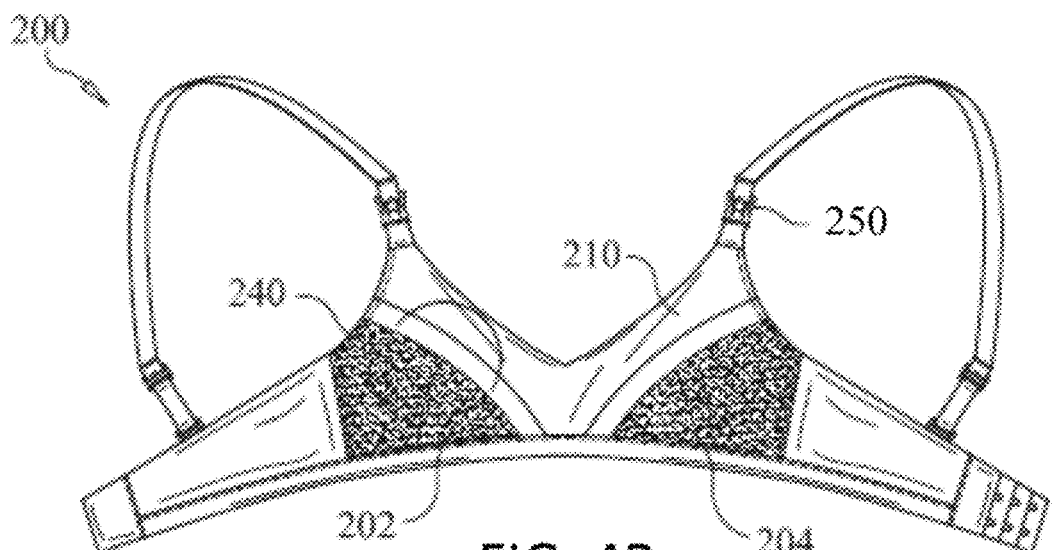
FIG. 4B is a front view of the garment of FIG. 2A illustrating the optional breast pad disposed therein at a first location.
Figure 4C:
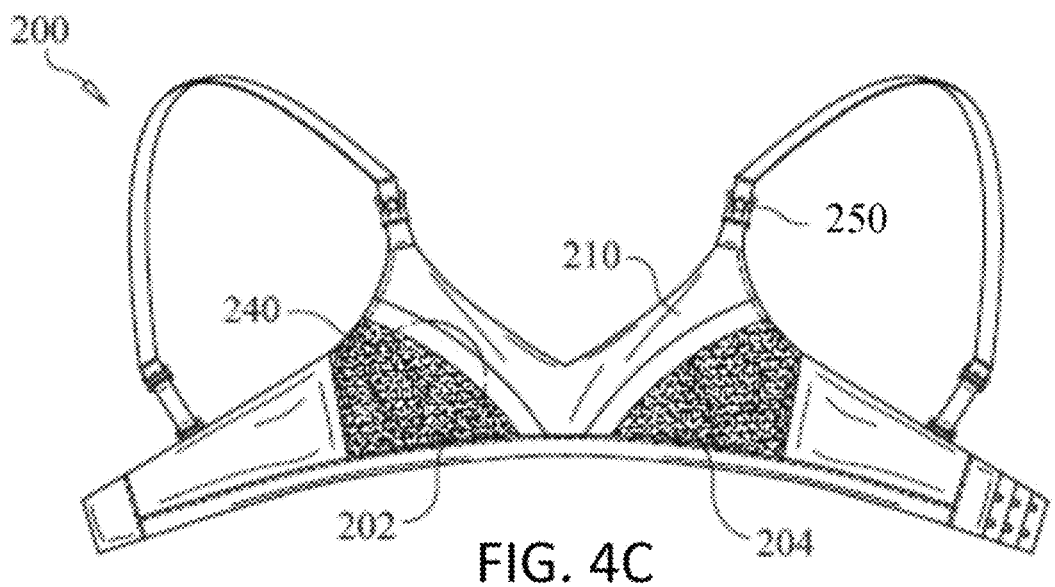
FIG. 4C is a front view of the garment of FIG. 2A illustrating the optional breast pad disposed therein at a second location.

FIG. 4A illustrates a breast pad 240 that can be removably inserted into garment 200 between a portion of first panel 202 and a portion of the right inner layer 212 and/or a portion of center layer 210 as shown in FIGS. 4B and 4C. Breast pad 240 may be manufactured from, for example, fabric, foam, rubber or some combination thereof. Breast pad 240 may be either disposable or reusable. When reusable, breast pads 240 may be manufactured to be machine or hand washable. In some embodiments, breast pad 240 may serve to smooth the exterior surface of garment 200, add volume to the garment 200, and/or protect an underlying breast or nipple of the wearer.

Figure 5A:
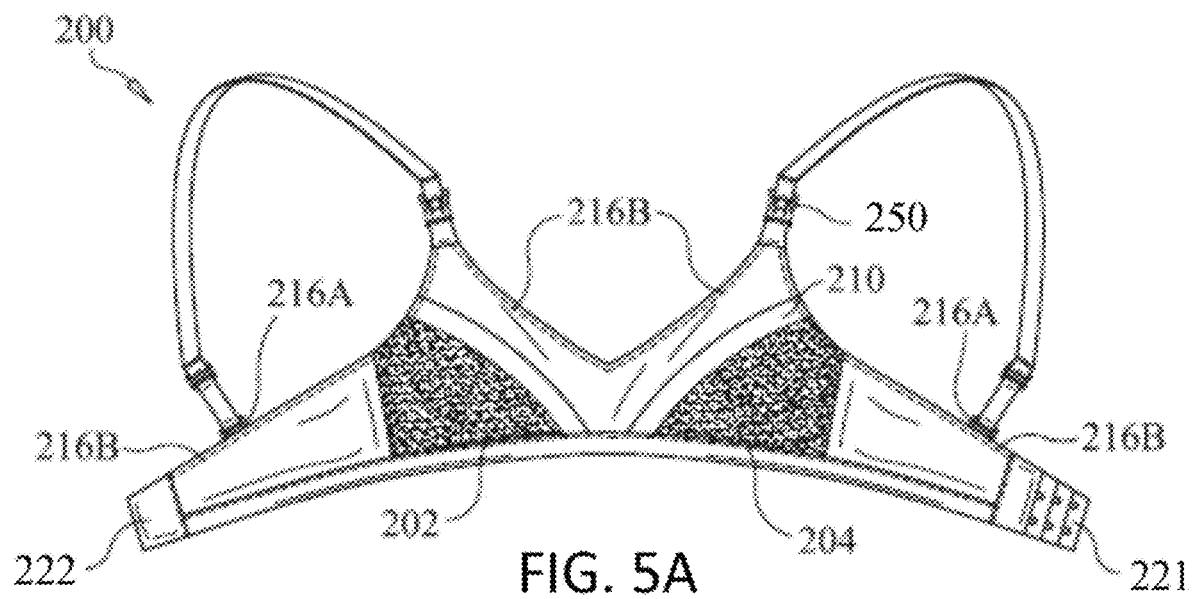
FIG. 5A is a front view of the garment of FIG. 2A illustrating openings defined along a perimeter top edge of the garment that can be used to couple straps thereto.
Figure 5B:
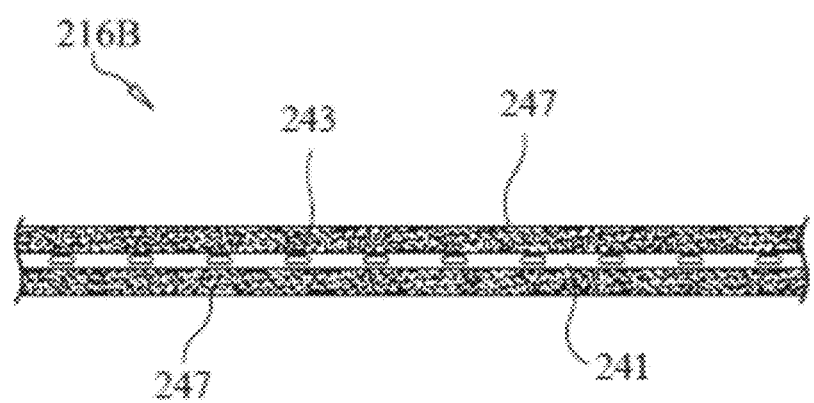
FIG. 5B is an enlarged view of the openings/holes defined along the perimeter top edge of the garment to which the straps of the garment of FIG. 2A can be secured.

FIGS. 5A-5D provide illustrations of how the shoulder straps 206 can be coupled to the garment 200. As described above, the straps 206 each include a first fastening member 216A coupled to an end thereof. To couple the strap 206 to the body of the garment 200, the first fastening members 216A can be coupled to a second fastening member 216B disposed along an upper/top perimeter portion of the body of the garment 200 as shown in FIG. 5A. As shown in FIG. 5B, the second fastening member 216B can include, for example, a length of fabric or elastic material 241 that defines multiple openings or holes 243 along a length thereof. In some embodiments, holes 243 may resemble button holes as shown in FIG. 5B. The length of fabric or elastic material 241 may be affixed to, or sewn into, a portion 247 (e.g., an upper edge) of garment 200. For example, in some embodiments, the length of fabric 241 can be disposed between the center layer 210 and the inner layers 212, 214 such that the holes 243 defined in the length of fabric 241 are visible along a top edge of the garment 200.

Figure 5C:
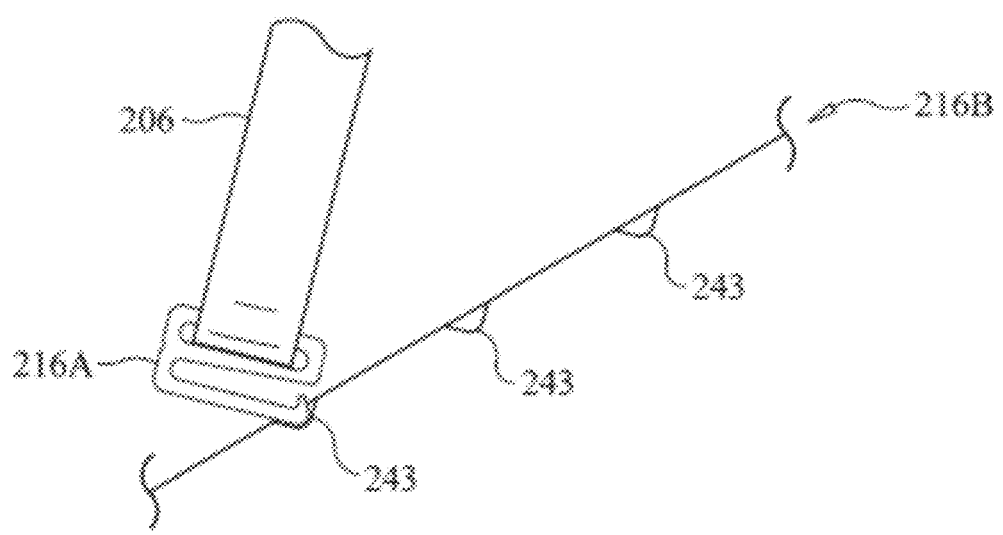
FIGS. 5C and 5D are each an enlarged view of a portion of the perimeter top edge of the garment of FIG. 5A illustrating the fastening mechanisms of the straps being inserted into the openings/holes defined therein.
Figure 5D:
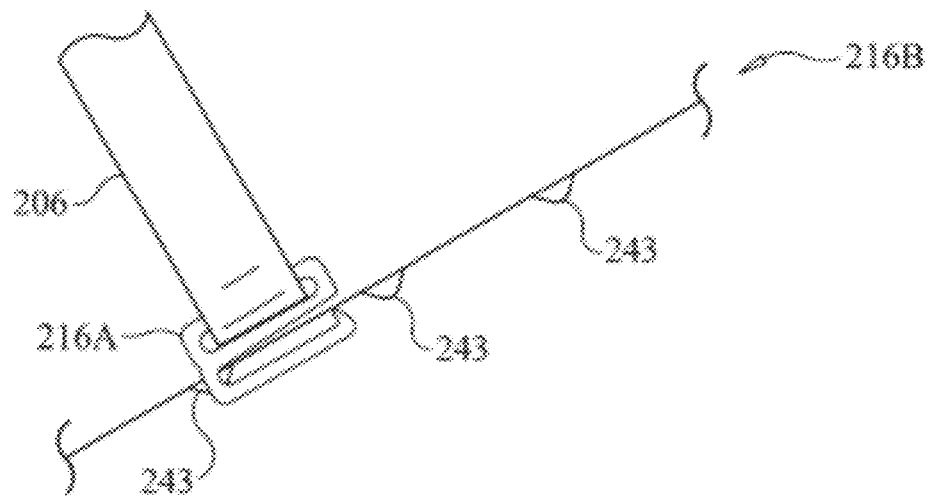

FIGS. 5C and 5D illustrate how a fastening member 216A affixed to a shoulder strap 206 can be releasably coupled to a selected hole 243 of the second fastening member 216B. As best shown in FIGS. 5C and 5D, first fastening member 216A may resemble a hook that can be inserted into a selected hole 243. The fastening member 216A can then be positioned within the hole 243 to be substantially parallel to a plane of the second fastening member 216B as fastened to garment 200 (see FIG. 5D). The first fastening member 216A may be securely and removably attached to a selected one of the holes 243 of fastening member 216B by virtue of its positioning or engagement within the hole 243 and/or via friction.

As shown in FIG. 5A, the garment 200 can include a fastening member 216B at multiple locations along an upper perimeter of the garment 200. For example, a first part of fastening member 216B can be disposed along a portion of the upper perimeter of garment 200 and a second part of fastening member 216B can be disposed along an outside perimeter of a portion of first wrap around panel 232 and second wrap around panel 234. A portion of the second part of the fastening member 216B may also be affixed to the upper perimeter of the center layer 210.

Figure 6A:
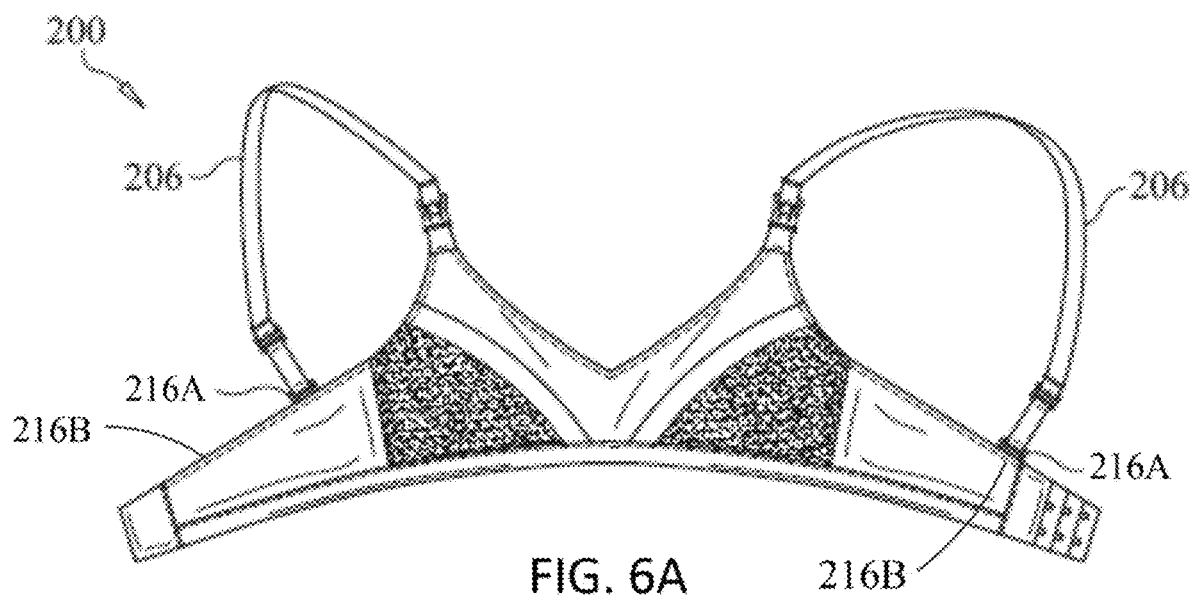
FIG. 6A is a front view of the garment of FIG. 2A illustrating a first fastening mechanism attached at a first location along a first wrap-around panel on a first side of the garment and a second fastening mechanism attached at a second location along a second wrap-around panel of the garment on a second side of the garment.

The multiple holes 243 of second fastening member 216B provides adjustability and allows a wearer to couple a strap 206 to the garment 200 at various different locations to, for example, improve the comfort of garment 200 when worn, and/or provide support for breast weight, a portion of the breast pump, and/or a container of pumped breast milk, (e.g., such as pumping container 100) as may be used when expressing milk from a breast. For example, as shown in FIG. 6A, a wearer may couple the first fastening member 216A of a first shoulder strap 206 to a hole 243 of second fastening member 216B at a position on the second wrap around panel 234, and a second shoulder strap 206 with a first fastening member 216A can be coupled to a hole 243 of second fastening mechanism 216B at a position on the first wrap around panel 232 closer to the center layer 210 than the first shoulder strap 206. The adjustability of the attachment of the straps 206 to the body of the garment 200 allows a wearer to adjust the positioning of the straps 206 as desired.

Figure 6B:
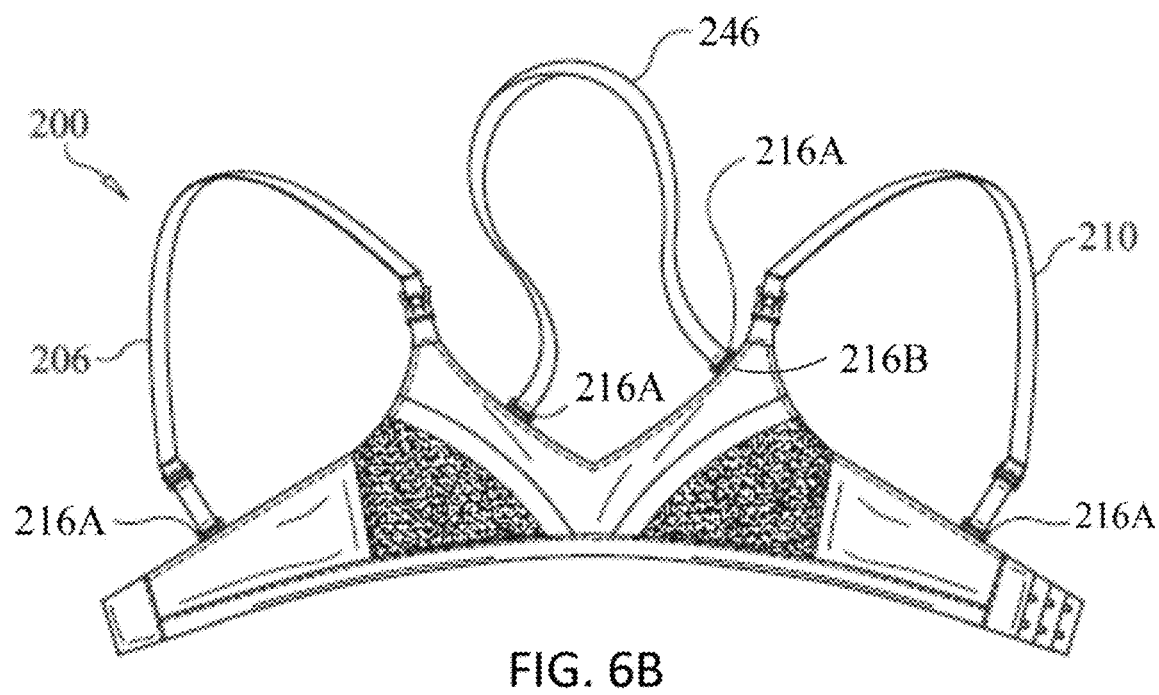
FIG. 6B is a front view of the garment of FIG. 6A illustrating an optional center or neck strap coupled to the perimeter top edge of the garment.

FIG. 6B shows garment 200 being used with a center strap 246. The strap 246 can encircle the wearer's neck with a single loop and can have hooks 216 at each end. In some embodiments, the center strap 246 can be a neck strap that is a single loop joined together (e.g., sewn together) and that has a single attachment mechanism (not shown) hook). The strap 246 may encircle the wearer's neck and then extend down from the wearer's neck toward the garment 200. In some embodiments a neck strap 246 can include a comfort portion that has a greater width at a center of the comfort portion than at the ends of the comfort portion. The center strap 246 may include a first fastening member 216A, which may be engaged with any available hole 243 of second fastening member 216B. Often times, center strap 246 may be engaged with the portion of the second fastening member 216B positioned along or coupled to the upper perimeter of the center layer 210, as shown in FIG. 6B. The center strap 246 can help to keep the garment 200 in place by providing additional stability when the wearer is pumping breast milk, particularly when a breast pump container is full of milk.

It will be appreciated that the configurations of the coupling of the first and second fastening members 216A and 216B are not limited by the examples provided by FIGS. 6A and 6B. For example, a wearer may crisscross the shoulder straps 206 such that the first fastening member 216A of the shoulder strap 206 on the right side of the garment 200 is coupled to the second fastening member 216B disposed on the wrap around panel 234 on the left side of the garment 200. Additionally, or alternatively, a wearer may position a first fastening member 216A of center strap 246 in any available hole 243 of second fastening member 216B.

FIG. 7A depicts the garment 200, showing second panel 204 and left inner layer 214, and/or a portion of center layer 210 are repositioned to expose opening 230. FIG. 7A also depicts a portion of first panel 202 pushed or moved downward to allow access to opening 230. Center layer 210 is separated from right inner layer 212 to provide a passageway for a portion of the breast pump (e.g., breast shield of breast pump body 206) through opening 230. In this fashion, the breast shield of breast pump body 296 may contact an underlying breast of a wearer to express and/or pump breast milk from the breast. Center layer 210, first panel 202, and/or right inner layer 212 may act to support a portion of the weight of the breast shield, the breast pump body 296 and/or expressed milk stored in pumping container 290, and/or assist in securing the breast shield of breast pump body 296 against the wearer's breast.

Figure 7B:
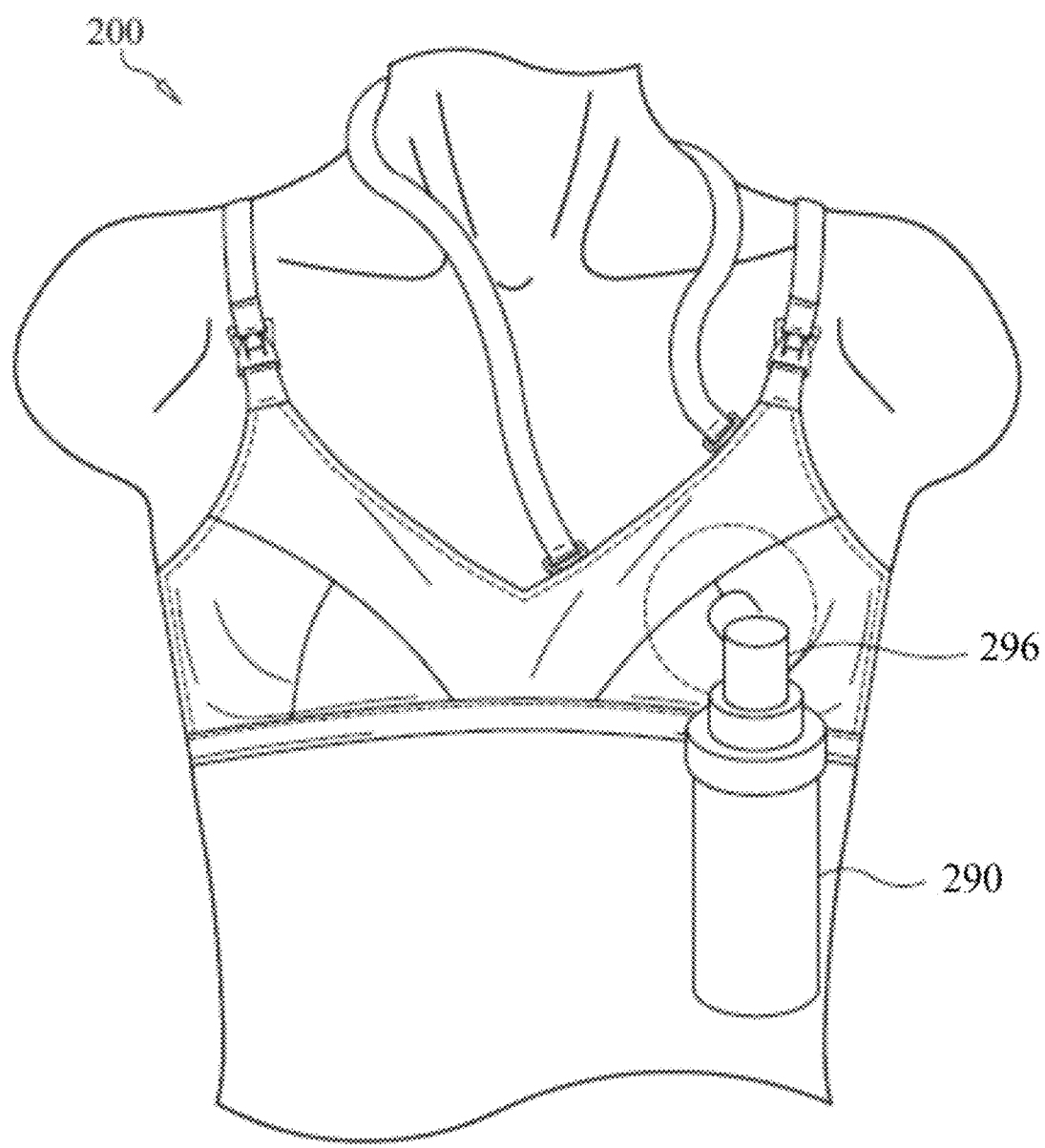

FIG. 7B depicts a wearer using a breast pump, or a portion thereof, on the first side (left side of wearer) while wearing garment 200 in a manner similar to that depicted in FIG. 7B.

FIGS. 8A-9B illustrate various views and components of a garment 300. The garment 300 can be the same or similar in structure and/or function to any of the garments described herein, such as garment 100 or garment 200. For example, the garment 300 can include an outer panel 360, an inner panel 370 (shown in FIG. 8C), and one or more support straps 380 (shown in FIG. 8E). The garment 300 can also include two shoulder straps 306. Each shoulder strap 306 can be coupled to the outer panel 360, the inner panel 370, and the support straps 380 via an engagement mechanism 350 (also referred to herein as a "clasp"). The support straps 380 can be coupled on a first end to a back panel 320 and on a second end to one of the shoulder straps 306 via the engagement mechanism 350. In alternative embodiments, the support strap 380 can be attached to a lower band of the garment 300 rather than to the back panel 320. Each of the shoulder straps 306 can have a first end coupled to the support strap 380 (via the engagement mechanism 350) and a second end coupled to the back panel 320. The outer panel 360 and/or the inner panel 370 can be attached to the back panel 320, for example, along a bottom edge of the outer panel 360 and/or along a bottom edge of the inner panel 370, via, for example, sewing/stitching. Similarly, the outer panel 360 and the inner panel 370 can be coupled together along at least a portion of a bottom edge and/or along at least a portion of a top edge of the outer panel 360 and the inner panel 370.

The inner panel 370 and the outer panel 360 can each include one or more panels each formed with one or more layers of material. As shown, for example, in FIG. 8A, the outer panel 360 includes a right outer panel 362 and a left outer panel 364. As shown, for example, in FIG. 8C, the inner panel 370 includes a right inner panel 312 and a left inner panel 314. The right inner panel 312 and the left inner panel 314 can be shaped and sized for coverage of a wearer's right breast and left breast, respectively. Each of the right inner panel 312 and the left inner panel 314 can include a first portion 315 and a second portion 317 that are coupled together such that a portion is unattached and can define an opening 330 (see FIG. 8C) between the first portion 315 and the second portion 317. In some embodiments, the first portion 315 and the second portion 317 can include an overlapping portion, which can define the opening 330. The first portion 315 and the second portion 317 can be separated by, for example, moving the first portion 315 and the second portion 317 away from each other, thereby creating the opening 330 and providing access to the user's breast. A breast pump can then be inserted through the opening 330 and the inner panel 370 can help support the breast pump during milk extraction.

Figure 8A:
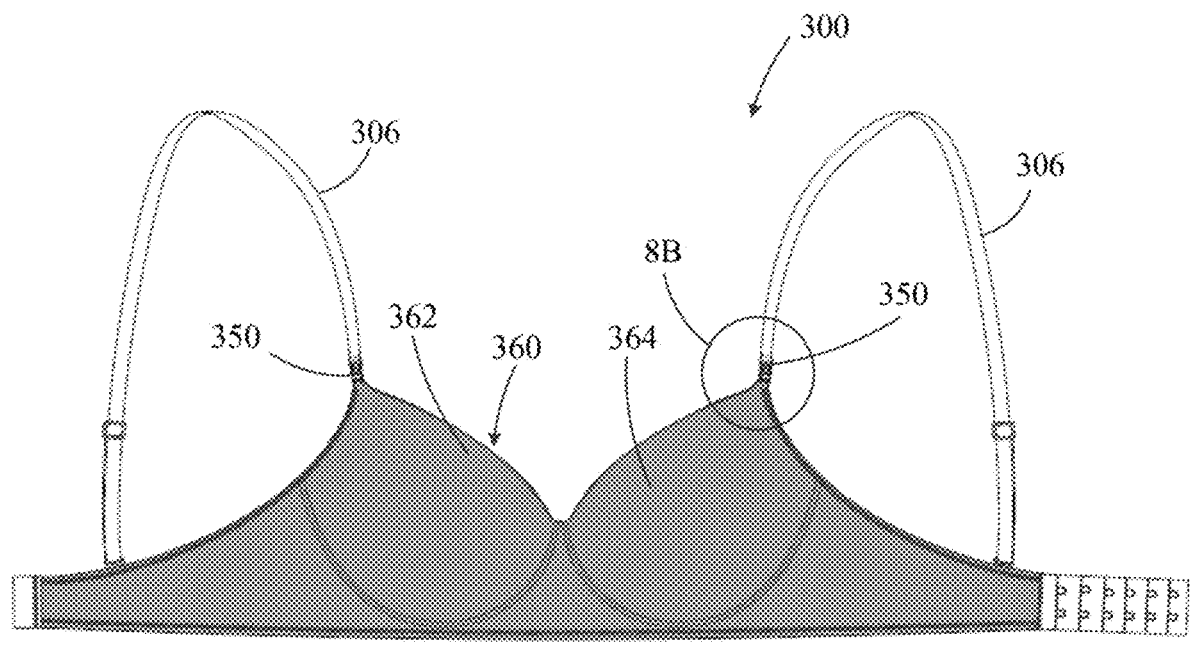
FIG. 8A is a front view of a garment, according to an embodiment.
Figure 8B:
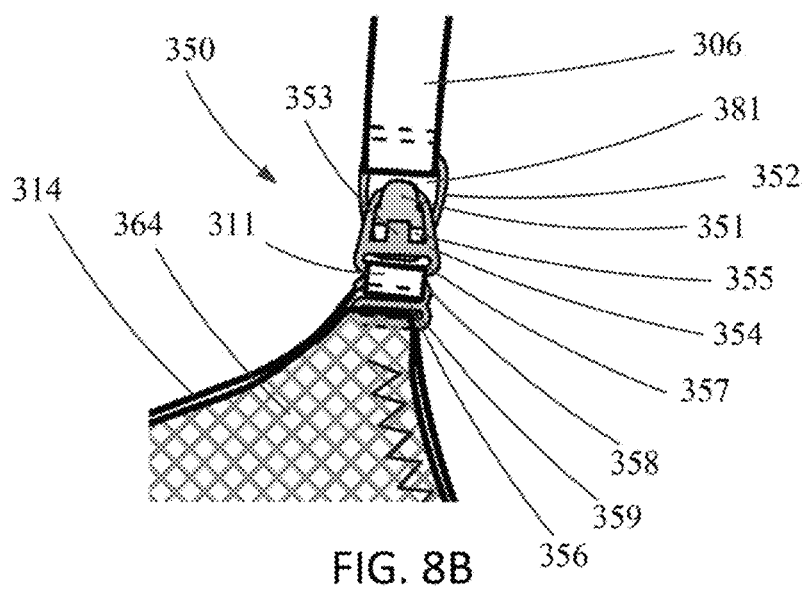
FIG. 8C is a front view of the garment of FIG. 8A shown with an outer panel removed for illustrative purposes.
FIG. 8D is an enlarged view of the region 8D of FIG. 8C.
FIG. 8E is a front view of the garment of FIG. 8A shown with the inner panel and the outer panel removed for illustrative purposes.
FIG. 8F is an enlarged view of the region 8F of FIG. 8F.
Figure 8C:
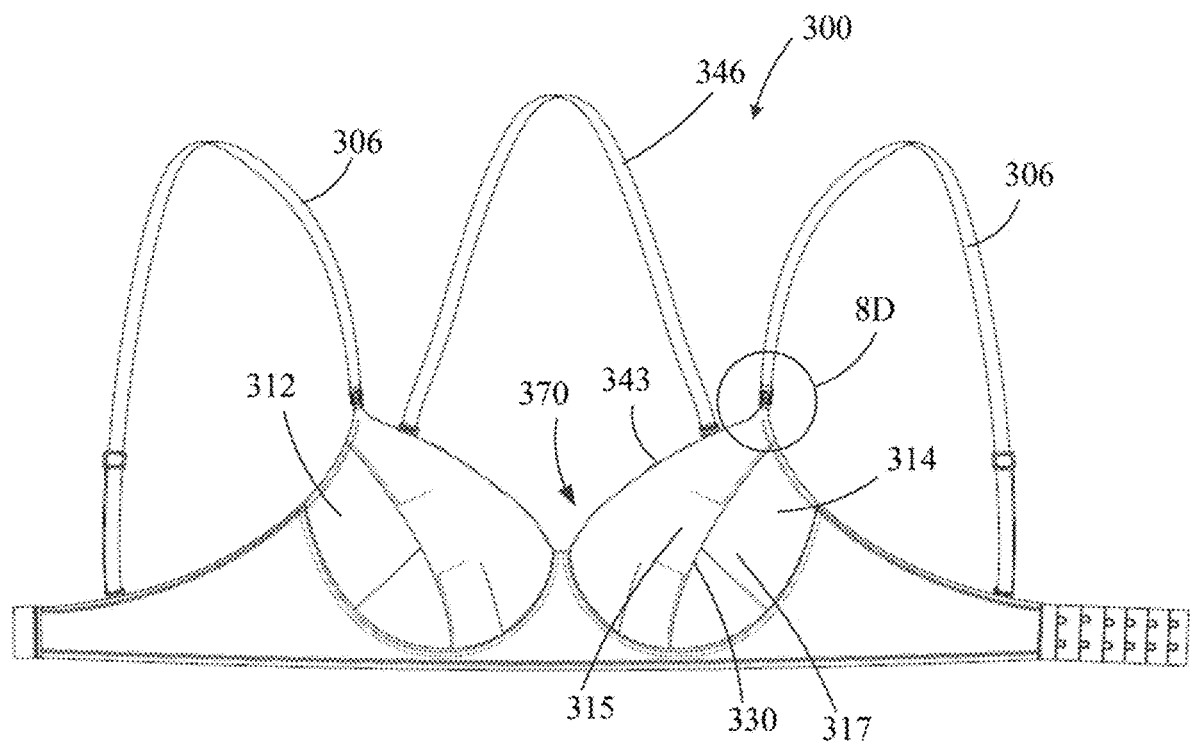

Additionally, as shown in FIG. 8C, the inner panel 370 can include one or more holes 343 defined in an upper edge of the inner panel 370. For example, in some embodiments, the inner panel 370 can define the holes 343. In some embodiments, a separate component defines the holes 343 and is coupled to the inner panel 370. The holes 343 can be the same or similar in structure and/or function to the holes 243 described above with reference to FIGS. 5A-5D. For example, a center strap 346 can be attached to the inner panel 370 via releasable engagement with any of the holes 343. The center strap 346 can be the same or similar in structure and/or function to the center strap 246 described above.

The engagement mechanism 350 can be the same or similar in structure and/or function to any of the engagement mechanisms described herein, for example, the engagement mechanisms 150 and 250 described above. As shown in FIG. 8B, which is an enlarged view of the region 8B of FIG. 8A, in this embodiment, the engagement mechanism 350 can include a first portion 352, a second portion 354, and a third portion 356. The first portion 352 can be releasably couple-able to the second portion 354, and the second portion 354 can be releasably coupleable to the third portion 356. The first portion 352 can include an extension portion 351, a first opening 381, and a second opening 383 (best shown in FIG. 8F) on an opposite side of the extension portion 351 than the first opening 381. The second portion 354 can include a tab portion 353, a first opening 355, and a second opening 357 on an opposite side of the tab portion 353 than the first opening 355. The third portion 356 can include a hook portion 358 and an opening 359. The hook portion 358 can be, fir example, an s-shaped hook similar to or the same as the fastener 216A shown in FIGS. 5C and 5D.

The first portion 352 of the engagement mechanism 350 is coupled to one of the shoulder straps 306 with, for example, stitching. For example, an end portion of one of the shoulder straps 306 can be looped through the first opening 381 and attached to itself (e.g., with stitching) such that the first portion 352 is secured within the loop of the shoulder strap 306. Additionally, the first portion 352 can be configured to receive a portion of the support strap 380 through the second opening 383 such that the support strap 380 can be secured to the first portion 352 (see, e.g., FIGS. 8E and 8F). The extension portion 351 of the first portion 352 can be shaped and sized to be inserted through the first opening 355 of the second portion 354 to releasably couple the second portion 354 to the first portion 352 and, therefore, releasably couple the inner panel 370 to the support strap 380 as described in more detail below. The tab portion 353 of the second portion 354 can be shaped and sized such that when the extension portion 351 of the first portion 352 is received through the first opening 355 of the second portion 354, the tab portion 353 contacts or engages the extension portion 351 and is flexed or clicked into locking engagement with the first portion 352 (see, e.g., FIGS. 9A and 9B which illustrate in more detail the engagement of the tab portion 353 and the extension portion 351 of the clasp 350). In some embodiments, the tab portion 353 can be sufficiently elastic such that as the second portion 354 is moved into engagement with the first portion 352, the tab portion 353 can bend slightly and then snap into locking engagement.

Figure 9B:
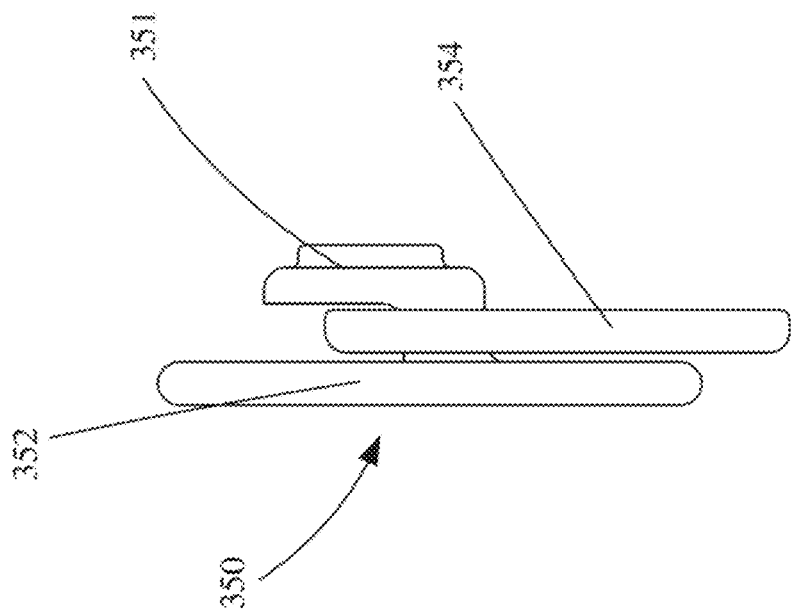
FIG. 9B is a side view of a portion of the engagement mechanism of FIG. 8A in a second configuration.
Figure 9A:
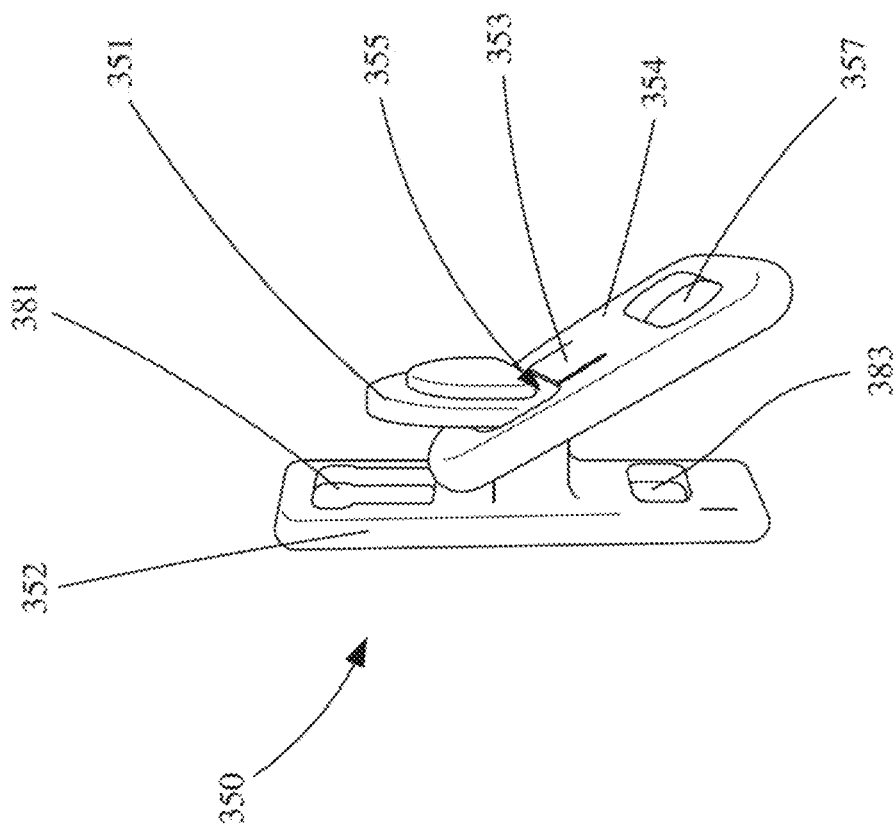
FIG. 9A is a side view of a portion of the engagement mechanism of FIG. 8A in a first configuration.

For example, FIGS. 9A and 9B are side views of the first portion 352 and the second portion 354 of the engagement mechanism 350 in a first and second configuration, respectively. As shown in FIG. 9A, the extension portion 351 of the first portion 352 can be shaped and sized such that it can be inserted through the first opening 355 of the second portion 354. As described above, the tab portion 353 of the second portion 354 can be shaped and sized such that when the extension portion 351 of the first portion 352 is received through the first opening 355 of the second portion 354, the tab portion 353 contacts or engages the extension portion 351 and can be flexed or clicked into locking engagement with the first portion 352, as shown in FIG. 9B. For example, to releasably engage the second portion 354 with the first portion 352, the extension portion 351 of the first portion 352 can be inserted through the first opening 355 of the second portion 354 as shown in FIG. 9A. Initially, the second portion 354 will be disposed at an angle relative to the first portion 352 (as shown in FIG. 9A) and as the user moves the second portion 354 toward the first portion 552, the tab portion 353 can flex past the extension portion 351 until the second portion 354 is in an abutting planar relationship with the first portion 352, as shown in FIG. 9B. The engagement between the first portion 352 and the second portion 354 can be reversed by applying a pulling force to the second portion 354 sufficient to bend the tab portion 353 past the extension portion 351 until the tab portion 353 is disengaged with the first portion 352.

In this embodiment, to secure the inner panel 370 to the second portion 354 of the clasp 350 the inner panel 370 can include a loop portion 311. More specifically, as shown, for example, In FIG. 8D, the loop portion 311 can be formed by passing a portion of the inner panel 370 through the second opening 357 of the second portion 354 of the clasp 350, folding it upon itself and stitching it to the inner panel 370. Alternatively, the loop portion 311 can be a separate component or piece of material that is inserted through the second opening 357 and secured to the inner panel 370 (e.g., with stitching), Similarly, the third portion 356 of the clasp 350 can receive a portion of the outer panel 360 within the opening 359 in the third portion 356 such that the outer panel 360 can be secured to the third portion 356 of the clasp 350 in a similar manner as described for loop 311 (e.g., a portion of the outer panel 360 being, for example, looped through the opening 359). The hook portion 358 of the third portion 356 can be inserted and secured within a channel defined by the loop portion 311 of the inner panel 370 to releasably couple the hook portion 358 to the third portion 356, and therefore, releasably couple the outer panel 370 to the inner panel 360.

As shown in FIGS. 8A and 8B and described above, the first portion 352 and the second portion 354 of the engagement mechanism 350 can be engaged to couple the inner panel 370 (e.g., right and left inner panels 312 and 314) to the support straps 380. Additionally, the third portion 356 can be coupled to the second portion 354 by inserting the hook 358 through the loop portion 311 of the inner panel 370 such that the outer panel 360 (e.g., the right and left outer panels 362 and 364) covers the inner panel 370 (e.g., the right and left inner panels 312 and 314). Although the outer panel 360 is shown as covering the entire inner panel 370 in FIG. 8A, in some embodiments, the outer panel 360 may only cover a portion of the inner panel 370. For example, in some embodiments, the outer panel 360 may cover only the cup portions of the inner panel 370.

FIG. 8C is a front view of the garment 300 shown with the outer panel 360 completely removed for illustrative purposes. Although the garment 300 is shown with the outer panel 360 completely removed, it should be understood that the outer panel 360 would remain attached to the inner panel 370 when the third portion 356 has been removed from the loop portion 311 of the inner panel 370. For example, as described above, the outer panel 360 can be attached to the inner panel 370 along a portion of a bottom edge and/or a portion of a top edge of the inner panel 370 in the regions outside of the cup regions via, for example, sewing/stitching.

Figure 8D:
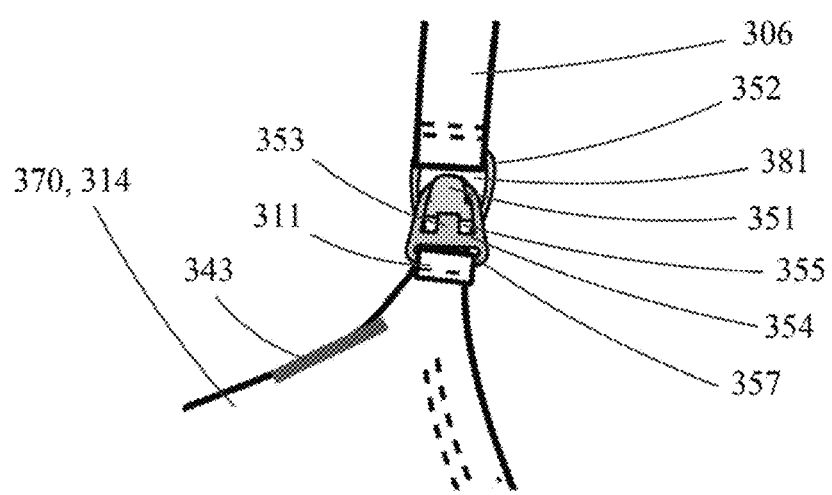

As shown in FIG. 8D, which is an enlarged view of the region SD in FIG. 8C, the outer panel 360 has been detached from the inner panel 370 by removing the third portion 356 (i.e., removing the hook portion 358) from the loop portion 311 of the inner panel 370. Thus, the inner panel 370 is exposed and accessible by the user. As shown in FIG. 8C, the removal (e.g., folding down) of the left outer panel 364 and the right outer panel 362 can reveal the left inner panel 314 and the right inner panel 312. With the outer panels 362 and/or 364 moved uncovering at least a portion of the inner panels 312 and/or 314, a user can gain access to the openings 330 to insert a breast pump as described above.

Figure 8E:
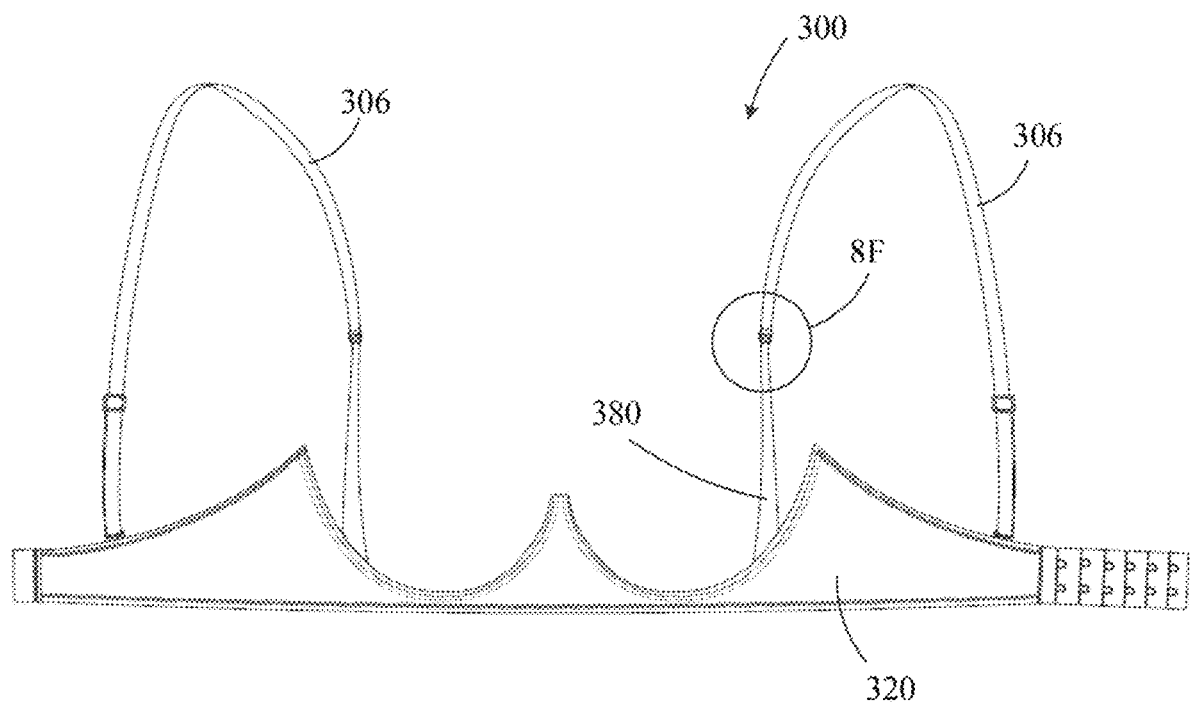
Figure 8F:
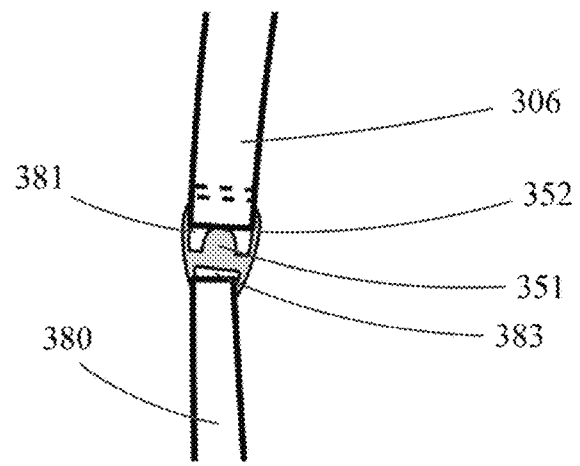

FIG. 8E is a front view of the garment 300 shown with the inner panel 370 completely removed for illustrative purposes. Thus, as shown in FIG. SF, which is an enlarged view of the region 8F in FIG. 8E, when the outer panel 360 and the inner panel 370 are both detached from the first portion 352 of the engagement mechanism 350 and from the support strap 380, the garment 300 can still be held in place on the body of the wearer via the shoulder straps 306 and support straps 380. Although the garment 300 is shown in FIG. SE with the outer panel 360 and the inner panel 370 completely removed, it should be understood that the outer panel 360 and the inner panel 370 would remain at least partially attached to the back panel 320 when the second portion 354 has been decoupled from the first portion 352 of the engagement mechanism 350. For example, as described above, the outer panel 360 and/or the inner panel 370 can be attached to the back panel 320 along the bottom edge of the outer panel 360 and/or inner panel 370 via, for example, sewing/stitching.

In use, the garment 300 can be worn by a wearer in the configuration of FIG. 8A. If access to a breast of the wearer is desired, such as for breast pumping, the outer panel 360 (e.g., the right outer panel 362 and/or the left outer panel 364) can be detached from the inner panel 370 (e.g., the right inner panel 312 and/or the left inner panel 314) by detaching or uncoupling the third portion 356 from the second portion 354 of the engagement mechanism 350 and the outer panel 360 can be moved (e.g., folded down) such that the inner panel 370 is accessible. As described above, the first portion 315 and the second portion 317 of the inner panel 370 (e.g., the right inner panel 312 and/or the left inner panel 314) can be separated (e.g., stretched or folded) to create an opening 330 through which the wearer's breast is accessible and a portion of a breast pump can be inserted. If further access to the breast of the wearer is desired, the inner panel 370 can be detached from the support strap 380 and shoulder strap 306 by removing/detaching the second portion 354 of the engagement mechanism 350 from the first portion 352 of the engagement mechanism 350. In some embodiments, the outer panel 360 and the inner panel 370 can be detached from shoulder strap 306 and support strap 380 simultaneously without removing the third portion 356 from the loop portion 311 of the inner panel 370. When desired, the inner panel 370 and the outer panel 360 can be reattached to shoulder strap 306 and support strap 380 by recoupling the second portion 354 to the first portion 352 of the engagement mechanism, and recoupling the third portion 356 of the engagement mechanism 350 to the loop portion 311 of the inner panel 370.

FIGS. 10 and 11A-11C show various views and components of a garment 400. The garment 400 can be the same or similar in structure and function to the garment 300 shown in FIGS. 8A-9B and described above. For example, the garment 400 can include an outer panel 460 with a right outer panel 462 and a left outer panel 464, an inner panel 470 (shown in FIG. 11B) with a right inner panel (not shown) and a left inner panel 414 (shown in FIGS. 11B and 11C), a support strap 480 (shown in FIG. 11C) and a back panel 420. The garment 400 can include two shoulder straps 406. Each shoulder strap 406 can be coupled to the outer panel 460, the inner panel 470, and the support strap 480 via an engagement mechanism 450 (also referred to herein as a "clasp") as described for the previous embodiment.

Figure 11A:
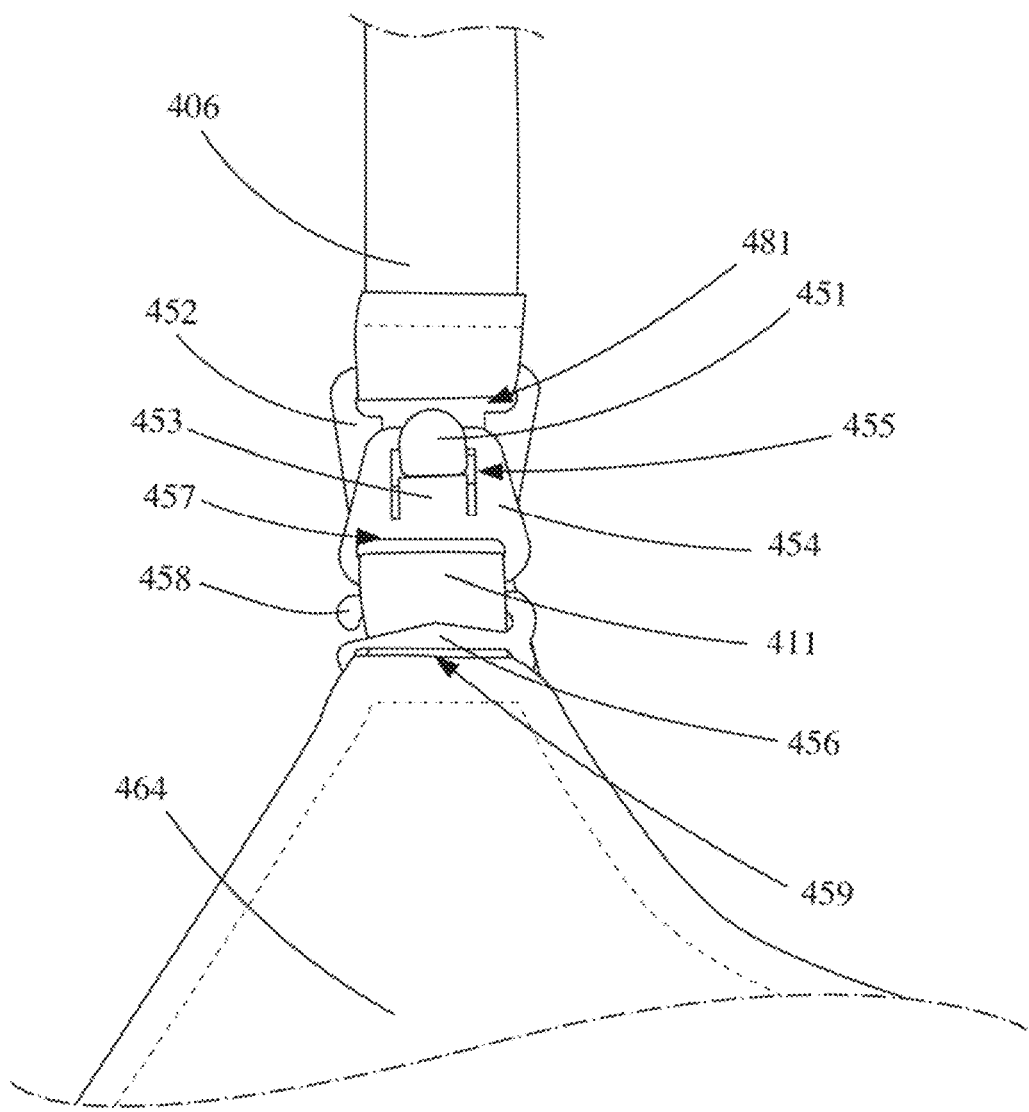
FIG. 11A is a front view of a portion of the garment of FIG. 10, with an engagement mechanism shown in a first configuration in which the outer panel is coupled to the inner panel and the inner panel is coupled to the shoulder strap.

The engagement mechanism 450 can be the same or similar in structure and/or function to any of the engagement mechanisms described herein, such as engagement mechanism 350. As shown in FIG. 11A, which is a front view of a portion of the garment 400, the engagement mechanism 450 can include a first portion 452, a second portion 454, and a third portion 456. The first portion 452 can be releasably engageable with the second portion 454, and the second portion 454 can be releasably coupleable to the third portion 456. The first portion 452 can include an extension portion 451, a first opening 481, and a second opening 483 (best shown in FIG. 11C) on an opposite side of the extension portion 451 than the first opening 481. The second portion 454 can include a tab portion 453, a first opening 455, and a second opening 457 on an opposite side of the tab portion 453 than the first opening 455. The third portion 456 can include a hook portion 458 and an opening 459. The hook portion 458 can be, for example, an s-shaped hook similar to or the same as the fastener 216A shown in FIGS. 5C and 5D.

The first portion 452 of the engagement mechanism 450 is coupled to one of the shoulder straps 406, with for example, stitching. For example, an end portion of one of the shoulder straps 406 can be looped through the first opening 481 and attached to itself such that the first portion 452 is secured within the loop of the shoulder strap 406. Additionally, the first portion 452 can be configured to receive a portion of the support strap 480 through the second opening 483 such that the support strap 480 can be secured to the first portion 452 (see, e.g., FIG. 11C). The extension portion 451 of the first portion 452 can be shaped and sized to be inserted through the first opening 455 of the second portion 454 to releasably couple the second portion 454 to the first portion 452, and therefore, releasably couple the inner panel 460 to the support strap 480 similarly as described above with reference to FIGS. 9A and 9B. The tab portion 453 of the second portion 454 can be shaped and sized such that when the extension portion 451 of the first portion 452 is received through the first opening 455 of the second portion 454, the tab portion 453 contacts or engages the extension portion 451 and is flexed or clicked into locking engagement with the first portion 452. In some embodiments, the tab portion 453 can be sufficiently elastic such that as the second portion 454 is moved into engagement with the first portion 452, the tab portion 453 can bend slightly and then snap into locking engagement.

As with the previous embodiment, in this embodiment, to secure the inner panel 470 to the second portion 454 of the clasp 450, the inner panel 470 can include a loop portion 411. More specifically, as shown, for example, in FIG. 11C, the loop portion 411 can be formed by passing a portion of the inner panel 470 through the second opening 457 of the second portion 454 of the clasp 450, folding it upon itself and stitching it to the inner panel 470. Alternatively, the loop portion 411 can be a separate component or piece of material that is inserted through the second opening 457 and secured to the inner panel 470 (e.g., with stitching). Similarly, the third portion 456 of the clasp 450 can receive a portion of the outer panel 460 within the opening 459 in the third portion 456 such that the outer panel 460 can be secured to the third portion 456 of the clasp 450 in a similar manner as described for loop 411 (e.g., a portion of the outer panel 460 being, for example, looped through the opening 459). The hook portion 458 of the third portion 456 can be inserted and secured within a channel defined by the loop portion 411 of the inner panel 470 to releasably couple the hook portion 458 to the third portion 456, and therefore, releasably couple the outer panel 370 to the inner panel 360.

As shown in FIG. 11A and described above, the first portion 452 and the second portion 452 of the engagement mechanism 450 can be engaged such that the inner panel 470 is coupled to the support strap 480. Additionally, the third portion 456 can be coupled to the second portion 454 via the loop portion 411 of the inner panel 470 such that the outer panel 460 covers at least a portion of the inner panel 470. Although the outer panel 460 is shown as covering the entire inner panel 470 in FIG. 10, in some embodiments, the outer panel 460 can cover only a portion of the inner panel 470. For example, in some embodiments, the outer panel 460 can cover only the cup portions of the inner panel 470.

Figure 11B:
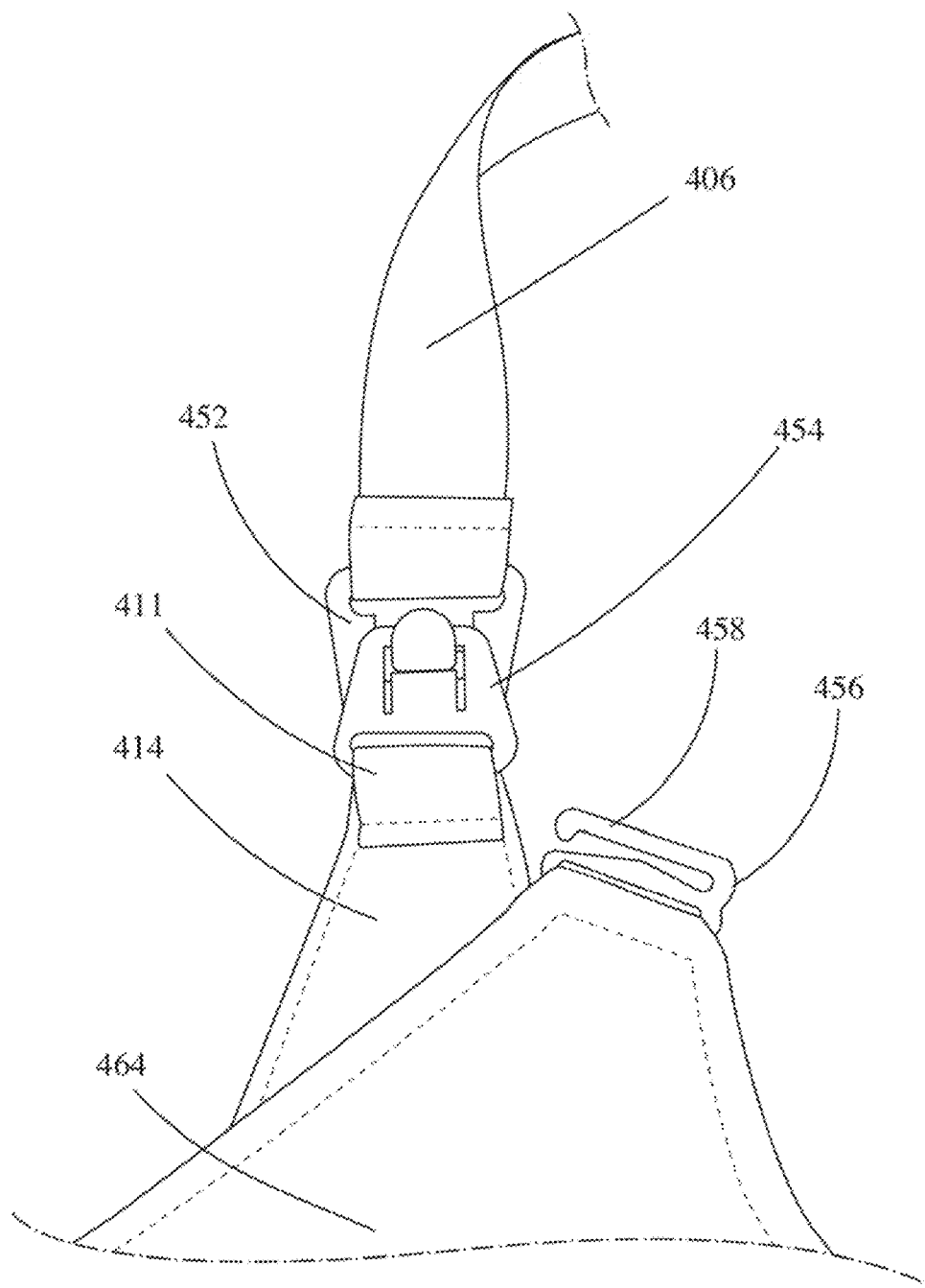
FIG. 11B is a front view a portion of the garment of FIG. 10, with the engagement mechanism shown in a second configuration in which the outer panel is decoupled from the inner panel.

FIG. 11B is a front view of a portion of the garment 400 shown with the outer panel 460 and the third portion 456 of the engagement mechanism 450 detached from the inner panel 470. Specifically, the outer panel 460 has been detached from the inner panel 470 via removing the third portion 456 (i.e., removing the hook portion 358) from the loop portion 411 of the inner panel 470. Thus, by moving (e.g., folding down) the outer panel 460, the inner panel 470 can be revealed, providing access to a user to openings (not shown) defined by the inner panel 470 as described above for previous embodiments.

Figure 11C:
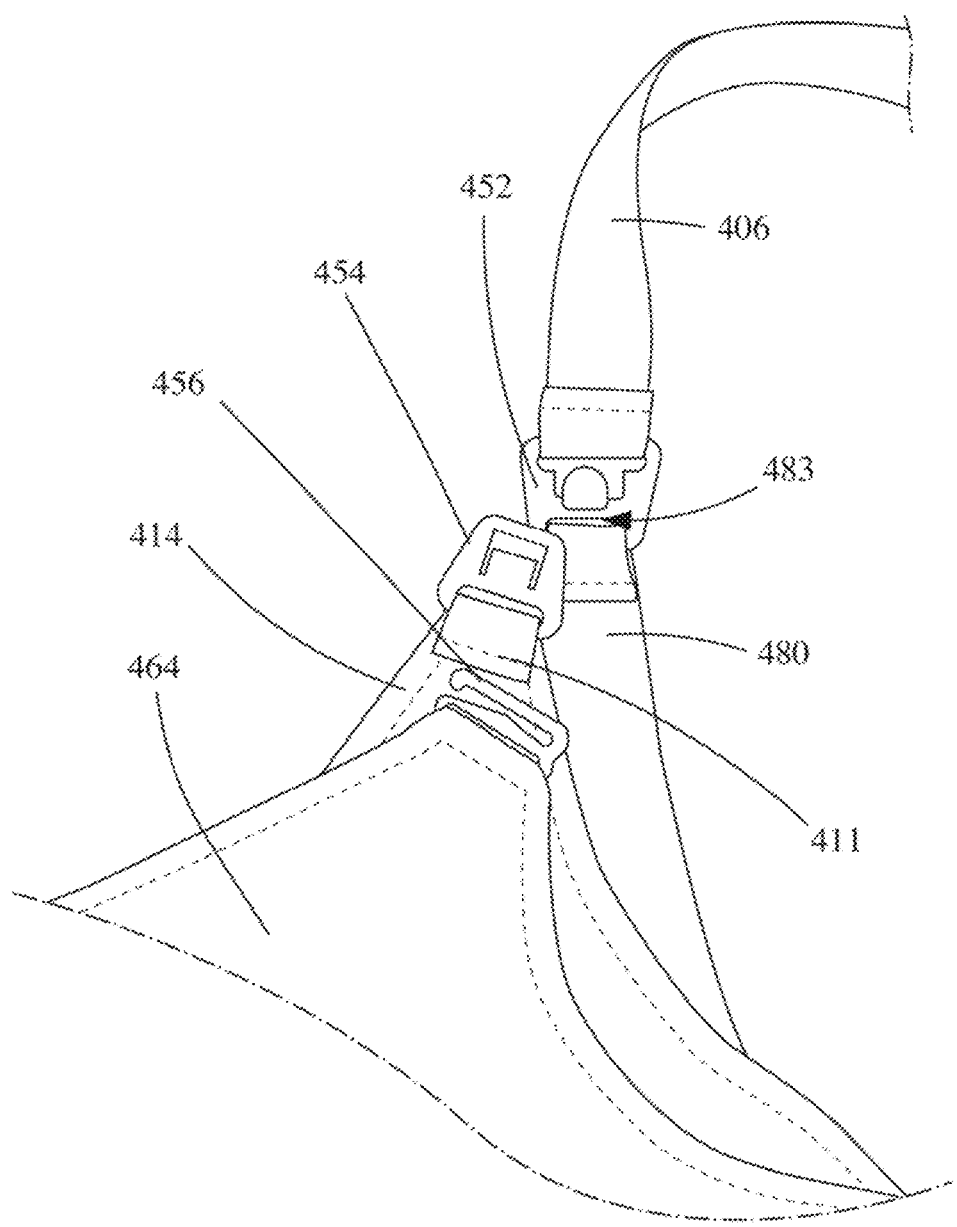
FIG. 11C is a front view of a portion of the garment of FIG. 10, with the engagement mechanism shown in a third configuration in which the outer panel is decoupled from the inner panel and the inner panel is decoupled from the shoulder strap.

FIG. 11C is a front view of a portion of the garment 400 shown with the inner panel 470 and the second portion 454 detached from the first portion 452. Each of the shoulder straps 406 can be attached to a hack panel (not shown) of the garment 400 and to the support strap 480 as described for garment 300. Thus, as shown in FIG. 11C, when the outer panel 460 and the inner panel 470 are both detached from the first portion 452 of the engagement mechanism 450 and the support strap 480, the garment 400 can still be held in place on the body of the wearer via the shoulder straps 406 and support straps 380.

In use, when the garment 400 is worn by a wearer, to gain access to a breast of the wearer to, for example, extract milk using a breast pump, the outer panel 460 can be detached from the inner panel 470 by unhooking the hook portion 458 from the loop portion 411, and the outer panel 460 can be moved (e.g., folded down) such that the inner panel 470 is accessible. If further access to the breast of the wearer is desired, the inner panel 470 can be detached from the support strap 480 and the shoulder strap 406 by removing the second portion 454 of the engagement mechanism 450 from the first portion 452 of the engagement mechanism 450. In some embodiments, the outer panel 460 and the inner panel 470 can be detached from the shoulder strap 406 and support strap 480 simultaneously without removing the third portion 456 of the engagement mechanism 450 from the loop portion 411 of the inner panel 470. When desired, the inner panel 470 and the outer panel 460 can be reattached to the shoulder strap 406 and support strap 480 by recoupling the first portion 452 of the engagement mechanism 450 to the second portion 454 of the engagement mechanism 450, and recoupling the first portion 452 to the loop portion 411 of the inner panel 470.

Figure 12A:
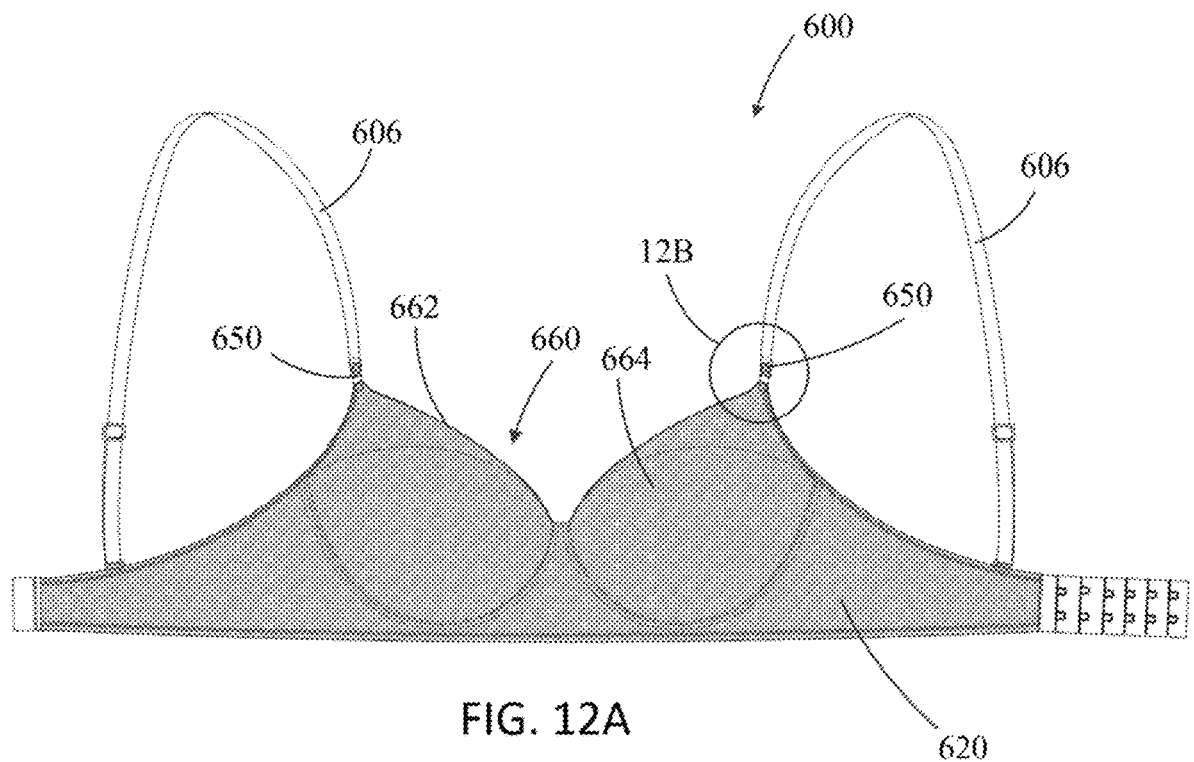
FIG. 12A is a front view of a garment, according to an embodiment.

FIGS. 12A-12F illustrate various views and components of a garment 600. FIG. 12A is a front view of the garment 600 in a first configuration. The garment 600 can be the same or similar in structure and/or function to any of the garments described herein, such as the garment 100 or the garment 300. For example, the garment 600 can include an outer panel 660, an inner panel 670 (shown in FIG. 12C), and a support strap 680 (shown in FIG. 12E). The garment 600 can include two shoulder straps 606. Each shoulder strap 606 can be coupled to the outer panel 660, the inner panel 670, and the support strap 680 via an engagement mechanism 650 (also referred to herein as a "clasp").

The support straps 680 can be coupled on a first end to a back panel 620 and on a second end to one of the shoulder straps 606 via the engagement mechanism 650. In alternative embodiments, the support strap 680 can be attached to a lower band of the garment 600 rather than to the back panel 620. Each of the shoulder straps 606 can have a first end coupled to the support strap 680 (via the engagement mechanism 650) and a second end coupled to the hack panel 620. The outer panel 660 and/or the inner panel 670 can be attached to the back panel 620, for example, along a bottom edge of the outer panel 660 and/or along a bottom edge of the inner panel 670, via, for example, sewing/stitching. Similarly, the outer panel 660 and the inner panel 670 can be coupled together along at least a portion of a bottom edge and/or along at least a portion of a top edge of the outer panel 660 and the inner panel 670.

The inner panel 670 and the outer panel 660 can each include one or more panels each formed with one or more layers of material. As shown, for example, in FIG. 12A, the outer panel 660 includes a right outer panel 662 and a left outer panel 664. As shown, for example, in FIG. 12C, the inner panel 670 includes a right inner panel 612 and a left inner panel 614. The right inner panel 612 and the left inner panel 614 can be shaped and sized for coverage of a wearer's right breast and left breast, respectively. Each of the right inner panel 612 and the left inner panel 614 can include a first portion 615 and a second portion 617 that are coupled together such that a portion is unattached and can define an opening 630 (see FIG. 12C) between the first portion 615 and the second portion 617. In some embodiments, the first portion 615 and the second portion 617 can include an overlapping portion which can define the opening 630. The first portion 615 and the second portion 617 can be separated by, for example, moving the first portion 615 and the second portion 617 away from each other, thereby creating the opening 630 and providing access to the user's breast. A breast pump can then be inserted through the opening 630 and the inner panel 670 can help support the breast pump during milk extraction.

Figure 12B:
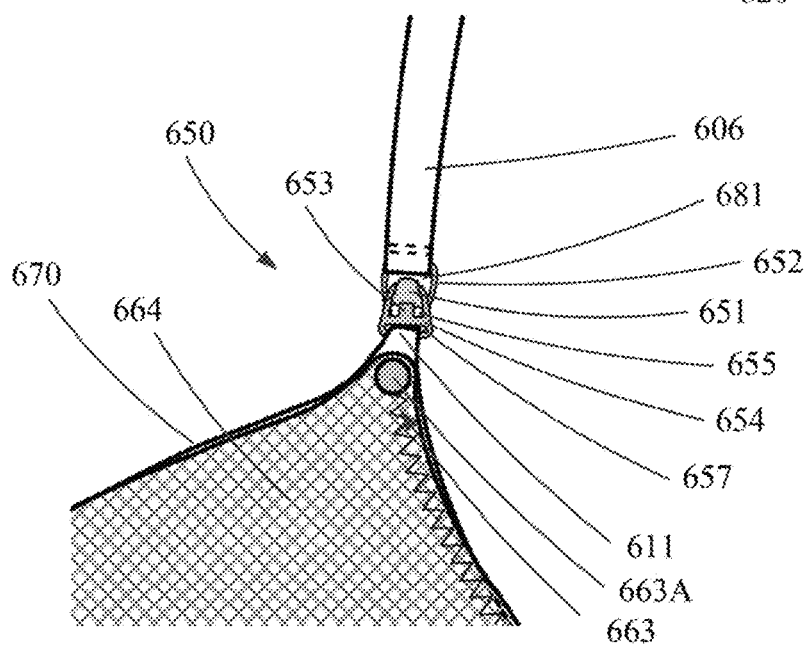
FIG. 12B is an enlarged view of the region 12B of FIG. 12A.
Figure 12C:
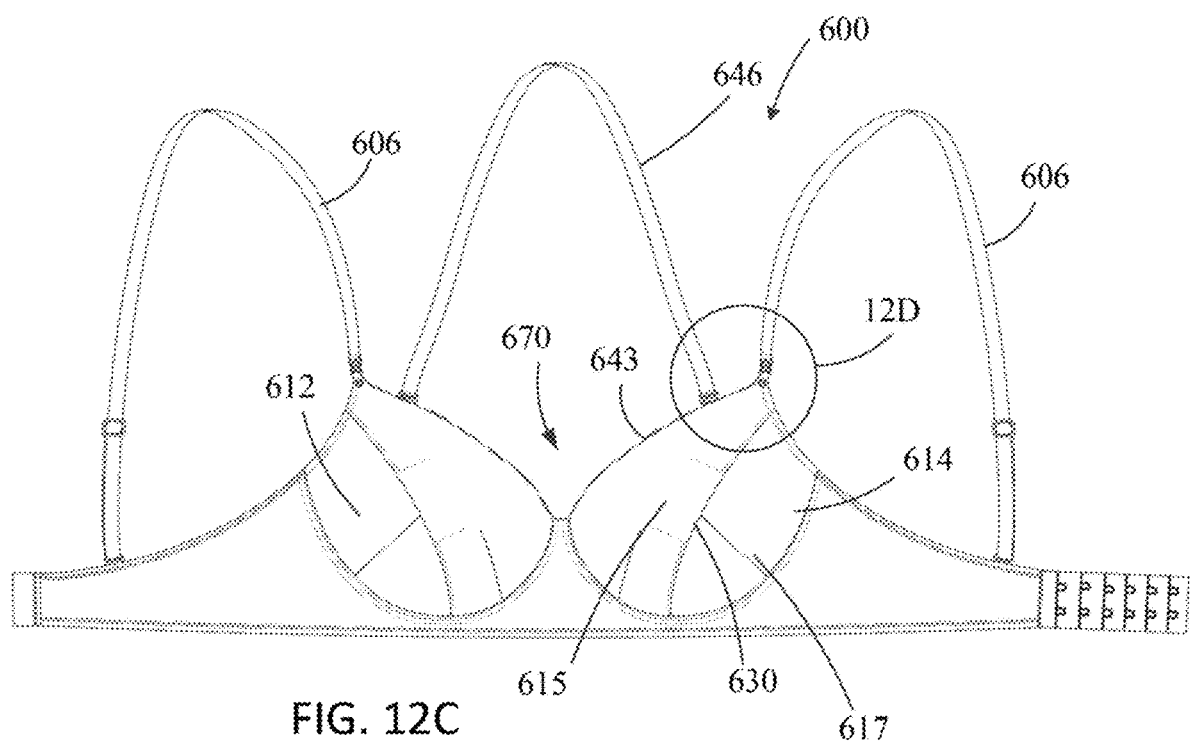
FIG. 12C is a front view of the garment of FIG. 12A shown with the outer panel removed for illustrative purposes.
Figure 12D:
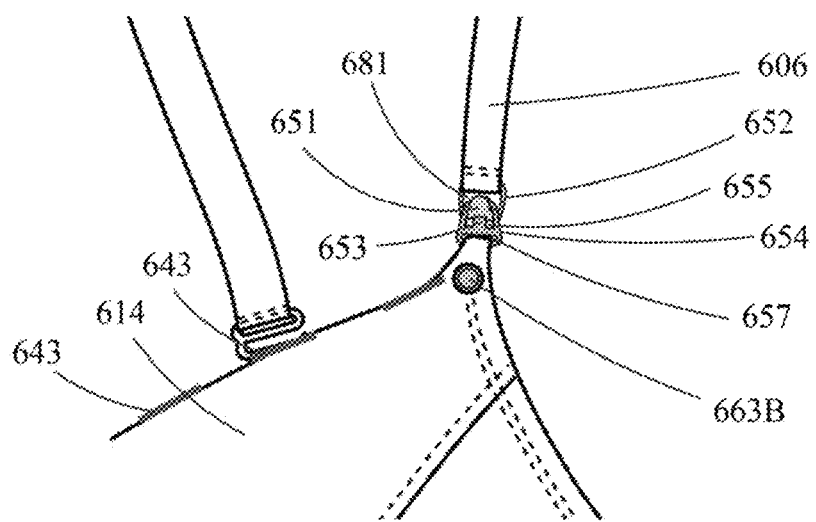
FIG. 12D is an enlarged view of the region 12D of FIG. 12C.

Additionally, as shown in FIGS. 12C and 12D, the inner panel 670 can include one or more holes 643 defined in an upper edge of the inner panel 670. For example, in some embodiments, the inner panel 670 can define the holes 643 and/or the holes 643 can be defined by a separate component coupled to the inner panel 670. As described for previous embodiments, a center strap 646 can be attached to the inner panel 670 via selective releasable engagement with any of the holes 643. The center strap 646 can be the same or similar in structure and/or function to the center strap 246 described above.

The engagement mechanism 650 can be the same or similar in structure and/or function to any of the engagement mechanisms described herein, such as engagement mechanism 250 and/or engagement mechanism 350. As shown in FIG. 12B, which is an enlarged view of the region 12B of FIG. 12A, in this embodiment, the engagement mechanism 650 includes a first portion 652 and a second portion 654. The first portion 652 can be releasably engageable with the second portion 654 in the same manner as described above for engagement mechanism 350. In this embodiment, the outer panel 660 can be releasably coupled to the inner panel with a snap coupling 663. The snap coupler 663 can be configured to releasably couple a portion of the outer panel 660 to a portion of the inner panel 670 as described in more detail below. The first portion 652 of the engagement mechanism 650 can include an extension portion 651, a first opening 681, and a second opening 683 (best shown in FIG. 12F) on an opposite side of the extension portion 651 than the first opening 681. The second portion 654 of the engagement mechanism 650 can include a tab portion 653, a first opening 655, and a second opening 657 on an opposite side of the tab portion 653 than the first opening 655. The snap coupler 663 can include a snap feature. For example, in some embodiments, the snap coupler 663 can include a first snap feature 663A secured to the outer panel 660 and a second complementary snap feature 663B secured to the inner panel 670.

The first portion 652 of the engagement mechanism 650 is coupled to one of the shoulder straps 606 with, for example, stitching in the same manner as described above for engagement mechanism 650. For example, an end portion of one of the shoulder straps 606 can be looped through the first opening 681 and attached to itself such that the first portion 652 is secured within the loop of the shoulder strap 606. Additionally, the first portion 652 of the engagement mechanism 650 can receive a portion of the support strap 680 through the second opening 683 such that the support strap 680 can be secured to the first portion 652 (see, e.g., FIGS. 12E and 12F). The extension portion 651 of the first portion 652 can be shaped and sized to be inserted through the first opening 655 of the second portion 654 to releasably couple the second portion 654 to the first portion 652 and, therefore, releasably couple the inner panel 670 to the support strap 680 similarly as described above with reference to FIGS. 9A and 9B. The tab portion 653 of the second portion 654 can be shaped and sized such that, when the extension portion 651 of the first portion 652 is received through the first opening 655 of the second portion 654, the tab portion 653 contacts or engages the extension portion 651 and is flexed or clicked into locking engagement with the first portion 652. In some embodiments, the tab portion 653 can be sufficiently elastic such that as the second portion 654 is moved into engagement with the first portion 652, the tab portion 653 can bend slightly and then snap into locking engagement.

In this embodiment, to secure the inner panel 670 to the second portion 654 of the clasp 650, the inner panel 670 can include a loop portion 611. More specifically, as shown, for example. In FIG. 12D, the loop portion 611 can be formed by passing a portion of the inner panel 670 through the second opening 657 of the second portion 654 of the clasp 650, folding it upon itself and stitching it to the inner panel 670. Alternatively, the loop portion 611 can be a separate component or piece of material that is inserted through the second opening 657 and secured to the inner panel 670 (e.g., with stitching).

As shown in FIGS. 12A and 12B and described above, the first portion 652 and the second portion 654 of the engagement mechanism 650 can be engaged to releasably couple the inner panel 670 (e.g., right inner panel 612 and left inner panel 614) to the support straps 680. Additionally, the snap coupler 663 can releasably couple the outer panel 660 (e.g., the right outer panel 662 and the left outer panel 664) to the inner panel 670 (e.g., right inner panel 612 and left inner panel 614) such that the outer panel 660 substantially covers the inner panel 670 by coupling the first snap feature 663A secured to the outer panel 660 with the second complementary snap feature 663B secured to the inner panel 670. Although the outer panel 660 is shown as covering the entire inner panel 670 in FIG. 12A, in some embodiments, the outer panel 660 can only cover a portion of the inner panel 670. For example, in some embodiments, the outer panel 660 can cover only the cup portions of the inner panel 670.

FIG. 12C is a front view of the garment 600 shown with the outer panel 660 completely removed for illustrative purposes. Although the garment 600 is shown with the outer panel 660 completely removed, it should be understood that the outer panel 660 would remain attached to the inner panel 670 when the first snap feature 663A of the outer panel 660 has been decoupled from the second snap feature 663B of the inner panel 670. For example, as described above, the outer panel 660 can be attached to the inner panel 670 along a portion of the upper edges and/or along a portion of the bottom edges of the inner panel 670 in the regions outside of the cup regions via, for example, sewing/stitching.

As shown in FIG. 12D, which is an enlarged view of the region 12D in FIG. 12C, the left outer panel 664 has been detached from the left inner panel 6614 by removing (i.e., unsnapping) the first snap feature 663A of the outer panel left outer panel 664 from the second snap feature 663B of the left inner panel 614. Thus, the left inner panel 614 is exposed and accessible by the user. As shown in FIG. 12C, detaching and moving (e.g., folding down) the outer panels 662 and 664 can reveal the right inner panel 612 and the left inner panel 614. With the outer panels 662 and/or 664 moved uncovering at least a portion of the inner panels 612 and/or 614, a user can gain access to the openings 630 to insert a breast pump as described above.

Figure 12E:
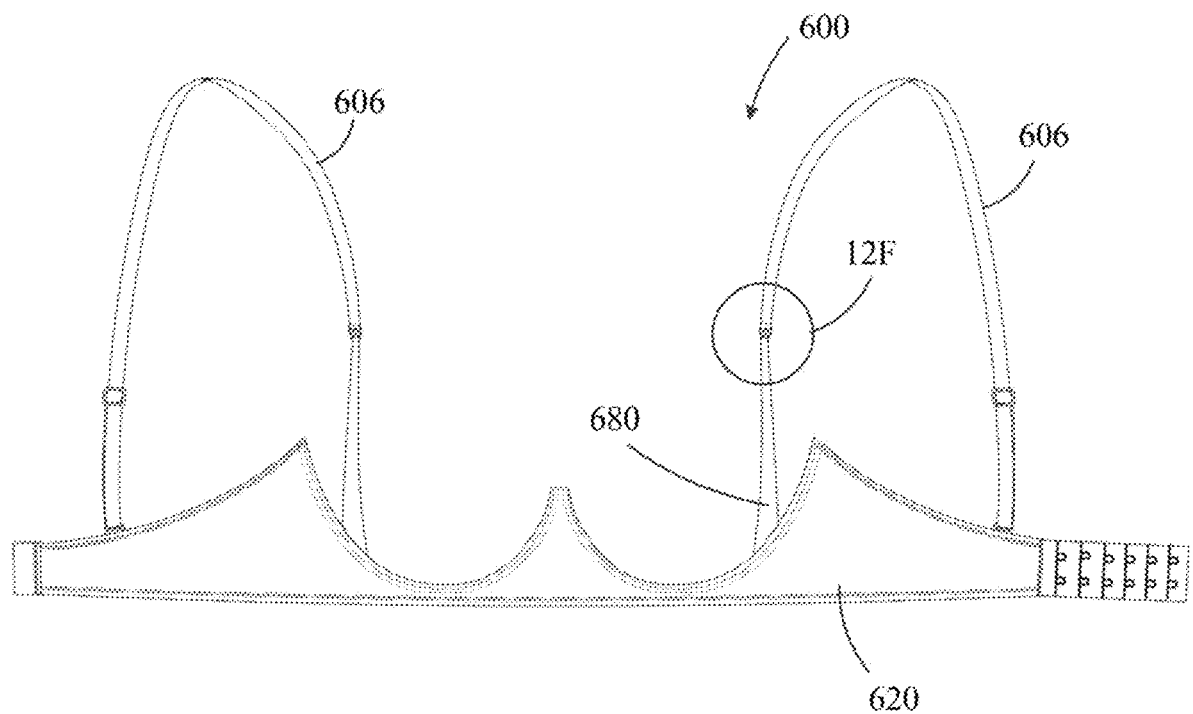
FIG. 12E is a from view of the garment of FIG. 12A shown with the inner panel and the outer panel removed for illustrative purposes.
Figure 12F:
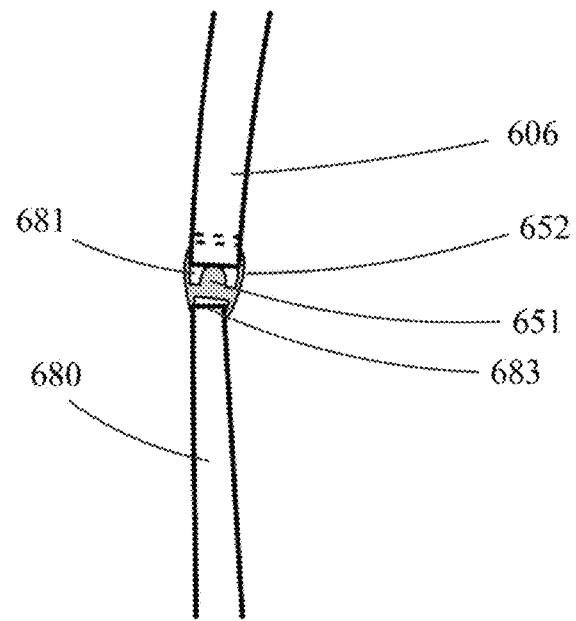
FIG. 12F is an enlarged view of the region 12F of FIG. 12F.

FIG. 12E is a front view of the garment 600 shown with the inner panel 670 completely removed for illustrative purposes. Thus, as shown in FIG. 12F, which is an enlarged view of the region 12F in FIG. 12E, when the outer panel 660 and the inner panel 670 are both detached from the support strap 680, the garment 600 can still be held in place on the body of the wearer via the shoulder straps 606 and support straps 680. Although the garment 600 is shown in FIG. 12E with the outer panel 660 and the inner panel 670 completely removed, it should be understood that the outer panel 660 and the inner panel 670 would remain at least partially attached to the back panel 620 when the second portion 654 has been decoupled from the first portion 652 of the engagement mechanism 650 and the outer panel 660 is detached from the inner panel 670. For example, as described above, the outer panel 660 and/or the inner panel 670 can be attached to the back panel 620 along the bottom edge of the outer panel 660 and/or inner panel 670 via, for example, sewing/stitching.

In use, the garment 600 can be worn by a wearer and if access to a breast of the wearer is desired, such as for breast pumping, the first snap feature 663A can be detached from the second snap feature 663B such that the outer panel 660 (right outer panel 662 and/or left outer panel 664) can be moved (e.g., folded down) relative to the inner panel 670 and such that the inner panel 670 is accessible. The first portion 615 and the second portion 617 of the inner panel 670 (e.g., the right inner panel 612 and/or the left inner panel 614) can be separated (e.g., stretched or folded) to create an opening such that the wearer's breast is accessible through the opening 630. If further access to the breast of the wearer is desired, the inner panel 670 can be detached from the support strap 680 and shoulder strap 606 by removing the second portion 654 of the engagement mechanism 650 from the first portion 652 of the engagement mechanism 650. When desired, the inner panel 670 and the outer panel 660 can be reattached to the support strap 680 and the shoulder strap 606 by recoupling the second portion 654 to the first portion 652, and recoupling the first snap portion 663A to the second snap portion 663B.

FIGS. 13A-13F illustrate various views and components of a garment 700. The garment 700 can be the same or similar in structure and/or function to any of the garments described herein, such as the garment 100 or the garment 600. For example, the garment 700 can include an outer panel 760, an inner panel 770 (shown in FIG. 13C), and a support strap 780 (shown in FIG. 13E). The garment 700 can include two shoulder straps 706. Each shoulder strap 706 can be coupled to the outer panel 760, the inner panel 770, and the support strap 780 via an engagement mechanism 750 (also referred to herein as a "clasp").

The support straps 780 can be coupled on a first end to a back panel 720 and on a second end to one of the shoulder straps 606 via the engagement mechanism 750. In alternative embodiments, the support strap 780 can be attached to a lower band of the garment 700 rather than to the back panel 720. Each of the shoulder straps 706 can have a first end coupled to the support strap 780 (via the engagement mechanism 750) and a second end coupled to the back panel 720. The outer panel 760 and/or the inner panel 770 can be attached to the back panel 720, for example, along a bottom edge of the outer panel 760 and/or along a bottom edge of the inner panel 770, via, for example, sewing/stitching. Similarly, the outer panel 760 and the inner panel 770 can be coupled together along at least a portion of a bottom edge and/or along at least a portion of a top edge of the outer panel 760 and the inner panel 770.

The inner panel 770 and the outer panel 760 can each include one or more panels each formed with one or more layers of material. As shown, for example, in FIG. 13A, the outer panel 760 includes a right outer panel 762 and a left outer panel 764. As shown, for example, in FIG. 13C, the inner panel 770 includes a right inner panel 712 and a left inner panel 714. The right inner panel 712 and the left inner panel 714 can be shaped and sized for coverage of a wearer's right breast and left breast, respectively. Each of the right inner panel 712 and the left inner panel 714 can include a first portion 715 and a second portion 717 that are coupled together such that a portion is unattached and can define an opening 730 (see FIG. 13C) between the first portion 715 and the second portion 717. In some embodiments, the first portion 715 and the second portion 717 can include an overlapping portion which can define the opening 730. The first portion 715 and the second portion 717 can be separated by, for example, moving the first portion 715 and the second portion 717 away from each other, thereby creating the opening 730 and providing access to the user's breast. A breast pump can then be inserted through the opening 730 and the inner panel 770 can help support the breast pump during milk extraction.

Figure 13A:
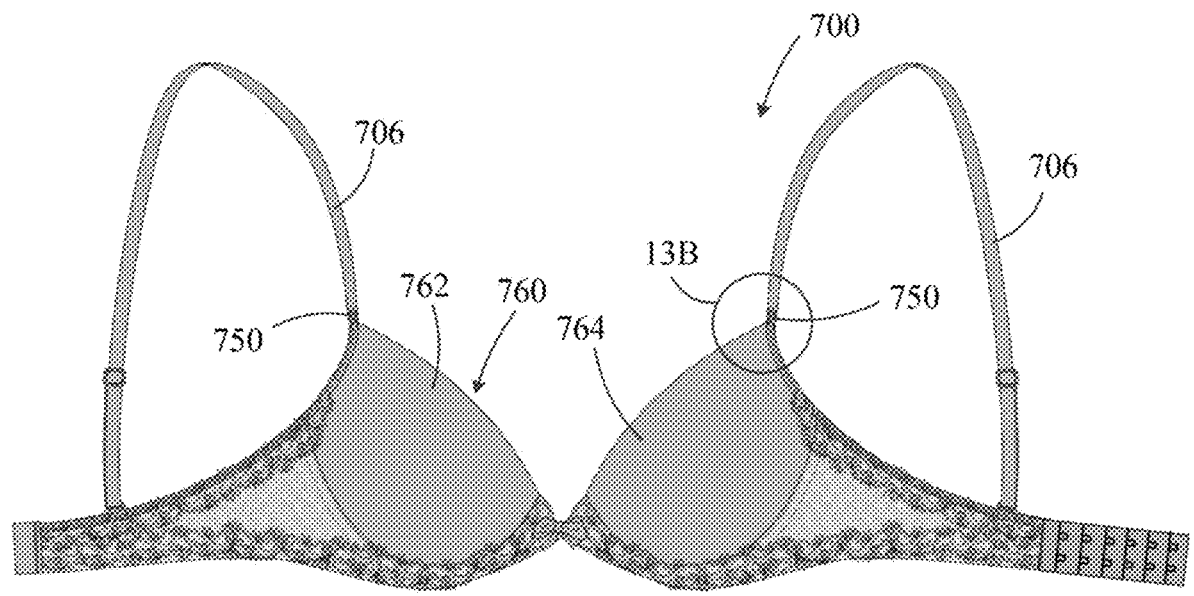
FIG. 13A is a front view of a garment, according to an embodiment.
Figure 13B:
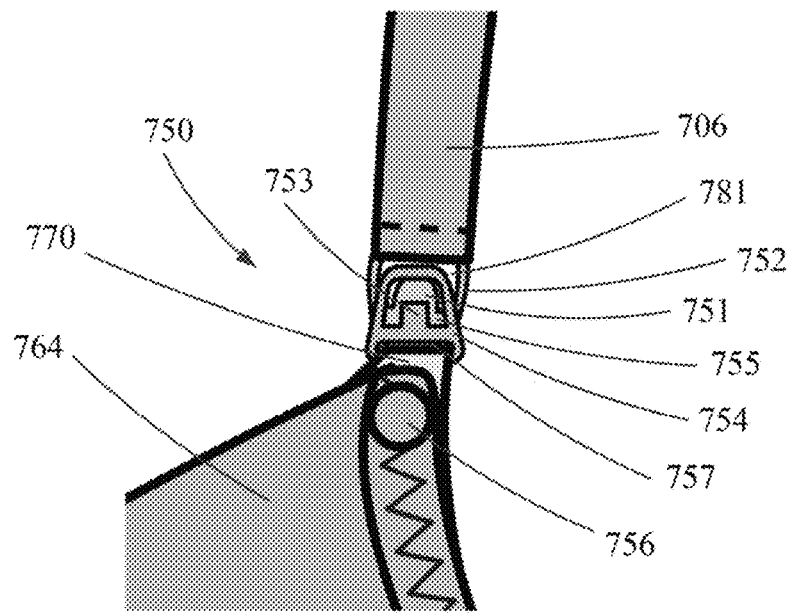
FIG. 13B is an enlarged view of the region 13B of FIG. 13A.
Figure 13C:
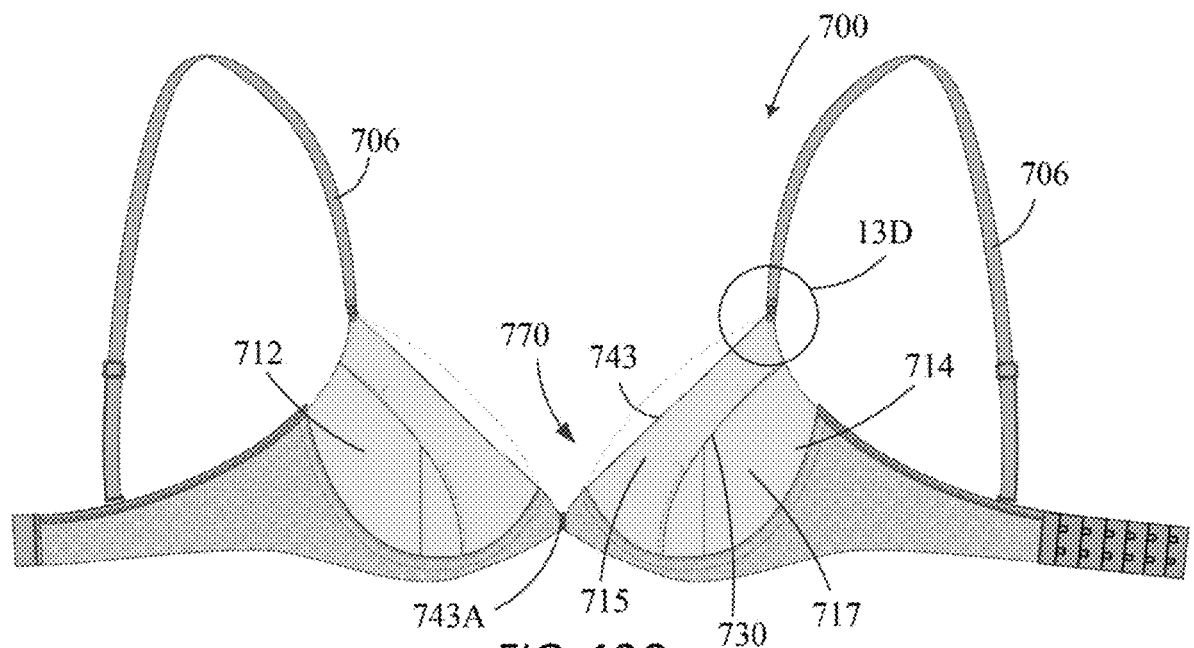
FIG. 13C is a front view of the garment of FIG. 13A shown with an outer panel removed for illustrative purposes.
Figure 13D:
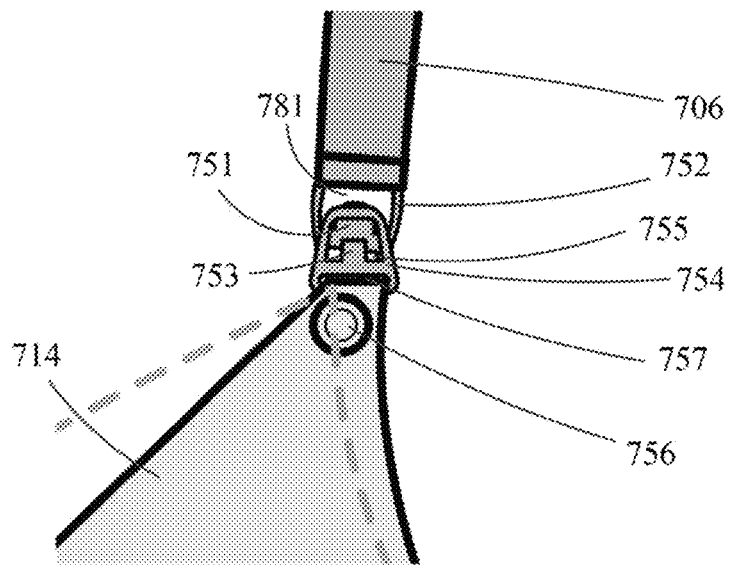
FIG. 13D is an enlarged view of the region 13D of FIG. 13C.

Additionally, as shown in FIGS. 13C and 13D, the inner panel 770 can include one or more holes 743 defined in an upper edge of the inner panel 770. For example, in some embodiments, the inner panel 770 can define the holes 743 and/or the holes 743 can be defined by a separate component coupled to the inner panel 770. As described for previous embodiments, a center strap 746 can be attached to the inner panel 770 via selective releasable engagement with any of the holes 743. The center strap 746 can be the same or similar in structure and/or function to the center strap 246 described above. Additionally, as shown in FIG. 13C, the inner panel 770 can also include a center hole 743A for attachment of the center strap in the center of the garment 700.

The engagement mechanism 750 can be the same or similar in structure and/or function to any of the engagement mechanisms described herein, such as engagement mechanisms 350 or 650. As shown in FIG. 13B, which is an enlarged view of the region 13B of FIG. 13A. In this embodiment, the engagement mechanism 750 includes a first portion 752 and a second portion 754. The first portion 752 can be releasably engageable with the second portion 754 in the same manner as described above for engagement mechanism 750. In this embodiment, the outer panel 760 can be releasably coupled to the inner panel with a snap coupling 763. The snap coupler 763 can be configured to releasably couple a portion of the outer panel 760 to a portion of the inner panel 770 as described in more detail below. The first portion 752 of the engagement mechanism 750 can include an extension portion 751, a first opening 781, and a second opening 783 (best shown in FIG. 13F) on an opposite side of the extension portion 751 than the first opening 781. The second portion 754 of the engagement mechanism 750 can include a tab portion 753, a first opening 755, and a second opening 757 on an opposite side of the tab portion 753 than the first opening 755. The snap coupler 763 can include a snap feature. For example, in some embodiments, the snap coupler 763 can include a first snap feature 763A secured to the outer panel 760 and a second complementary snap feature 763B secured to the inner panel 770.

The first portion 752 of the engagement mechanism 750 is coupled to one of the shoulder straps 706 with, for example, stitching in the same manner as described above for engagement mechanism 750. For example, an end portion of one of the shoulder straps 706 can be looped through the first opening 781 and attached to itself such that the first portion 752 is secured within the loop of the shoulder strap 706. Additionally, the first portion 752 of the engagement mechanism 750 can receive a portion of the support strap 780 through the second opening 783 such that the support strap 780 can be secured to the first portion 752 (see, e.g., FIGS. 13E and 13F). The extension portion 751 of the first portion 752 can be shaped and sized to be inserted through the first opening 755 of the second portion 754 to releasably couple the second portion 754 to the first portion 752 and, therefore, releasably couple the inner panel 770 to the support strap 780 similarly as described above with reference to FIGS. 9A and 9B. The tab portion 753 of the second portion 754 can be shaped and sized such that, when the extension portion 751 of the first portion 752 is received through the first opening 755 of the second portion 754, the tab portion 753 contacts or engages the extension portion 751 and is flexed or clicked into locking engagement with the first portion 752. In some embodiments, the tab portion 753 can be sufficiently elastic such that as the second portion 754 is moved into engagement with the first portion 752, the tab portion 753 can bend slightly and then snap into locking engagement.

In this embodiment, to secure the inner panel 770 to the second portion 754 of the clasp 750, the inner panel 770 can include a loop portion 711 (see, e.g., FIG. 13B). More specifically, as shown, for example. In FIG. 13D, the loop portion 711 can be formed by passing a portion of the inner panel 770 through the second opening 757 of the second portion 754 of the clasp 750, folding it upon itself and stitching it to the inner panel 770. Alternatively, the loop portion 711 can be a separate component or piece of material that is inserted through the second opening 757 and secured to the inner panel 770 (e.g., with stitching).

As shown in FIGS. 13A and 13B and described above, the first portion 752 and the second portion 754 of the engagement mechanism 750 can be engaged to releasably couple the inner panel 770 (e.g., right inner panel 712 and left inner panel 714) to the support straps 780. Additionally, the snap coupler 763 can releasably couple the outer panel 760 (e.g., the right outer panel 762 and the left outer panel 764) to the inner panel 770 (e.g., right inner panel 712 and left inner panel 714) such that the outer panel 760 substantially covers the inner panel 770 by coupling the first snap feature 763A secured to the outer panel 760 with the second complementary snap feature 763B secured to the inner panel 770. Although the outer panel 760 is shown as covering the entire inner panel 770 in FIG. 13A, in some embodiments, the outer panel 760 can only cover a portion of the inner panel 770. For example, in some embodiments, the outer panel 760 can cover only the cup portions of the inner panel 770.

FIG. 13C is a front view of the garment 700 shown with the outer panel 760 completely removed for illustrative purposes. Although the garment 700 is shown with the outer panel 760 completely removed, it should be understood that the outer panel 760 would remain attached to the inner panel 770 when the first snap feature 763A of the outer panel 760 has been decoupled from the second snap feature 763B of the inner panel 770. For example, as described above, the outer panel 760 can be attached to the inner panel 770 along a portion of the upper edges and/or along a portion of the bottom edges of the inner panel 770 in the regions outside of the cup regions via, for example, sewing/stitching.

As shown in FIG. 13D, which is an enlarged view of the region 13D in FIG. 13C, the left outer panel 764 has been detached from the left inner panel 714 by removing (i.e., unsnapping) the first snap feature 763A of the outer panel left outer panel 764 from the second snap feature 763B of the left inner panel 714. Thus, the left inner panel 714 is exposed and accessible by the user. As shown in FIG. 13C, detaching and moving (e.g., folding down) the outer panels 762 and 764 can reveal the right inner panel 712 and the left inner panel 714. With the outer panels 762 and/or 764 moved uncovering at least a portion of the inner panels 712 and/or 714, respectively, a user can gain access to the openings 730 to insert a breast pump as described above.

Figure 13E:
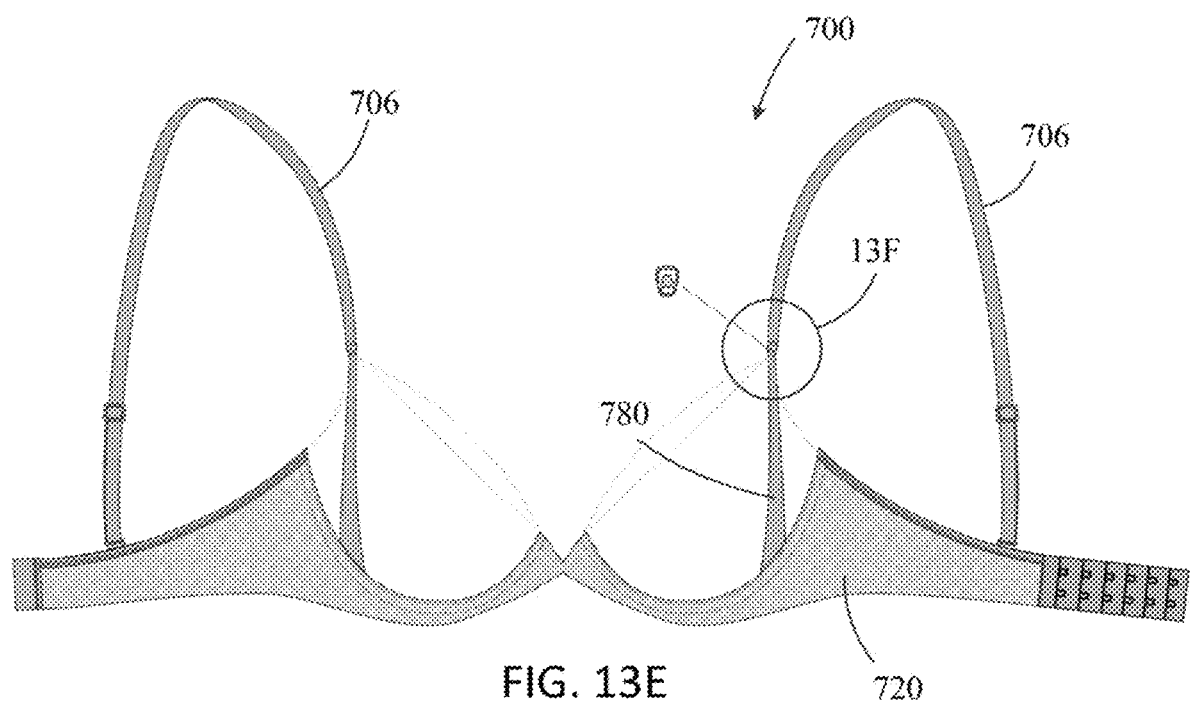
FIG. 13E is a front view of the garment of FIG. 13A shown with the inner panel and the outer panel removed but shown in dashed line for illustrative purposes.
Figure 13F:
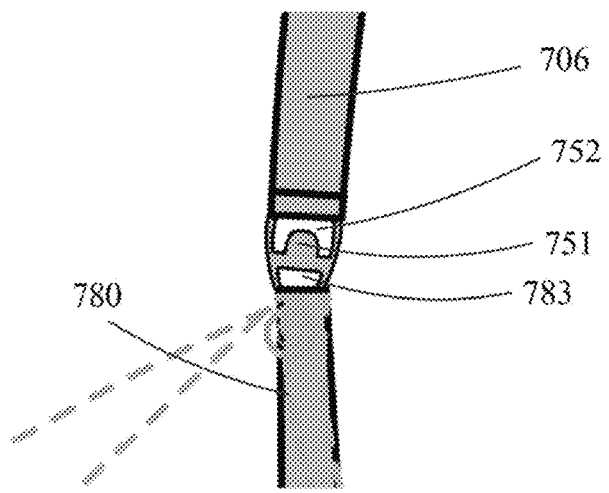
FIG. 13F is an enlarged view of the region 13F of FIG. 13E.

FIG. 13E is a front view of the garment 700 shown with the inner panel 770 completely removed for illustrative purposes. Thus, as shown in FIG. 13F, which is an enlarged view of the region 13F in FIG. 13E, when the outer panel 760 and the inner panel 770 are both detached from the support strap 780, the garment 700 can still be held in place on the body of the wearer via, the shoulder straps 706 and support straps 780. Although the garment 700 is shown in FIG. 13E with the outer panel 760 and the inner panel 770 completely removed, it should be understood that the outer panel 760 and the inner panel 770 would remain at least partially attached to the back panel 720 when the second portion 754 has been decoupled from the first portion 752 of the engagement mechanism 750 and the outer panel 760 is detached from the inner panel 770. For example, as described above, the outer panel 760 and/or the inner panel 770 can be attached to the back panel 720 along the bottom edge of the outer panel 760 and/or inner panel 770 via, for example, sewing/stitching.

In use, the garment 700 can be worn by a wearer and if access to a breast of the wearer is desired, such as for breast pumping, the first snap feature 763A can be detached from the second snap feature 763B such that the outer panel 760 (right outer panel 762 and/or left outer panel 764) can be moved (e.g., folded down) relative to the inner panel 770 and such that the inner panel 770 is accessible. The first portion 715 and the second portion 717 of the inner panel 770 (e.g., the right inner panel 712 and/or the left inner panel 714) can be separated (e.g., stretched or folded) to create an opening 730 such that the wearer's breast is accessible through the opening 730. If further access to the breast of the wearer is desired, the inner panel 770 can be detached from the support strap 780 and the shoulder strap 706 by removing the second portion 754 of the engagement mechanism 750 from the first portion 752 of the engagement mechanism 750. When desired, the inner panel 770 and the outer panel 760 can be reattached to the support strap 780 via recoupling the second portion 754 to the first portion 752, and recoupling the first snap portion 763A to the second snap portion 763B.

Figure 14A:
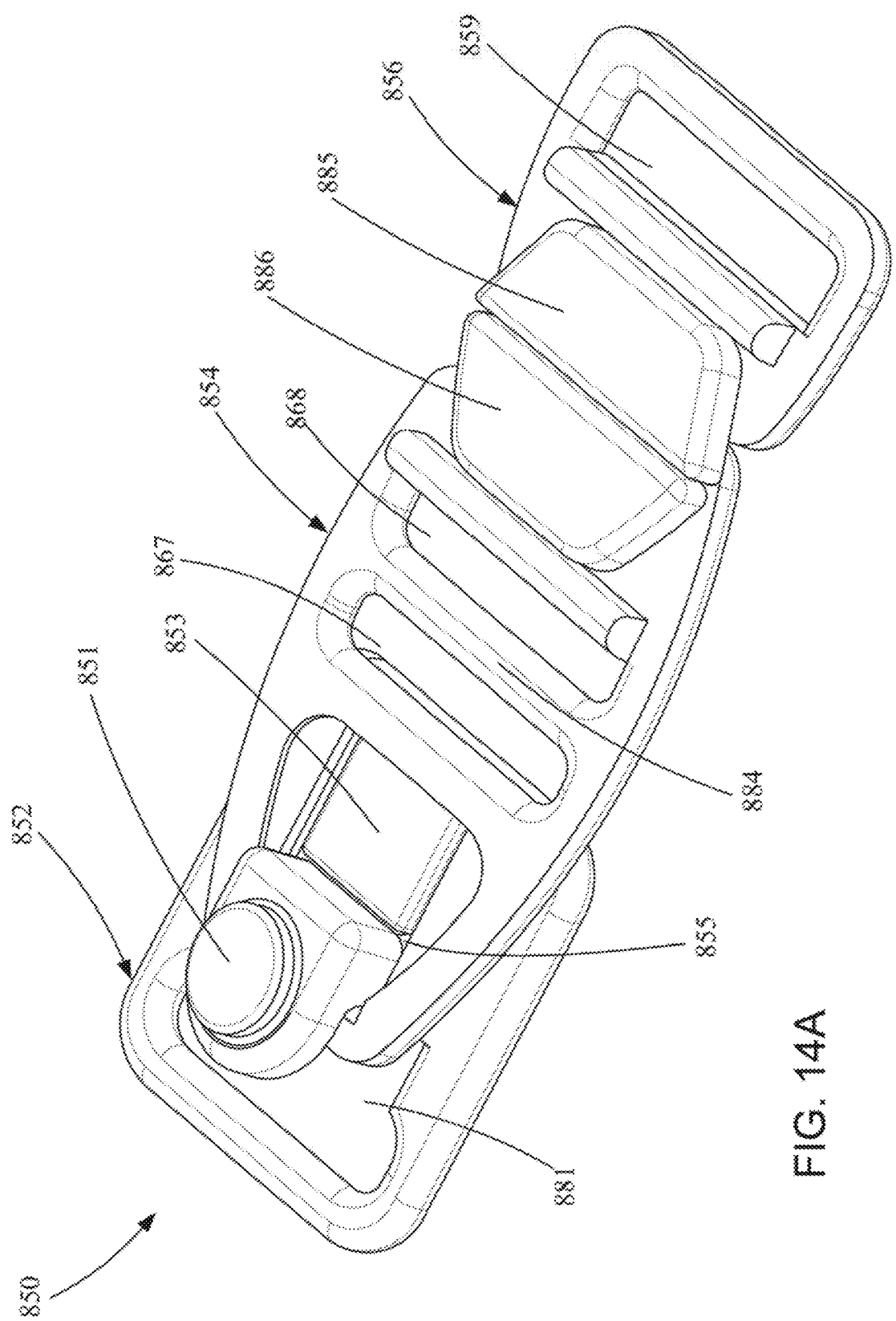
FIG. 14A is a perspective view of an engagement mechanism, according to an embodiment.

FIGS. 14A-15C illustrate an engagement mechanism 850 (also referred to herein as a "clasp"), according to an embodiment that can be used to releasably, couple the shoulder straps, support strap, inner panels and outer panels of a garment 800 (see, FIGS. 16A-16D). The garment 800 can be the same as or similar to the embodiments of a garment described herein (e.g., 200, 300, 400, 600, 700 described above). FIG. 14A is a perspective view of the engagement mechanism 850. As shown in FIG. 14A, the engagement mechanism 850 can include a first portion 852, a second portion 854, and a third portion 856. The first portion 852 can be configured to be releasably engageable with the second portion 854. Similarly, the second portion 854 can be configured to be releasably engageable with the third portion 856. The first portion 852 can include an extension portion 851, a first opening 881, and a second opening 883 (best shown, for example, in FIG. 14B) on an opposite side of the extension portion 851 than the first opening 881. The second portion 854 can include a tab portion 853, a first opening 855, a securement bar 884, a second opening 867, a third opening 868, and an engagement portion 885. The third portion 856 can include an engagement portion 886 and an opening 859.

Figure 14B:
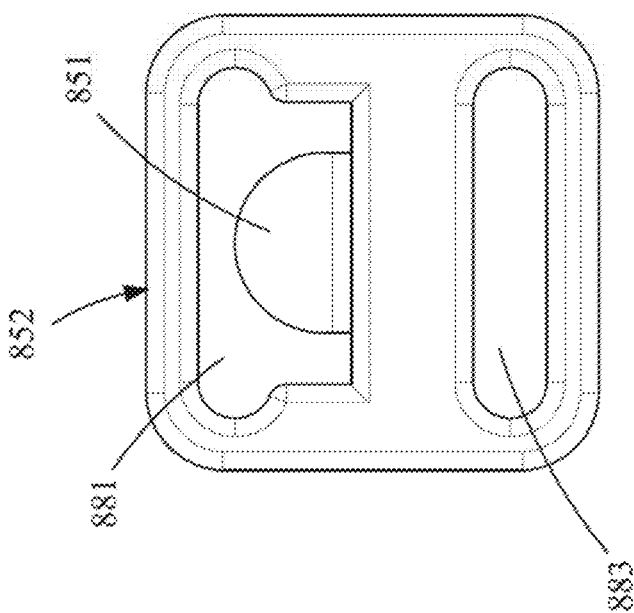
FIG. 14B is a front view of a first portion of the engagement mechanism of FIG. 14A.
Figure 14C:
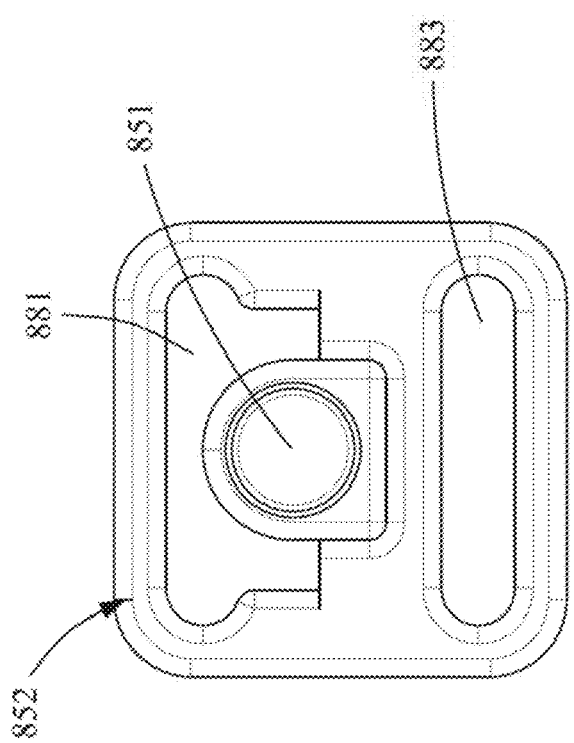
FIG. 14C is a hack view of the first portion of the engagement mechanism of FIG. 14A.
Figure 14D:
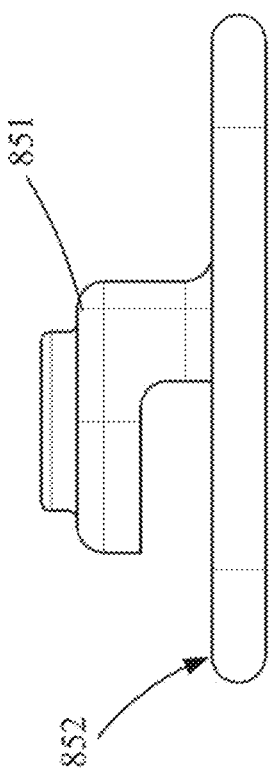
FIG. 14D is a side view of the first portion of the engagement mechanism of FIG. 14A.

FIGS. 14B-14D are a front view, back view and side view, respectively, of the first portion 852 of the clasp 850. The first portion 852 of the engagement mechanism 850 can be coupled to a shoulder strap 806 of the garment 800 as described in more detail below, with, for example, stitching. For example, an end portion of the shoulder strap 806 can be looped through the first opening 881 and attached to itself such that a top portion of the first portion 852 is secured within the loop of the shoulder strap. Additionally, the first portion 852 can receive a portion of a support strap 880 of the garment 800 through the second opening 883 such that the support strap 880 can be secured to the first portion 852 of the engagement mechanism 850. For example, an end portion of the support strap 880 can be looped through the second opening 883 of the first portion 852 and attached to itself (e.g., with stitching) such that a bottom portion of the first portion 852 is secured within the loop of the support strap 880.

FIGS. 14E-14G are a front view, a back view and a side view, respectively, of the second portion 854 of the clasp 850. The first opening 855 of the second portion 852 can be shaped and sized such that the first opening 855 can receive the extension portion 851 of the first portion 852 similarly as described above with reference to FIGS. 9A and 9B. The tab portion 853 of the second portion 854 can be shaped and sized such that when the extension portion 851 of the first portion 852 is received through the first opening 855 of the second portion 854, the tab portion 853 contacts or engages the extension portion 851 and is flexed or clicked into locking engagement with the first portion 852. In some embodiments, the tab portion 853 can be sufficiently elastic such that as the second portion 854 is moved into engagement with the first portion 852, the tab portion 853 can bend slightly and then snap into locking engagement. The securement bar 884 of the second portion 854 is configured for attachment to an inner panel 870 of the garment 800 (see FIGS. 16A and 16C). For example, a loop portion of an inner panel can be secured around the securement bar 884.

Figure 14I:
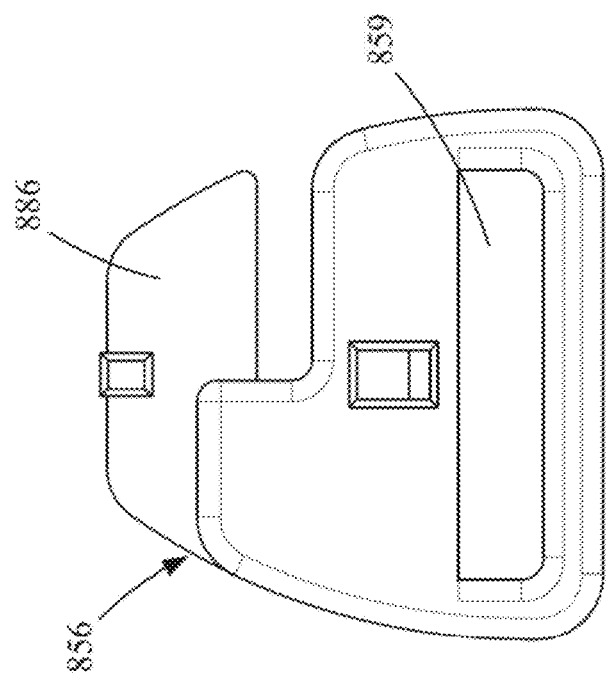
FIG. 14I is a hack view of the third portion of the engagement mechanism of FIG. 14A.
Figure 14H:
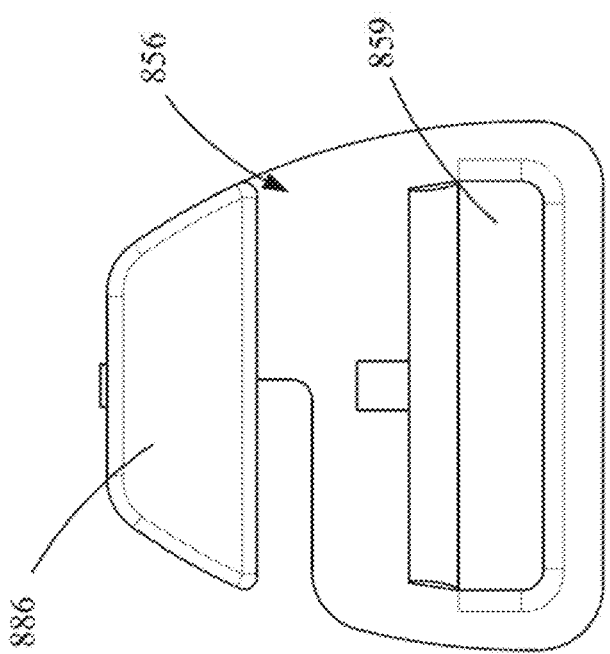
FIG. 14H is a front view of a third portion of the engagement mechanism of FIG. 14A.
Figure 14J:
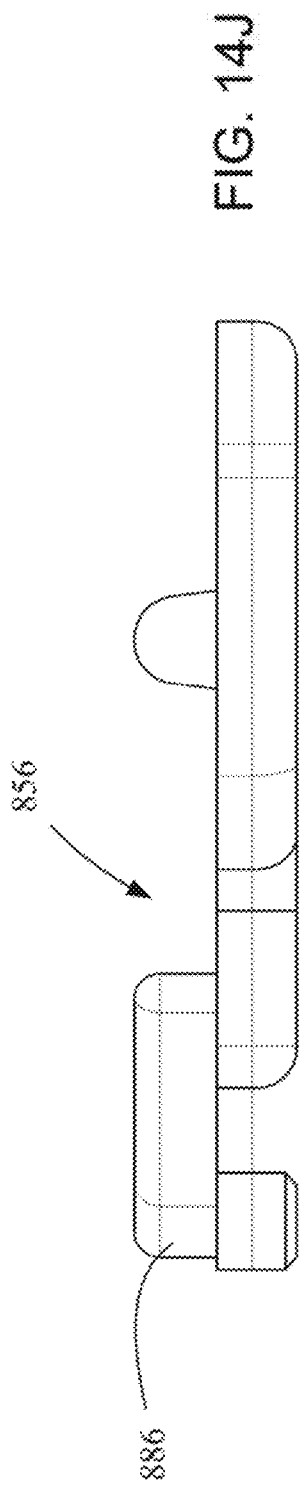
FIG. 14J is a side view of the third portion of the engagement mechanism of FIG. 14A.

FIGS. 14H-14J are a front view, a back view and a side view, respectively, of the third portion 856 of the clasp 850. The engagement portion 886 of the third portion 856 can releasably engage with the engagement portion 885 of the second portion 854. Although the engagement portion 886 and the engagement portion 885 are shown as being formed in the interlocking shapes shown in FIGS. 14A-15C, the engagement portion 886 and the engagement portion 885 can include any suitable releasably interlocking shapes. Additionally, the third portion 856 can receive a portion of an outer panel 860 of the garment 800 (see FIGS. 16A and 16B), within the opening 859 such that the outer panel 860 can be secured to the third portion 856 via the portion of the outer panel 860 being, for example, looped through the opening 859.

Figure 15A:
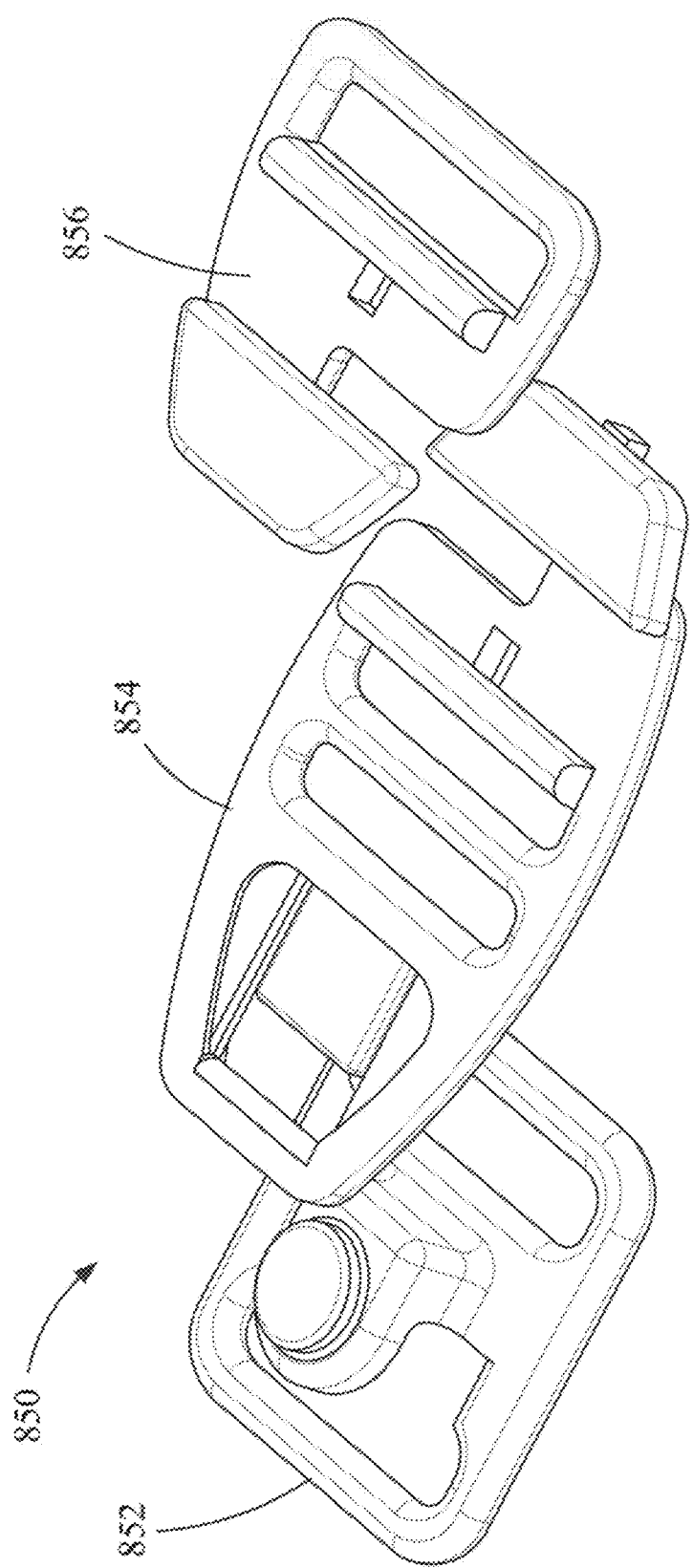
FIG. 15A is an exploded perspective view of the engagement mechanism of FIG. 14A, according to an embodiment, in a first configuration.
Figure 15B:
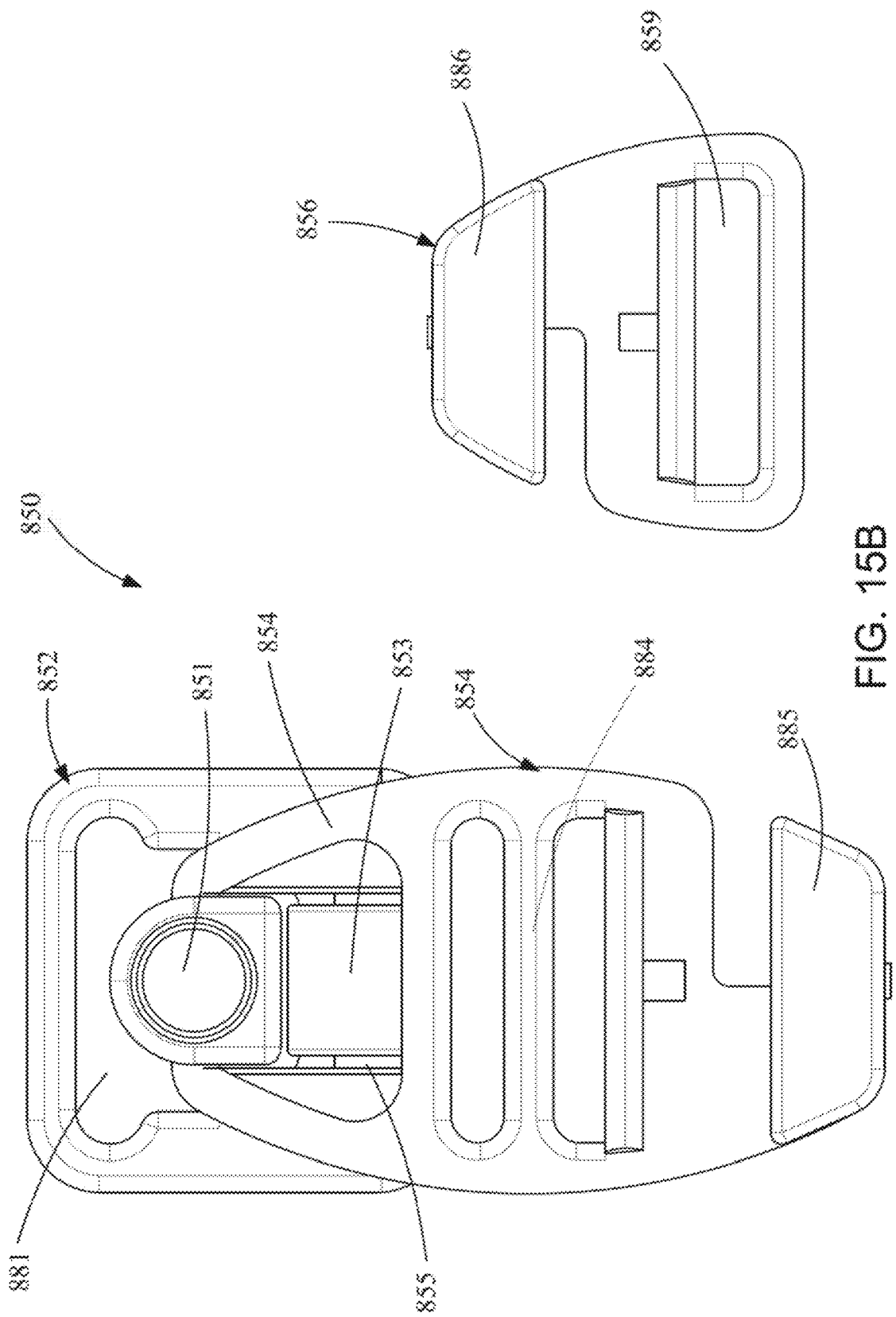
FIG. 15B is a front view of the engagement mechanism of FIG. 15A with the third portion of the engagement mechanism decoupled from the first and second portions.

FIG. 15A is an exploded perspective view of the first portion 852, the second portion 854, and the third portion 856 of the engagement mechanism 850 in a first configuration in which the first portion 852, the second portion 854, and the third portion 856 are disengaged from one another. FIG. 15B is a front view of the engagement mechanism 850 in a second configuration in which the second portion 854 is releasably engaged with the first portion 852 and the third portion is disengaged with the second portion 854. The extension portion 851 of the first portion 852 can be shaped and sized to be inserted through the first opening 855 of the second portion 854 to releasably couple the second portion 854 to the first portion 852 and, therefore, releasably couple the inner panel 860 of the garment 800 to the support strap 880 as described in more detail below. The tab portion 853 of the second portion 854 can be shaped and sized such that, when the extension portion 851 of the first portion 852 is received through the first opening 855 of the second portion 854, the tab portion 853 contacts or engages the extension portion 851 and such that it is flexed or clicked into locking engagement with the first portion 852, as shown in FIG. 15B and in a similar manner as described above for the tab portion of other embodiments of an engagement mechanism, such as engagement mechanism 350. In such a configuration, the tab portion 853 can be disposed in locking engagement with the extension portion 851 of the first portion 852. The engagement between the first portion 852 and the second portion 854 can be reversed in the same manner as described above for engagement mechanism 350.

Figure 15C:
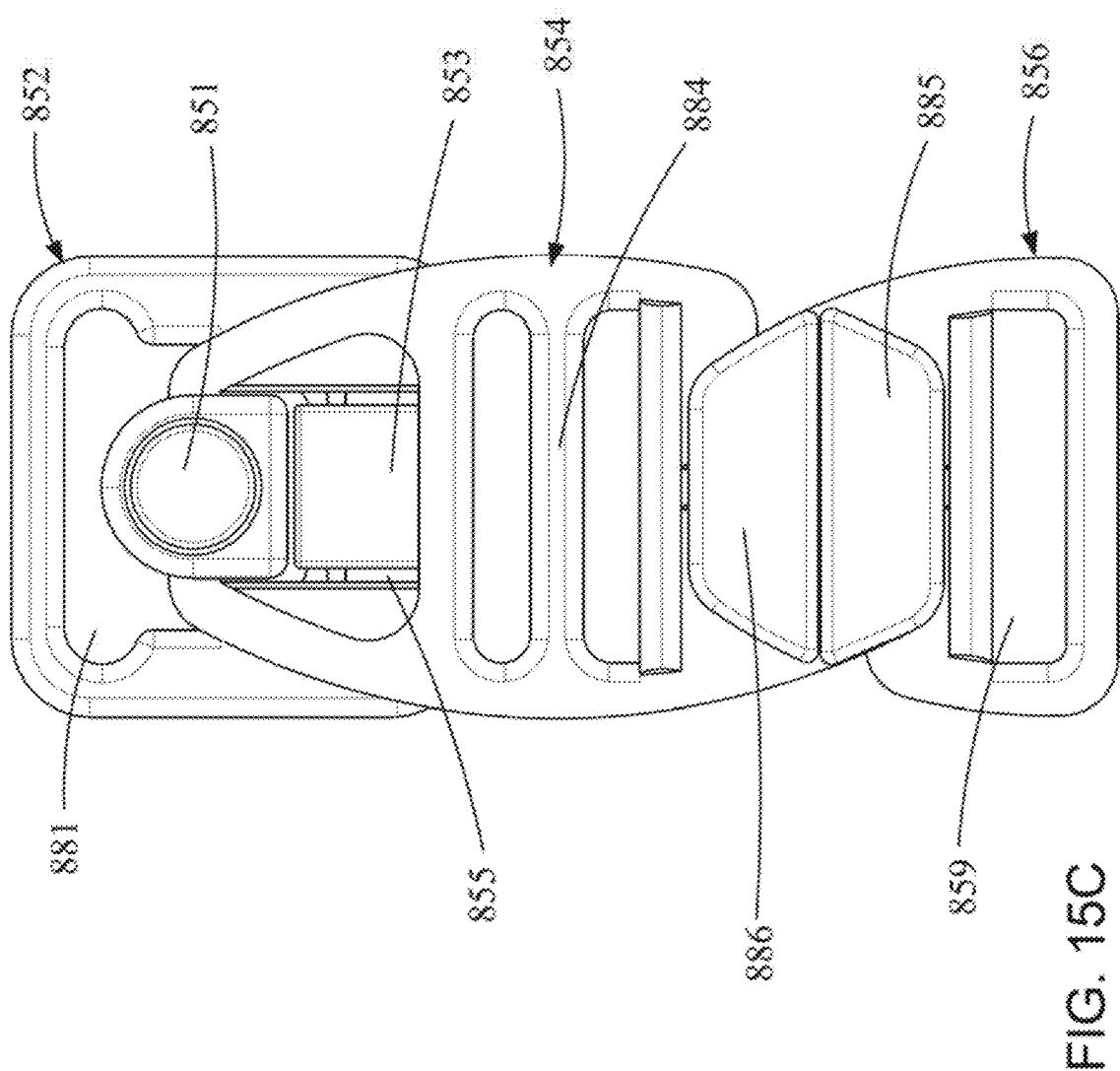
FIG. 15C is a front view of the engagement mechanism of FIG. 14A.

FIG. 15C is a front view of the first portion 852, the second portion 854, and the third portion 856 of the engagement mechanism 850 in a third configuration in which the first portion 852 is engaged with the second portion 854 and the second portion 854 is engaged with the third portion 856.

FIGS. 16A-16D show a portion of a garment 800 including the engagement mechanism 850 in various configurations. The garment 800 can be the same or similar in structure and/or function to any of the garments described herein, and therefore, various features of the garment 800 are not described in detail with reference to FIGS. 16A-16D. The garment 800 can include an outer panel 860, an inner panel 870, and a support strap 880 (shown in FIG. 16D). The garment 800 can include shoulder straps 806 that can be coupled to the outer panel 860, the inner panel 870, and the support strap 880 via the engagement mechanism 850.

The first portion 852 of the engagement mechanism 850 can be coupled to the shoulder strap 806 with, for example, stitching. For example, an end portion of the shoulder strap 806 can be looped through the first opening 881 and attached to itself such that the first portion 852 is secured within the loop of the shoulder strap 806. Additionally, the first portion 852 can be configured to receive a portion of the support strap 880 through the second opening 883 such that the support strap 880 can be secured to the first portion 852 (see, e.g., FIG. 16D). To secure the inner panel 870 to the second portion 854 of the clasp 850, the inner panel 870 can include a loop portion that is attachable to the securement bar 884 of the second portion 854. For example, the loop portion of the inner panel 870 can be formed by passing a portion of the inner panel 870 around the securement bar 884, folding it upon itself, and stitching it to the inner panel 870. Alternatively, the loop portion of the inner panel 870 can be a separate component or piece of material that is inserted through the second opening 857 and secured to the inner panel 870 (e.g., with stitching). Similarly, the third portion 856 of the clasp 850 can receive a portion of the outer panel 860 within the opening 859 such that the outer panel 860 can be secured to the third portion 856 of the clasp 850 (see, e.g., FIG. 16B) in a similar manner as described for securing the inner panel 870 to the second portion 854 (e.g., a portion of the outer panel 860 being, for example, looped through the opening 859).

Figure 16D:
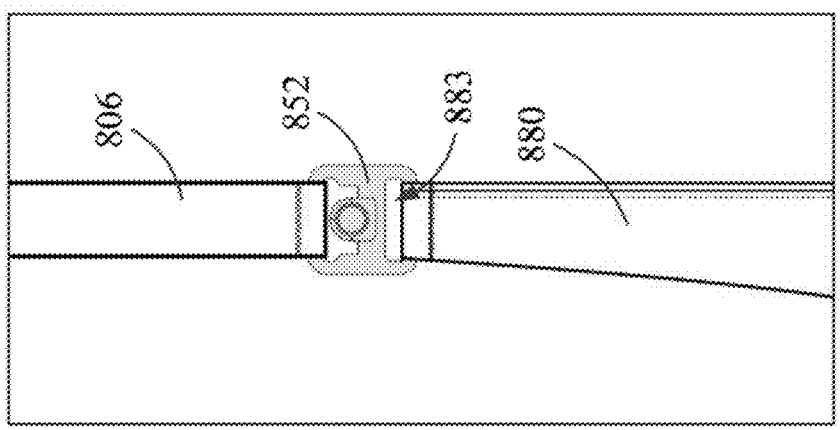
FIG. 16D is a front view of a portion of the garment of FIG. 16A in a third configuration, showing a support strap and the second portion and third portion of the engagement mechanism removed.
Figure 16C:
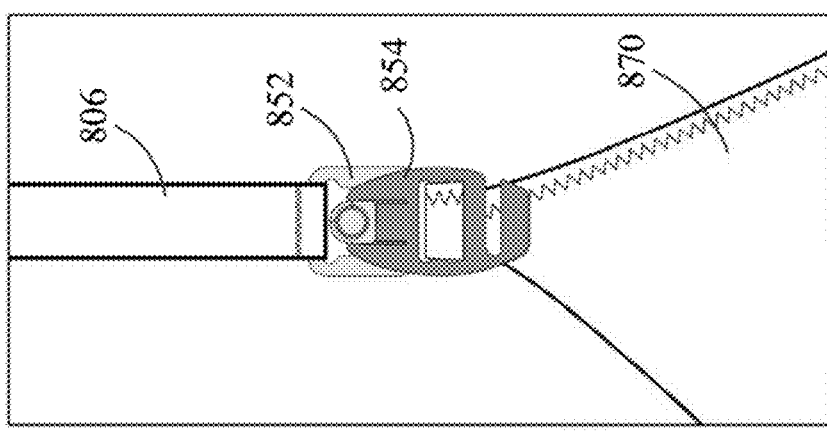
FIG. 16C is a front view of a portion of the garment of FIG. 16A in a second configuration, showing an inner layer and the third portion of the engagement mechanism and outer layer removed.
Figure 16B:
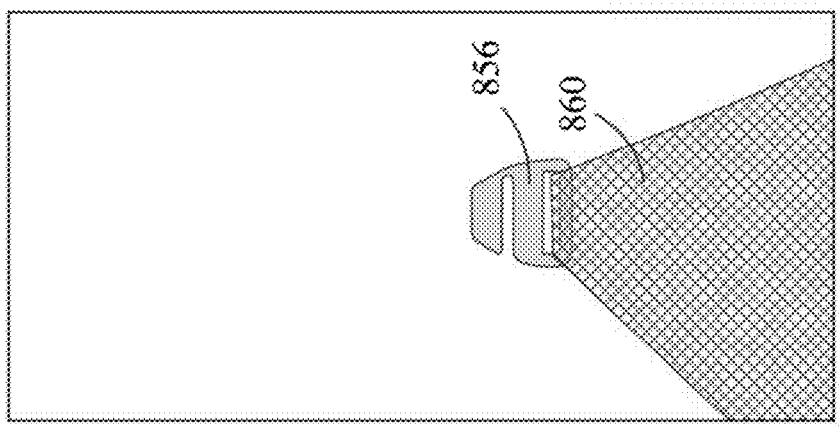
FIG. 16B is a front view of the third portion of the engagement mechanism and a portion of an outer layer portion of the garment of FIG. 16A.
Figure 16A:
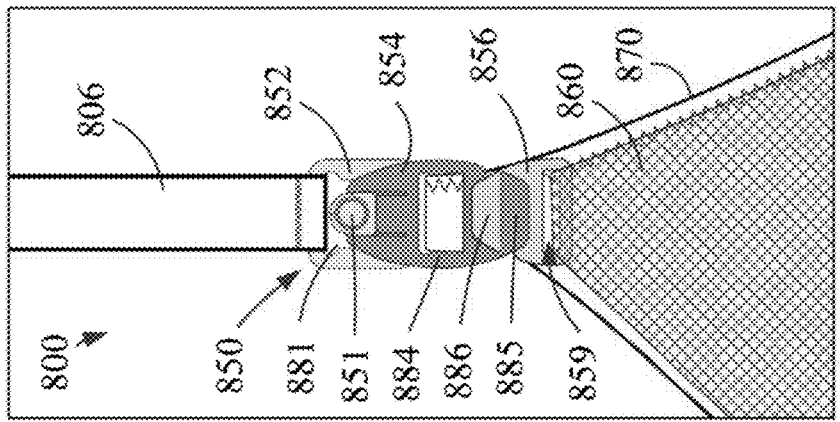
FIG. 16A is a front view of a portion of a garment including the engagement mechanism of FIG. 14A, in a first configuration in which a first portion, second portion and third portion of the engagement mechanism are coupled together.

As shown in FIG. 16A, the first portion 852 is engaged with the second portion 854 and the second portion 854 is engaged with the third portion 856 such that the outer panel 860 is coupled to and at least partially covers the inner panel 870 and the inner panel 870 is coupled to and at least partially covers the support strap 880 in a front view. As shown in FIG. 16B, the inner panel 870 can be uncovered via removing or decoupling the third portion 856 from the second portion 854 of the clasp 850 (i.e., removing the engagement portion 886 from the engagement portion 885) and moving (e.g., folding down) the outer panel 860 relative to the inner panel 870. Thus, as shown in FIG. 16C, the inner panel 870 is exposed and accessible by the user. The support strap 880 can be uncovered via removing or decoupling the second portion 854 from the first portion 852 of the clasp 850 (i.e., removing the extension portion 851 from the first opening 855) to detach the inner panel 870 from the support strap 880. Thus, as shown in FIG. 16D, the support strap 880 is exposed and accessible/viewable by the user. As described for previous embodiments, the support strap 880 and shoulder straps 806 can maintain the garment 800 supported on the user. In some embodiments, the outer panel 860 and the inner panel 870 can be detached from the first portion 852 of the engagement mechanism 850 simultaneously without removing the third portion 856 from the second portion 854. When desired, the inner panel 870 and the outer panel 860 can be reattached to the support strap 880 and shoulder strap 806 by recoupling the second portion 854 to the first portion 852 of the claps 850, and recoupling the third portion 856 to the second portion 854 of the clasp 850.

Figure 17A:
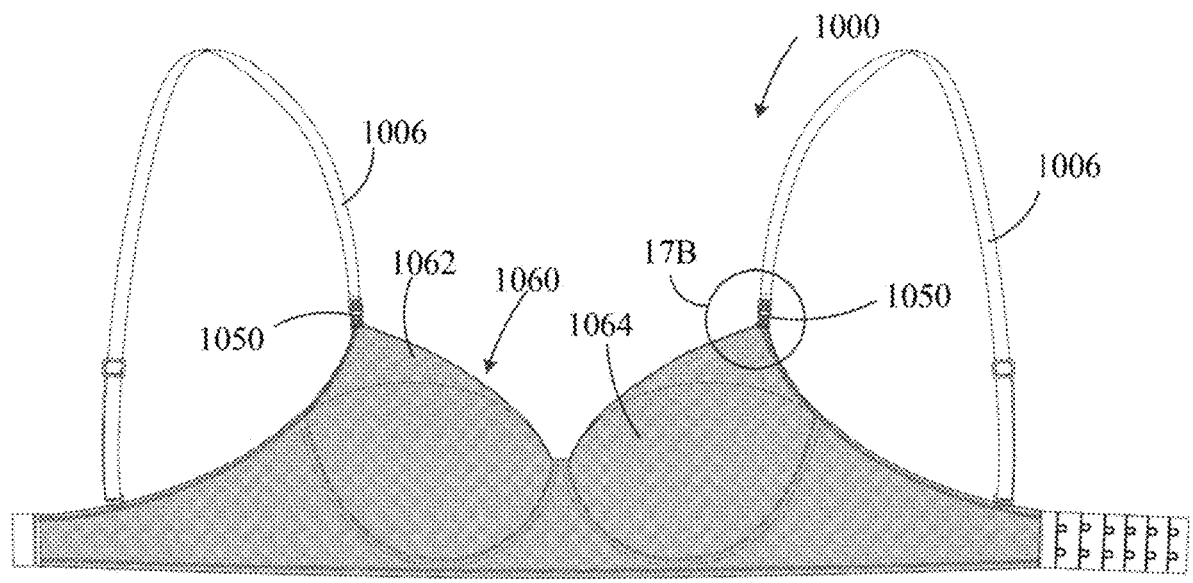
FIG. 17A is a front view of a garment, according to an embodiment.

FIGS. 17A-17F illustrate various views and components of a garment 1000. FIG. 17A is a front view of the garment 1000 in a first configuration. The garment 1000 can be the same or similar in structure and/or function to any of the garments described herein. For example, the garment 1000 can include an outer panel 1060, an inner panel 1070 (shown in FIG. 17C), two support straps 1080 (shown in FIG. 17E and two shoulder straps 1006. Each shoulder strap 1006 can be coupled to the outer panel 1060, the inner panel 1070, and a support strap 1080 via an engagement mechanism 1050 (also referred to herein as a "clasp").

The support straps 1080 can be coupled on a first end to a back panel 1020 and on a second end to one of the shoulder straps 1006 via the engagement mechanism 1050. In alternative embodiments, the support strap 1080 can be attached to a lower band of the garment 1000 rather than to the back panel 1020. Each of the shoulder straps 1006 can have a first end coupled to the support strap 1080 (via the engagement mechanism 1050) and a second end coupled to the back panel 1020. The outer panel 1060 and/or the inner panel 1070 can be attached to the back panel 1020, for example, along a bottom edge of the outer panel 1060 and/or along a bottom edge of the inner panel 1070, via, for example, sewing/stitching. Similarly, the outer panel 1060 and the inner panel 1070 can be coupled together along at least a portion of a bottom edge and/or along at least a portion of a top edge of the outer panel 1060 and the inner panel 1070.

The inner panel 1070 and the outer panel 1060 can each include one or more panels each formed with one or more layers of material. As shown, for example, in FIG. 17A, the outer panel 1060 includes a right outer panel 1062 and a left outer panel 1064. As shown, for example, in FIG. 17C, the inner panel 1070 includes a right inner panel 1012 and a left inner panel 1014. The right inner panel 1012 and the left inner panel 1014 can be shaped and sized for coverage of a wearer's right breast and left breast, respectively. Each of the right inner panel 1012 and the left inner panel 1014 can include a first portion 1015 and a second portion 1017 that are coupled together such that a portion is unattached and can define an opening 1030 (see FIG. 17C) between the first portion 1015 and the second portion 1017. In some embodiments, the first portion 1015 and the second portion 1017 can include an overlapping portion which can define the opening 1030. The first portion 1015 and the second portion 1017 can be separated by, for example, moving the first portion 1015 and the second portion 1017 away from each other, thereby creating the opening 1030 and providing access to the users breast. A breast pump can then be inserted through the opening 1030 and the inner panel 1070 can help support the breast pump during milk extraction.

Figure 17B:
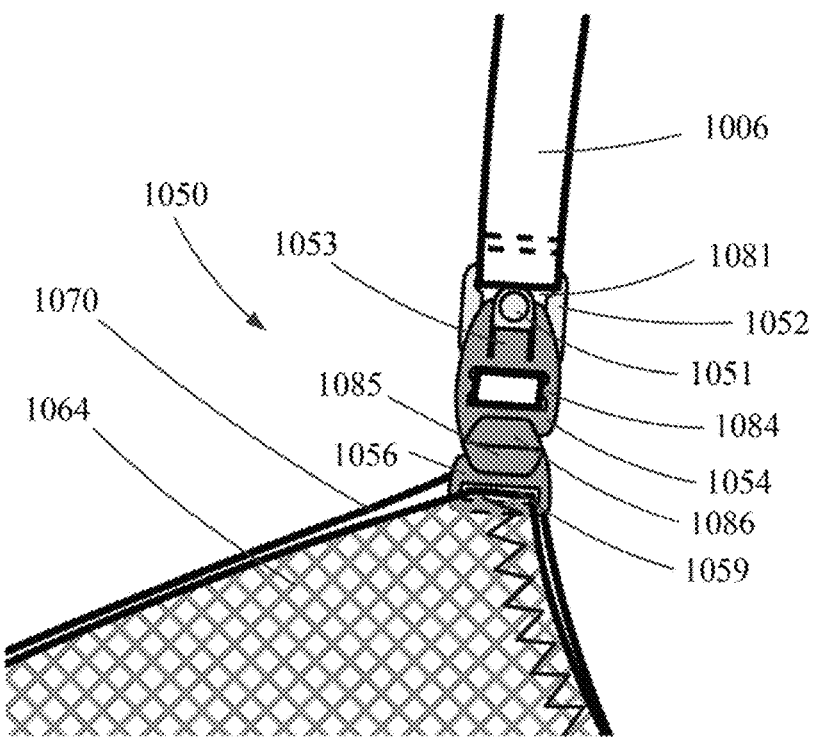
FIG. 17B is an enlarged view of the region 17B of FIG. 17A.
Figure 17C:
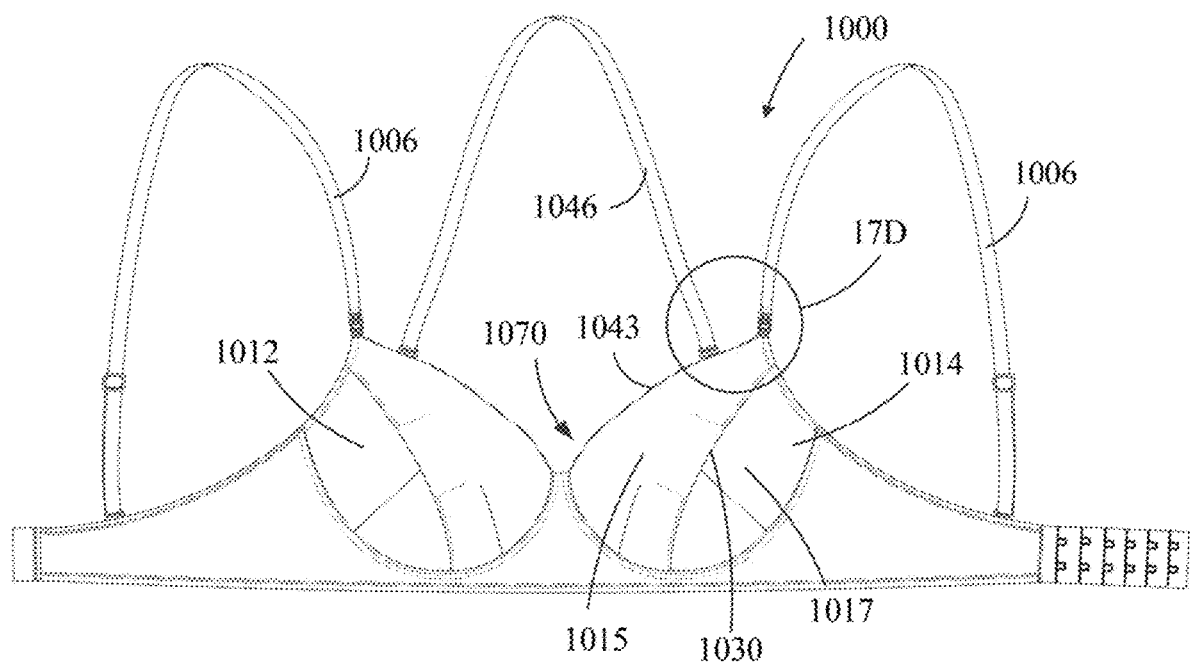
FIG. 17C is a front view of the garment of FIG. 17A shown with an outer panel removed for illustrative purposes.
Figure 17D:
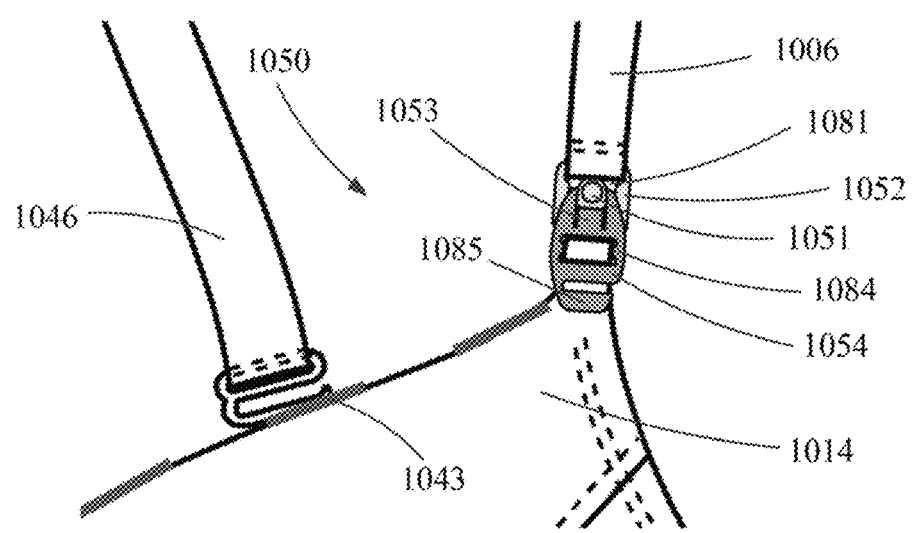
FIG. 17D is an enlarged view of the region 17D of FIG. 17C.

Additionally, as shown in FIGS. 17C and 17D, the inner panel 1070 can include one or more holes 1043 defined in an upper edge of the inner panel 1070. For example, in some embodiments, the inner panel 1070 can define the holes 1043 and/or the holes 1043 can be defined by a separate component coupled to the inner panel 1070. As described for previous embodiments, a center strap 1046 can be attached to the inner panel 1070 via, selective releasable engagement with any of the holes 1043. The center strap 1046 can be the same or similar in structure and/or function to the center strap 246 described above.

The engagement mechanism 1050 can be the same or similar in structure and/or function as the engagement mechanism 850 described above. As shown in FIG. 17B, which is an enlarged view of the region 17B of FIG. 17A, the engagement mechanism 1050 can include a first portion 1052, a second portion 1054, and a third portion 1056. The first portion 1052 can be releasably engageable with the second portion 1054, and the second portion 1054 can be releasably engageable with the third portion 1056. The first portion 1052 can include an extension portion 1051, a first opening 1081, and a second opening 1083 (best shown in FIG. 17F) on an opposite side of the extension portion 1051 than the first opening 1081. The second portion 1054 can include a tab portion 1053, a first opening 1055, a securement bar 1084, a second opening (not shown), a third opening (not shown), and an engagement portion 1085. The third portion 1056 can include an engagement portion 1086 and an opening 1059.

The first portion 1052 of the engagement mechanism 1050 is coupled to one of the shoulder straps 1006 with, for example, stitching. For example, an end portion of one of the shoulder straps 1006 can be looped through the first opening 1081 and attached to itself such that the first portion 1052 is secured within the loop of the shoulder strap 1006. Additionally, the first portion 1052 can receive a portion of the support strap 1080 through the second opening 1083 such that the support strap 1080 can be secured to the first portion 1052 (see, e.g., FIGS. 17E and 17F). The extension portion 1051 of the first portion 1052 can be shaped and sized to be inserted through the first opening 1055 of the second portion 1054 to releasably couple the second portion 1054 to the first portion 1052 and, therefore, releasably couple the inner panel 1060 to the support strap 1080 similarly as described above for previous embodiments. The tab portion 1053 of the second portion 1054 can be shaped and sized such that, when the extension portion 1051 of the first portion 1052 is received through the first opening 1055 of the second portion 1054, the tab portion 1053 contacts or engages the extension portion 1051 and such that it is flexed or clicked into locking engagement with the first portion 1052. In some embodiments, the tab portion 1053 can be sufficiently elastic such that as the second portion 1054 is moved into engagement with the first portion 1052, the tab portion 1053 can bend slightly and then snap into locking engagement.

In this embodiment, to secure the inner panel 1070 to the second portion 1054 of the clasp 1050, the inner panel 1070 can include a loop portion that is attachable to the securement bar 1084 of the second portion 1054. For example, the loop portion of the inner panel 1070 can be formed by passing a portion of the inner panel 1070 around the securement bar 1084, folding it upon itself, and stitching it to the inner panel 1070. Alternatively, the loop portion of the inner panel 1070 can be a separate component or piece of material that is inserted through the second opening 1057 and secured to the inner panel 1070 (e.g., with stitching). Similarly, the third portion 1056 of the clasp 1050 can receive a portion of the outer panel 1060 within the opening 1059 such that the outer panel 1060 can be secured to the third portion 1056 of the clasp in a similar manner as how the inner panel 1070 is secured to the second portion 1054 (e.g., a portion of the outer panel 1060 being, for example, looped through the opening 1059). The engagement portion 1086 of the third portion 1056 can be releasably engaged with the engagement portion 1085 of the second portion 1054. Although the engagement portion 1086 and the engagement portion 1085 are shown as being formed in the interlocking shapes shown in FIGS. 17A-17B, the engagement portion 1086 and the engagement portion 1085 can include any suitable releasably interlocking shapes.

As shown in FIGS. 17A and 17B and described above, the first portion 1052 and the second portion 1054 of the engagement mechanism 1050 can be engaged/coupled to couple the inner panel 1070 to the support strap 1080 and the shoulder strap 1006. Additionally, the third portion 1056 can be coupled to the second portion 1054 via engagement of the engagement portion 1086 with the engagement portion 1085 to couple the outer panel 1060 to the inner panel 1070 such that the outer panel 1060 substantially covers the inner panel 1070 as shown in FIG. 17A. Although the outer panel 1060 is shown as covering the entire inner panel 1070 in FIG. 17A, in some embodiments, the outer panel 1060 can only cover a portion of the inner panel 1070. For example, in some embodiments, the outer panel 1060 can cover only the cup portions of the inner panel 1070.

FIG. 17C is a front view of the garment 1000 shown with the outer panel 1060 completely removed for illustrative purposes. Although the garment 1000 is shown with the outer panel 1060 completely removed, it should be understood that the outer panel 1060 would remain at least partially attached to the inner panel 1070 when the third portion 1056 has been removed from the second portion 1054 of the clasp 1050. For example, as described above, the outer panel 1060 can be attached to the inner panel 1070 along at least a portion of the upper edges of the inner panel 1070 and/or along at least a portion of the bottom edges of the inner panel 1070

As shown in FIG. 17D, which is an enlarged view of the region 17D in FIG. 17C, the left outer panel 1064 has been detached from the left inner panel 1014 by removing/decoupling the third portion 1056 from the second portion 1054 of the clasp 1050 (i.e., removing the engagement portion 1086 from the engagement portion 1085). Thus, the inner panel 1070 is exposed and accessible by the user. FIG. 17C illustrates both the left outer panel 1064 and right outer panel 1062 removed from the left inner panel 1014 and right inner panel 1012, respectively.

Figure 17E:
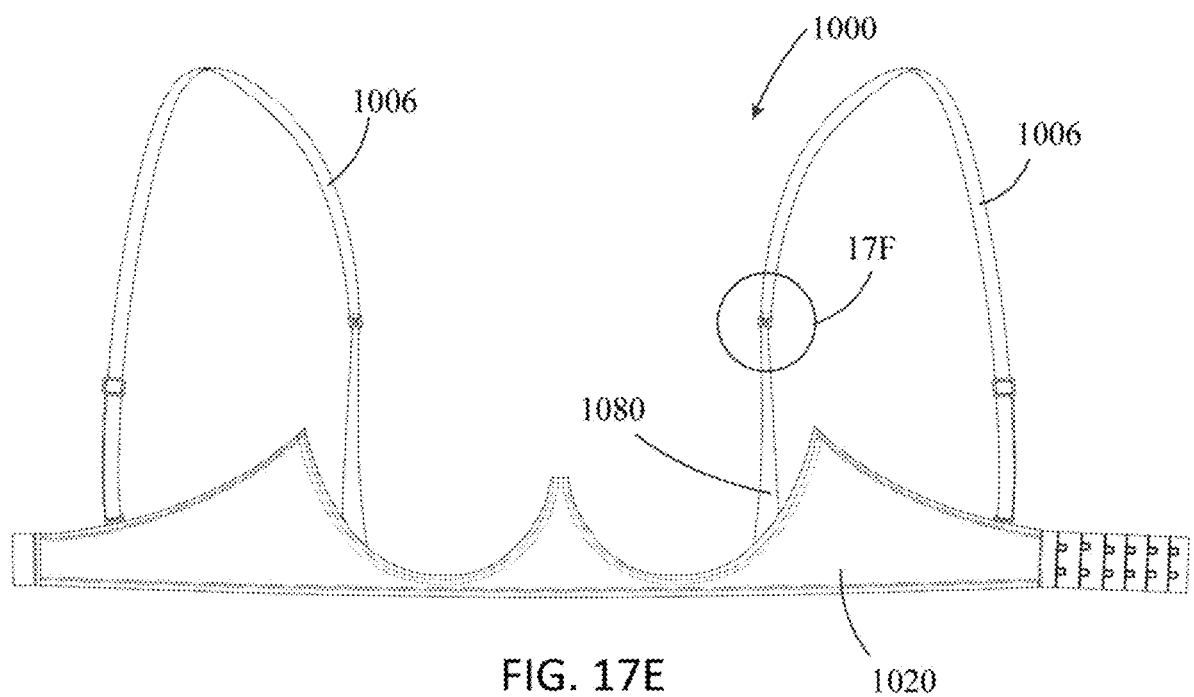
FIG. 17E is a front view of the garment of FIG. 17A shown with the inner panel and the outer panel removed for illustrative purposes.
Figure 17F:
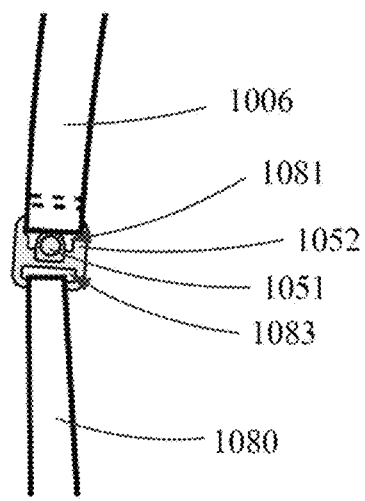
FIG. 17F is an enlarged view of the region 17F of FIG. 17E.

FIG. 17E is a front view of the garment 1000 shown with the inner panel 1070 completely removed for illustrative purposes and FIG. 17F is an enlarged view of the region 17F in FIG. 17E. With both the inner panel 1070 and outer panel 1060 detached from the shoulder straps 1006 and support straps 1080, the garment 1000 can still be held in place on the body of the wearer via the shoulder straps 1006 and support straps 1080. Although the garment 1000 is shown in FIG. 17E with the outer panel 1060 and the inner panel 1070 completely removed, it should be understood that the outer panel 1060 and the inner panel 1070 would remain attached to the back panel 1020 when the second portion 1054 has been removed from the first portion 1052 of the support strap 1080.

In use, the garment 1000 can be worn by a wearer and if access to a breast of the wearer is desired, such as for breast pumping, the outer panel 1060 (e.g., the right outer panel 1062 and/or the left outer panel 1064) can be detached from the inner panel 1070 (e.g., the right inner panel 1012 and/or the left inner panel 1014) by detaching or uncoupling the third portion 1056 from the second portion 1054 of the clasp 1050 and the outer panel 1060 can be moved (e.g., folded down) such that the inner panel 1070 is accessible. As described above, the first portion 1015 and the second portion 1017 of the inner panel 1070 (e.g., the right inner panel 1012 and/or the left inner panel 1014) can be separated (e.g., stretched or folded) to create an opening 1030 through which the wearer's breast is accessible and a portion of a breast pump can be inserted. If further access to the breast of the wearer is desired, the inner panel 1070 can be detached from the support strap 1080 and shoulder straps 1006 by removing/detaching the second portion 1054 of the engagement mechanism 1050 from the first portion 1052 of the clasp 1050. In some embodiments, the outer panel 1060 and the inner panel 1070 can be detached from shoulder straps 1006 and support strap 1080 simultaneously by detaching the second portion 1454 from the first portion 1052 but not detaching third portion 1056 from the second portion 1054. When desired, the inner panel 1070 and the outer panel 1060 can be reattached to shoulder strap 1006 and support strap 1080 by recoupling the second portion 1054 to the first portion 1052 of the clasp 1050, and recoupling the third portion 1056 to the second portion 1054 of the clasp 1050.

FIGS. 18A-19C illustrate various views and components of a garment 1100 that can be used with a wearable breast pump or wearable milk collection device. As described above, such wearable breast pumps or milk collection devices are placed in contact with a user's breast between the breast and the outer panel of the garment (e.g., bra). With use of such a breast pump or collection device, it may be desirable to provide for adjustment of the size and/or position of the cup portion of the garment 1100 (e.g., bra) to reduce or prevent stretching of the cup portion that may be due to the size of the wearable pump or collection device.

The garment 1100 can include components that are the same or similar in structure and/or function to any of the garments described herein. For example, the garment 1100 can include an outer panel 1160, a support strap 1180 (shown in FIG. 18B), shoulder straps 1106 and a back panel 1120. Each shoulder strap 1106 can be coupled to the outer panel 1160 and the support strap 1180 via an engagement mechanism 1150 (also referred to herein as a "clasp"). The outer panel 1160, support straps 1180, shoulder straps 1106, back panel 1120 and engagement mechanism 1150 can be the same or similar in construction and function as the outer panel 1060, support straps 1080, shoulder straps 1006, back panel 1020 and engagement mechanism 1050, respectively, described above, and therefore, some features and details are not described with reference to this embodiment. For example, the various components can be coupled together in the same manner as described above for previous embodiments.

Figure 19B:
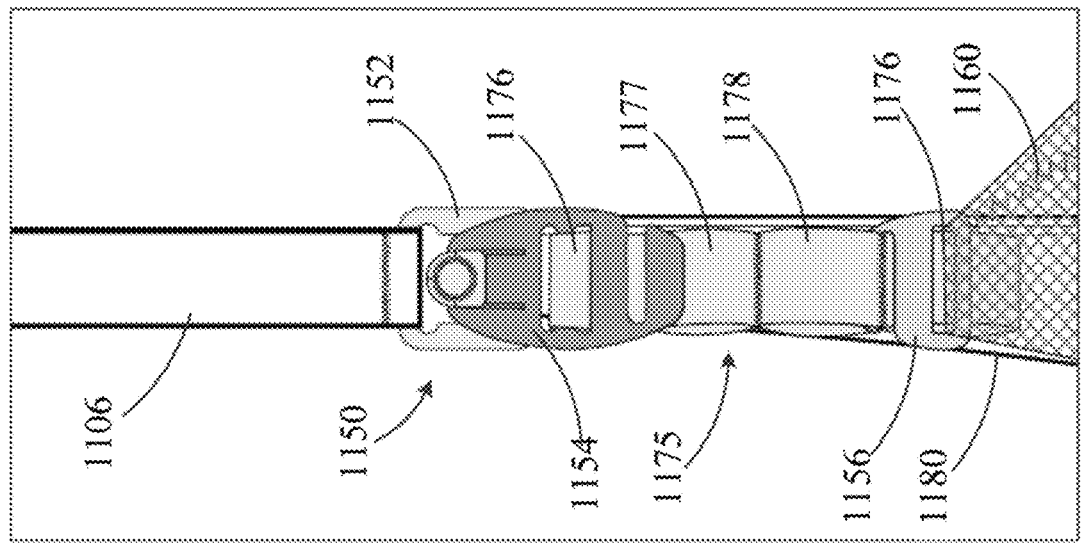
FIG. 19B is a front view of a portion of the garment of FIG. 18B with the third portion of the engagement mechanism coupled to a selected loop of the extender of the garment of FIG. 18A.
Figure 19A:
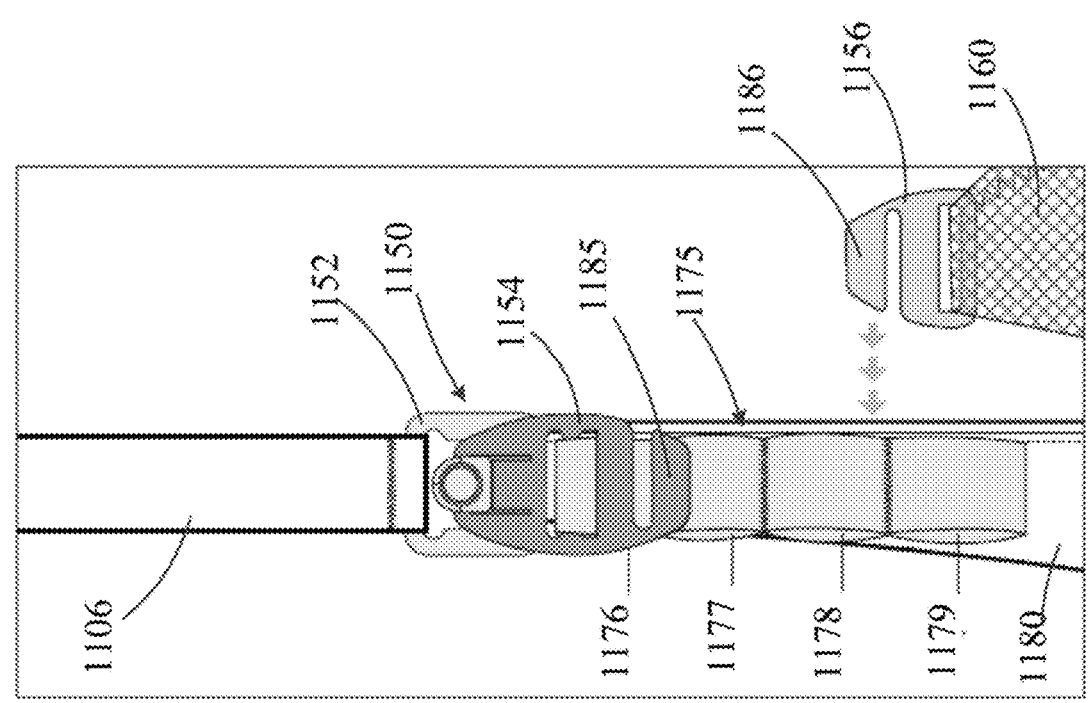
FIG. 19A is a front view of a portion of the garment of FIG. 18A with the third portion of the engagement mechanism and the outer panel detached from the second portion of the engagement mechanism.

In this embodiment, in place of an inner panel (as described for previous embodiments), the garment 1100 includes extenders 1175 coupled to the support straps 1180 and the shoulder straps 1106 via the engagement mechanism 1150 as described in more detail below. The extenders 1175 can include multiple loops that can provide for selective adjustment of the releasable attachment of the outer panel 1160 to the shoulder strap 1106 and the support strap 1180. In this embodiment, as shown in FIGS. 19A and 19B, the extenders 1175 include four loops, 1176, 1177, 1178 and 1179, with one of the loops (loop 1176) coupled to the engagement mechanism 1150, and the remaining loops hanging down or extending therefrom. The loops 1176, 1177, 1178, 1179 can be formed from one or more pieces of material or fabric. For example, in some embodiments, the loops 1176, 1177, 1178, 1179 can be formed from a single piece of material or fabric with the loops formed by stitching. In some embodiments, one or more of the loops 1176, 1177, 1178, 1170 can be formed with a separate piece of material or fabric and coupled together with, for example, stitching. It should be understood that an extender 1175 can include more or less loops, such as, for example, two, three, five, six, seven, eight, nine, ten, etc. Thus, the extender 1175 can have various lengths depending on the number of loops included. In some embodiments, the extenders 1175 can be formed with, for example, an elastic material or fabric to accommodate additional adjustment of the outer panel 1160 (e.g., the cup size) through the stretchability of the extender 1175. In other words, the overall length of the extender 1175 can be increased. In some embodiments, the extenders 1175 can be formed with a non-stretchable material or fabric, in which case the length of the extender would not vary during use.

As described above, the outer panel 1160 can include one or more panels each formed with one or more layers of material. As shown, for example, in FIG. 18A, the outer panel 1160 includes a right outer panel 1162 and a left outer panel 1164. The right outer panel 1160 and the left outer panel 1164 can be shaped and sized for coverage of a wearer's right breast and left breast, respectively. Additionally, although not shown in FIG. 18A, the outer panel 1160 can include one or more holes defined in an upper edge of the outer panel 1160 to couple a center or neck strap (e.g., center strap 246) (not shown in FIGS. 18E and 18B), in the same or similar manner as described above for the inner panels in previous embodiments.

Figure 19D:
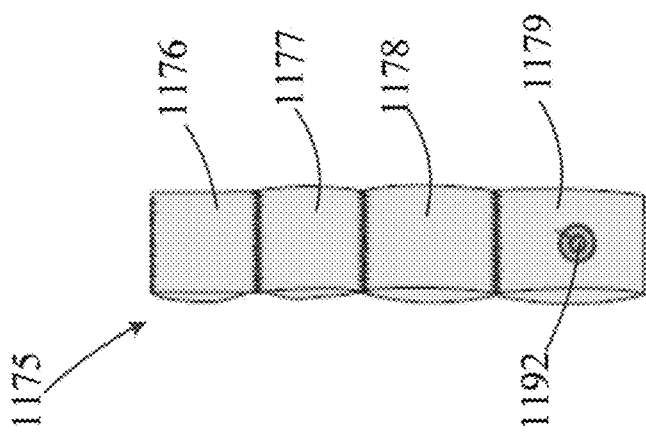
FIG. 19D is a back view of the extender of the garment of FIG. 18A.
Figure 19C:
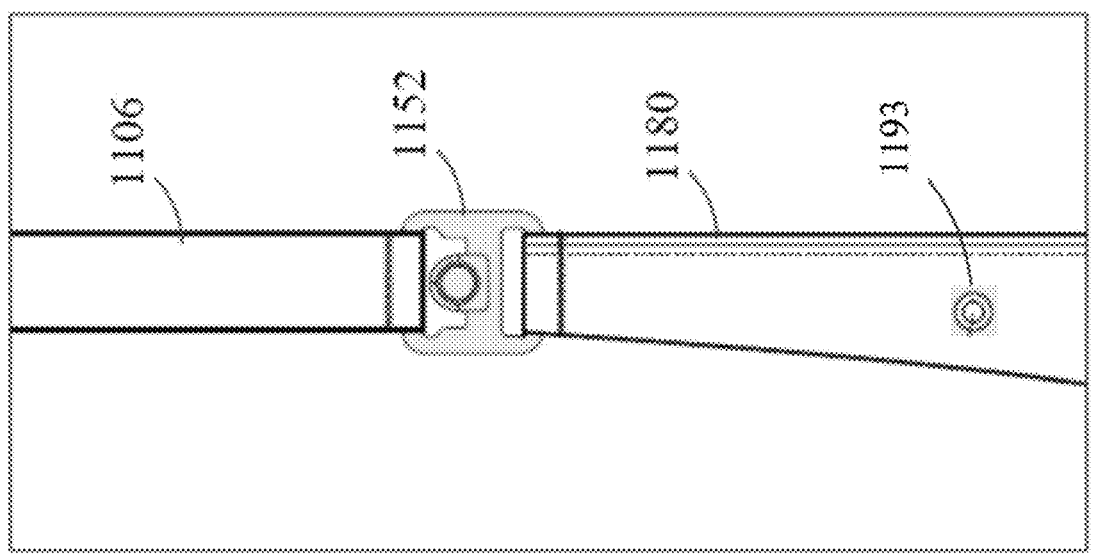
FIG. 19C is a front view of a portion of the garment of FIG. 18A with the third portion and second portion of the engagement mechanism detached from the first portion of the engagement mechanism and thus, the outer panel and inner panel detached from the support strap and shoulder strap.

The engagement mechanism 1150 can be the same or similar in structure and/or function as the engagement mechanisms 850 and 1050 described above. As best shown in FIGS. 19A-19C, the engagement mechanism 1150 can include a first portion 1152, a second portion 1154, and a third portion 1156. The first portion 1152 can be releasably engageable with the second portion 1154, and the second portion 1154 can be releasably engageable with the third portion 1156. The first portion 1152 can be coupled to the shoulder strap 1106 and the support strap 1180 in the same manner as described above for garments 800 and 1000, as best shown in FIG. 19C. In this embodiment, the second portion 1154 of the engagement mechanism 1150 is secured to the extender(s) 1175, as shown, for example, in FIGS. 19A and 19B. More specifically, the loop 1176 of the extender 1175 is attachable to the second portion 1154 in the same or similar manner as to how the inner panel 1070 is attached to the second portion of the engagement mechanism 1050. For example, the loop 1176 of the extender 1175 can be formed by passing the material forming the loop 1175 around the securement bar (e.g., securement bar 1084 described above for engagement mechanism 1050), folding it upon itself, and stitching it to another portion of the extender 1175. Because the second portion 1154 of the engagement mechanism 1150 is releasably coupleable to the first portion 1152, the extender 1175 is also releasably coupleable to the first portion 1152, and therefore, releasably coupleable to the shoulder strap 1106 and the support strap 1180. To further secure extender 1175 to the support strap 1180 and maintain its position during use, a first coupler 1192 can be attached to the backside of the extender 1175 that can be releasably coupled to a mating coupler 1193 disposed on the front side of the support strap 1180, as shown in FIGS. 19C and 19D. For example, as shown in FIGS. 19C and 19D, the coupler 1192 can be disposed on the backside of loop 1179 such that the extender 1175 is attached at a top portion to the first portion 1152 of the engagement mechanism 1150 and can be releasably attached at a bottom portion to the support strap 1180. The couplers 1192 and 1193 can be, for example, snap connectors (e.g., a male and female snap connectors), a hook and loop coupling, VELCRO, buttons, etc.

As best shown in FIGS. 19A and 19B, the third portion 1156 of the engagement mechanism 1150 can be coupled to the outer panel 1160 (e.g., the right outer panel 1162 and the left outer panel 1164) in the same manner as described above for engagement mechanism 850 and engagement mechanism 1050. As with the previous embodiments, the third portion 1156 of the engagement mechanism 1150 can include an engagement portion 1186 that can be releasably engaged with an engagement portion 1185 of the second portion 1154 (see, e.g., FIG. 19A showing the engagement portions 1185 and 1186 disengaged from each other), such that the outer panel 1160 can be releasably coupled to the shoulder straps 1106 and the support straps 1180.

Figure 18A:
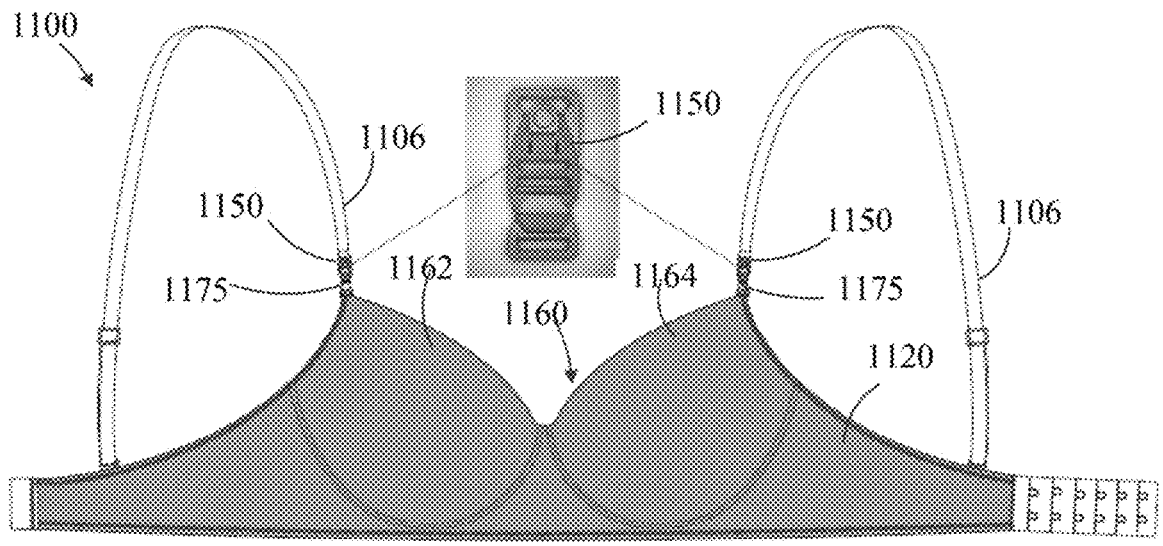
FIG. 18A is a front view of a garment, according to another embodiment.

During normal use of the garment 1100, the outer panel 1160 (e.g., left outer panel 1164 and right outer panel 1162) can be releasably coupled to the shoulder straps 1106 and the support straps 1180 by coupling the third portion 1156 to the second portion 1154 as shown in FIG. 18A. In this position, the outer panel 1160 is sized and positioned to be closest to the user's breast. To accommodate a wearable breast pump or milk collection device, the user can adjust the size and position of the outer panel 1160 relative to the user's breast and relative to the shoulder straps 1106 by releasably coupling the engagement portion 1186 of the third portion 1156 of the engagement mechanism 1150 to a selected one of the loops 1177, 1178, 1179. For example, as shown in FIG. 19B, the engagement portion 1186 is inserted through and coupled to the loop 1178 and the loop 1179 is tucked behind the outer panel 1160. Thus, in this position, the outer panel 1160 is extended further from the shoulder strap 1106 and thus can provide more space for the insertion of a wearable breast pump or collection device.

Figure 18B:
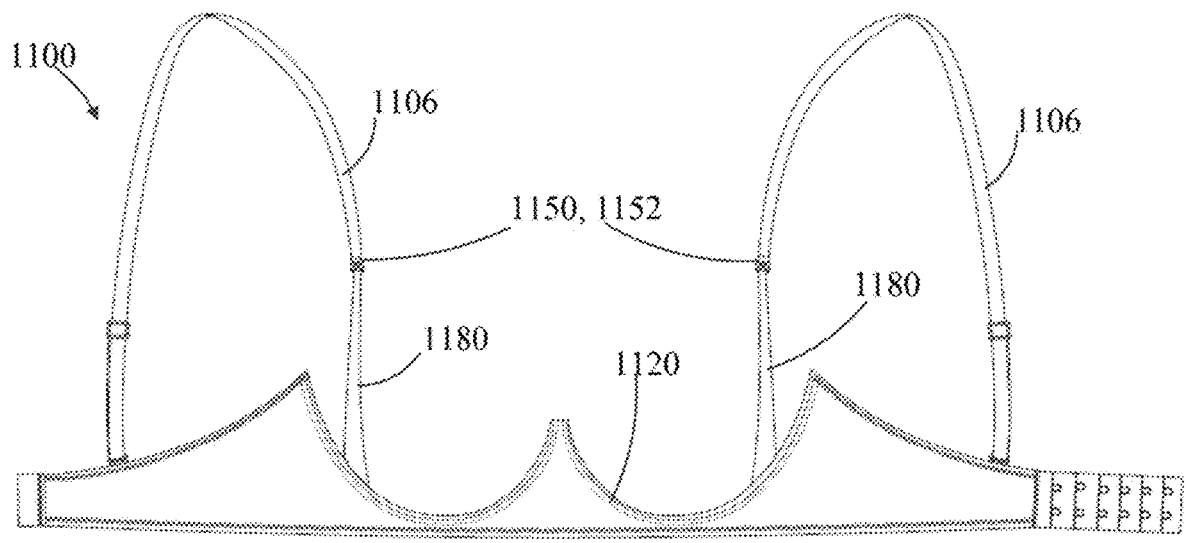
FIG. 18B is a front view of the garment of FIG. 18A shown with the outer panel removed for illustrative purposes.

If a user wants to gain full access to one or both breasts to, for example, nurse, the second portion 1154 of the engagement mechanism 1150 can be detached from the first portion 1152, which detaches the outer panel 1160 from the shoulder strap 1106 and the support strap 1180, as shown, for example, in FIG. 19A. As also shown in FIG. 19A, the extender 1175 can optionally remain coupled to the shoulder strap 1106 and support strap 1180 when the outer panel 1160 is removed, or can be removed by detaching the second portion 1154 from the first portion 1152 of the engagement mechanism 1150, as shown in FIGS. 18B and 19C. As with previous embodiments, with the outer panel 1160 detached from the shoulder straps 1106 and support straps 1180, the garment 1100 can still be held in place on the body of the wearer via the shoulder straps 1106 and support straps 1180. Although the garment 1100 is shown in FIG. 18B with the outer panel 1160 completely removed, it should be understood that the outer panel 1160 would remain attached to the back panel 1120 when the second portion 1154 has been detached from the first portion 1152 of the engagement mechanism 1150.

In an alternative embodiment of a garment such as garment 1100 that can be used with a wearable breast pump or wearable milk collection device, rather than the engagement mechanism 1150, an engagement mechanism such as engagement mechanism 350 can be included. In such an embodiment, the garment can be constructed and function the same as the garment 1100 except the hook portion (e.g., the s-shaped portion 358) of the third portion (e.g., third portion 356) of the engagement mechanism can be selectively received within one of the loops of the extender to releasable couple the outer panel to the support strap and the shoulder strap.

FIGS. 20A-21C illustrate another embodiment of a garment that can be worn with a wearable breast pump or wearable milk collection device. The garment 1200 can include components that are the same or similar in structure and/or function to any of the garments described herein. For example, the garment 1200 can include an outer panel 1260, a support strap 1280 (best shown in FIG. 20B), shoulder straps 1206 and a back panel 1220. Each shoulder strap 1206 can be coupled to the support strap 1280 via an engagement mechanism 1250 (also referred to herein as a "clasp"). The outer panel 1260, support straps 1280, shoulder straps 1206 and back panel 1220 can be the same or similar in construction and function as the outer panel 1060, support straps 1080, shoulder straps 1006 and hack panel 1020, respectively, and therefore, some features and details are not described with reference to this embodiment. For example, the various components can be coupled together in the same manner as described above for previous embodiments.

Figure 21C:
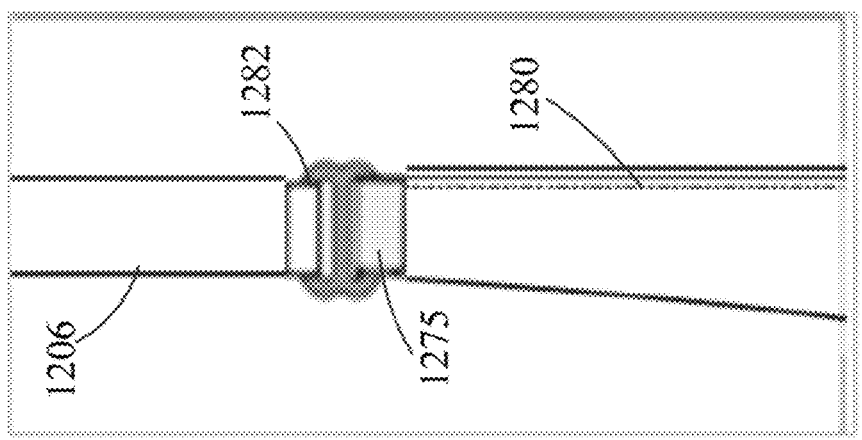
FIG. 21C is a back view of a portion of the garment of FIG. 20A illustrating the attachment of the support strap to the extender.
Figure 21B:
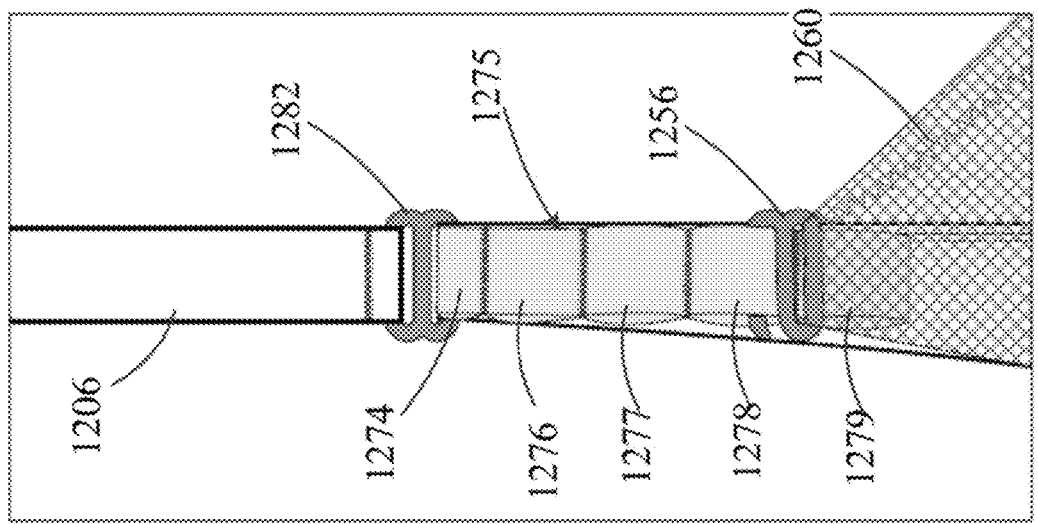
FIG. 21B is a front view of a portion of the garment of FIG. 20A with the second portion of the engagement mechanism coupled to a selected loop of the extender.
Figure 21A:
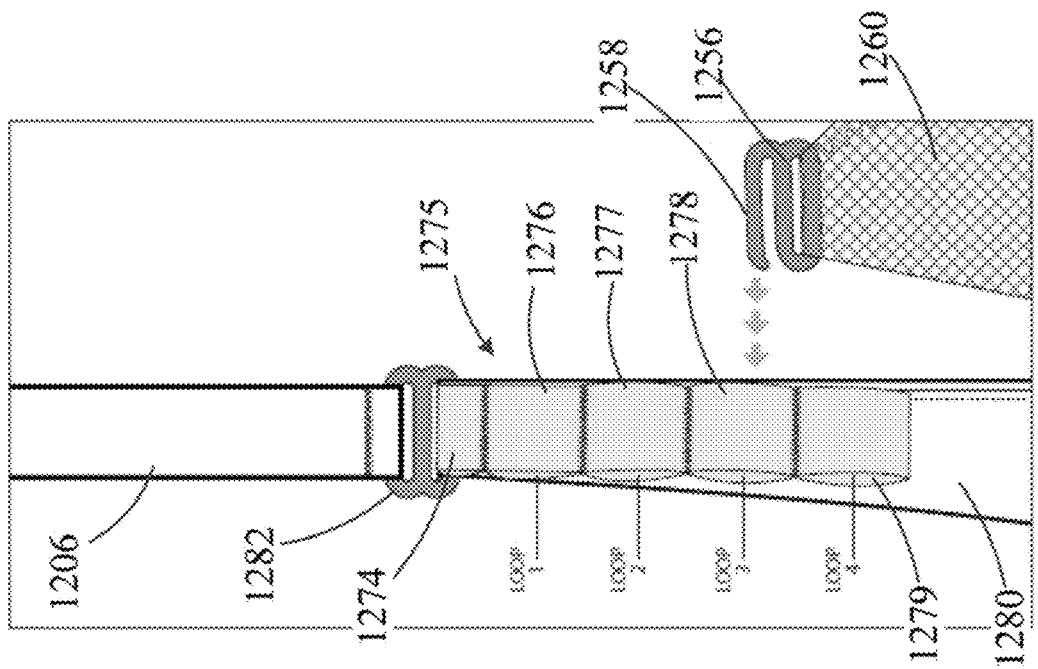
FIG. 21A is a front view of a portion of the garment of FIG. 20A with a second portion of the engagement mechanism and the outer panel detached from the extender.

As with the previous embodiment, in place of an inner panel (as described for previous embodiments), the garment 1200 includes extenders 1275 coupled to the support straps 1280 and the shoulder straps 1206. The extenders 1275 can be constructed the same as or similar to the extenders 1175 described above and can include multiple loops that can provide for selective adjustment of the releasable attachment of the outer panel 1260 to the shoulder strap 1206 and the support strap 1280. In this embodiment, as shown in FIGS. 21A and 21B, the extenders 1275 include four loops, 1276, 1277, 1278 and 1279, for selective coupling of the outer panel 1260 and a connection loop 1274 coupled to a clip 1282. The loops 1276, 1277, 1278, 1279 can be formed and constructed of the same materials as described above for extenders 1175. The extender 1275 can include more or less loops, such as, for example, two, three, five, six, seven, eight, nine, ten, etc. Thus, the extender 1275 can have various lengths depending on the number of loops included.

As described above, the outer panel 1260 can include one or more panels each formed with one or more layers of material. As shown, for example, in FIG. 20A, the outer panel 1260 includes a right outer panel 1262 and a left outer panel 1264. The right outer panel 1260 and the left outer panel 1264 can be shaped and sized for coverage of a wearer's right breast and left breast, respectively. Additionally, although not shown in FIG. 20A, the outer panel 1260 can include one or more holes defined in an upper edge of the outer panel 1260 to couple a center or neck strap (e.g., center strap 246) (not shown in FIG. 20A), in the same or similar manner as described above for the inner panels in previous embodiments.

Figure 22:
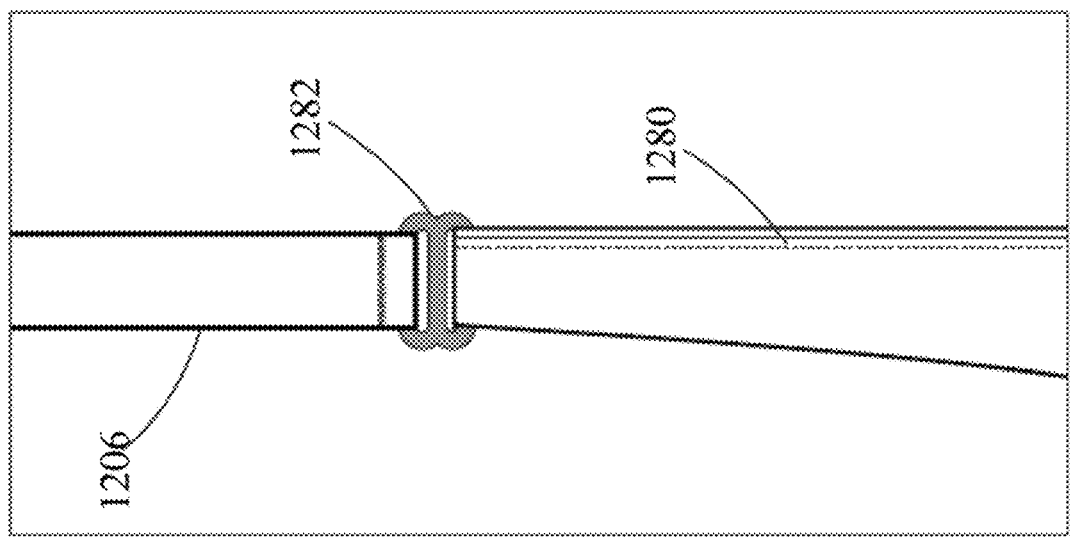
FIG. 22 is a front view of a portion of a garment showing an alternative attachment of the support strap.

In this embodiment, the clip 1282 is coupled to the shoulder strap 1206 and also coupled to the extender 1275. For example, as best shown in FIGS. 21A and 21B, a portion of the shoulder strap 1206 can be received through a top opening of the clip 1250 and looped over a first portion of the clip 1282 and sewn or stitched to secure the shoulder strap 1206 to the clip 1282. Similarly, a portion of the extender 1275 can be received through a bottom opening of the clip 1282 and looped over a second portion of the clip 1282 and sewn or stitched to secure the extender 1275 to the clip 1282. The support strap 1280 can be sewn or stitched to the back side of the extender 1275, as shown, for example, in the back view of FIG. 21C. In an alternative construction, shown in FIG. 22, the support strap 1280 can be secured to the clip 1282 rather than to the extender 1275. For example, a portion of the support strap 1280 can be received through the bottom opening of the clip 1282 and looped over the second portion of the clip 1282 and sewn or stitched to secure the support strap 1280 to the clip 1282. In such an embodiment, the extender 1275 can be sewn or stitched to the front side of the support strap 1280. As with the previous embodiment, to further secure extender 1275 to the support strap 1280 and maintain its position during use, a first coupler (not shown) can be attached to the backside of the extender 1275 that can be releasably coupled to a mating coupler (not shown) disposed on the front side of the support strap in the same manner as described above for garment 1100. The couplers can be, for example, snap connectors (e.g., a male and female snap connectors), a hook and loop coupling, VELCRO, buttons, etc.

A coupling member 1256 is coupled to the outer panel 1260 in the same or similar manner as the portion 356 is coupled to the outer panel 360 described above. For example, a portion of the outer panel 1260 can be passed through an opening of the coupling member 1256 and secured to the coupling member 1256 with stitching. The coupling member 1256 includes a hook 1258 that can be selectively received within a loop of the extender 1275 to releasably couple the outer panel 1260 to the shoulder strap 1206 and the support strap 1280 as shown, for example, in FIG. 21B.

During normal use of the garment 1200, the outer panel 1260 (e.g., left outer panel 1264 and right outer panel 1262) can be releasably coupled to the shoulder straps 1206 and the support straps 1280 by coupling the coupling member 1256 to extender 1275 at the top loop 1276. In this position, the outer panel 1260 is sized and positioned to be closest to the user's breast. To accommodate a wearable breast pump or milk collection device, the user can adjust the size and position of the outer panel 1260 relative to the user's breast and relative to the shoulder straps 1206 by releasably coupling the coupling member 1256 to a selected one of the loops 1277, 1278, 1279. For example, as shown in FIG. 21B, the loop portion 1258 of the coupling member 1256 is inserted through and coupled to the loop 1278 and the loop 1279 is tucked behind the outer panel 1260. Thus, in this position, the outer panel 1260 is extended further from the shoulder strap 1206 and thus can provide more space for the insertion of a wearable breast pump or collection device.

Figure 20A:
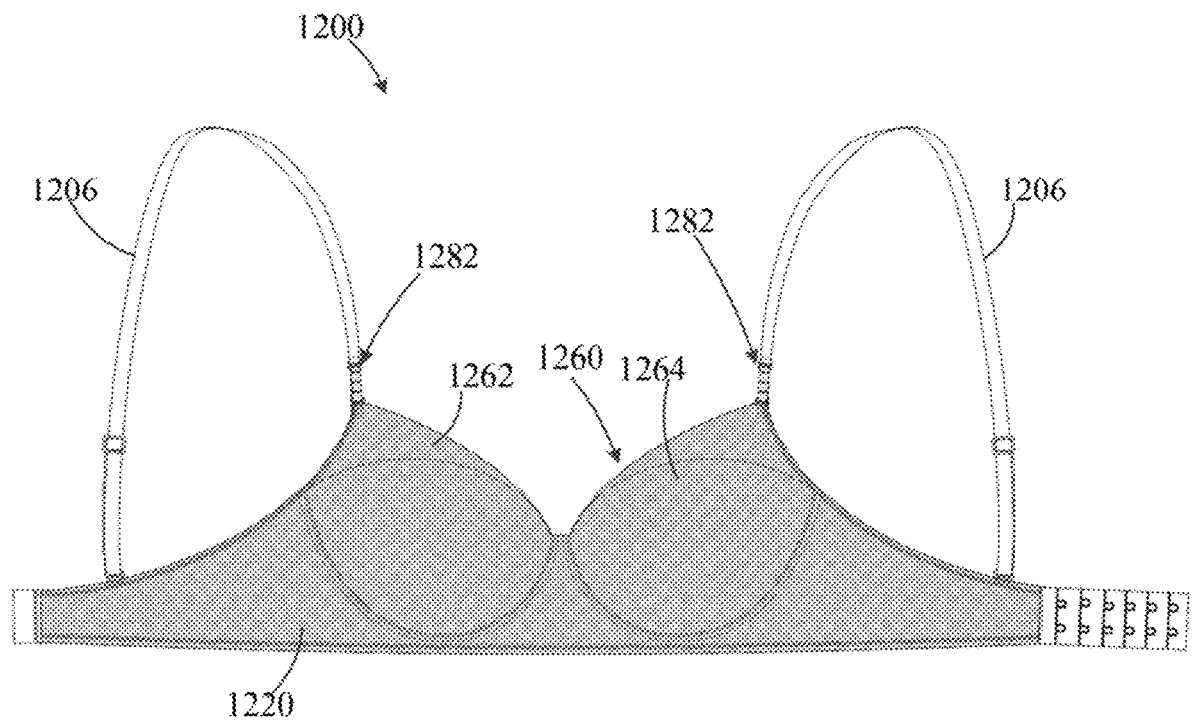
FIG. 20A is a font view of a garment, according to another embodiment.
Figure 20B:
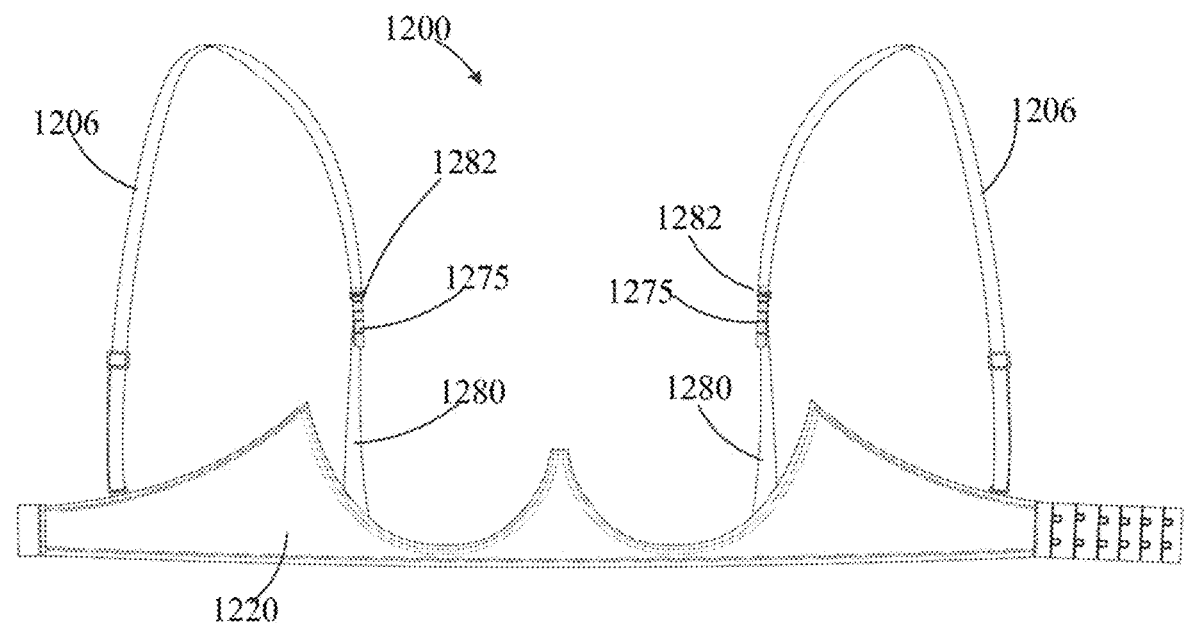
FIG. 20B is a front view of the garment of FIG. 20A shown with the outer panel removed for illustrative purposes.

If a user wants to gain full access to one or both breasts to, for example, nurse, the outer panel 1260 can be detached from the extender 1275, as shown, for example, in FIGS. 20B and 21A. As also shown in FIGS. 20B and 21A, the extender 1275 remains secured to the clip 1282. As with previous embodiments, with the outer panel 1260 detached from the shoulder straps 1206 and support straps 1280, the garment 1200 can still be held in place on the body of the wearer via the shoulder straps 1206 and support straps 1280. Although the garment 1200 is shown in FIG. 20B with the outer panel 1260 completely removed, it should be understood that the outer panel 1260 would remain attached to the back panel 1220 when the coupling member 1256 is detached from the extender 1275.

Figure 23B:
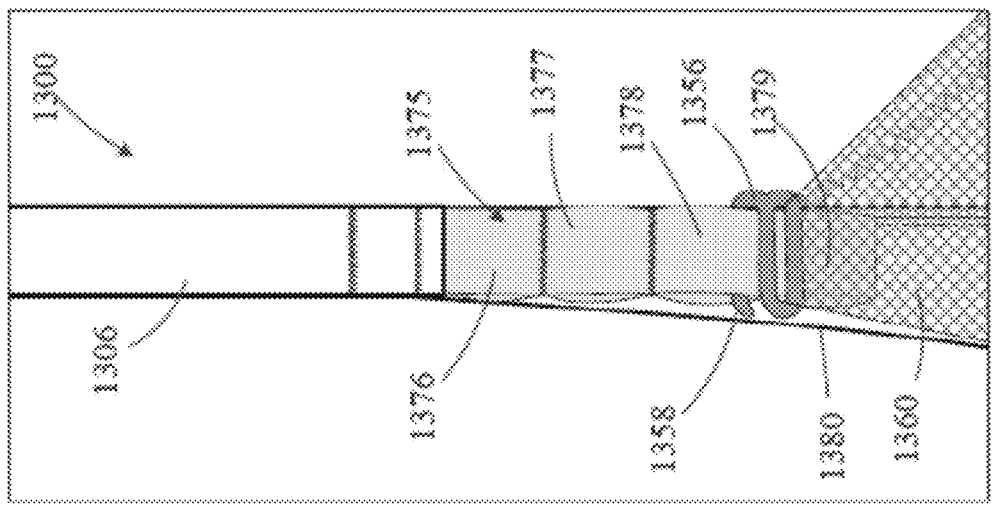
FIG. 23B is a front view of a portion of the garment of FIG. 23A shown with the outer panel attached to the extender.
Figure 23A:
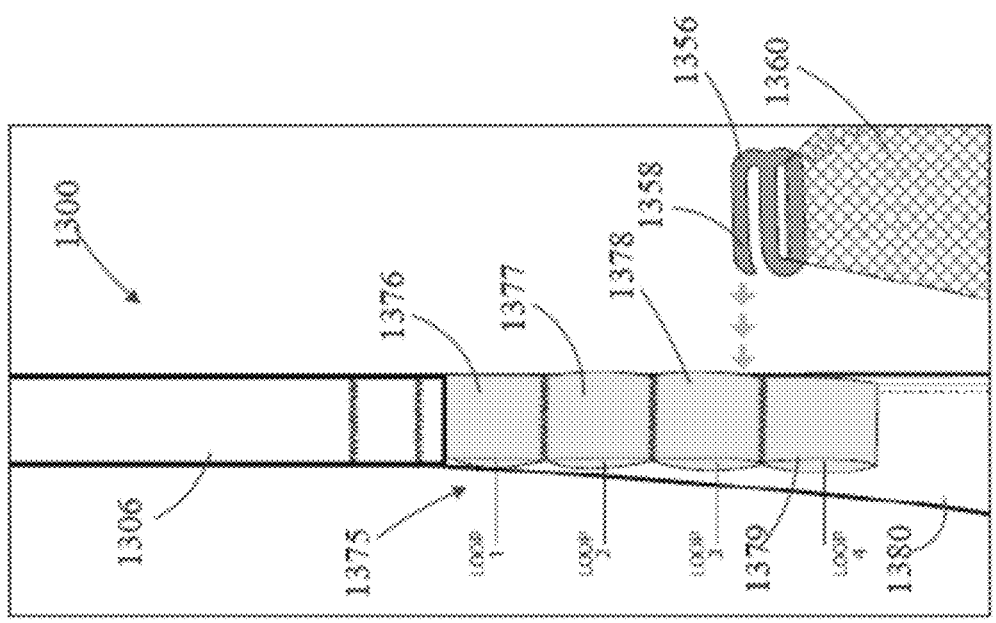
FIG. 23A is a front view of a portion of a garment, according to another embodiment, shown with the outer panel detached from the extender.
Figure 23D:
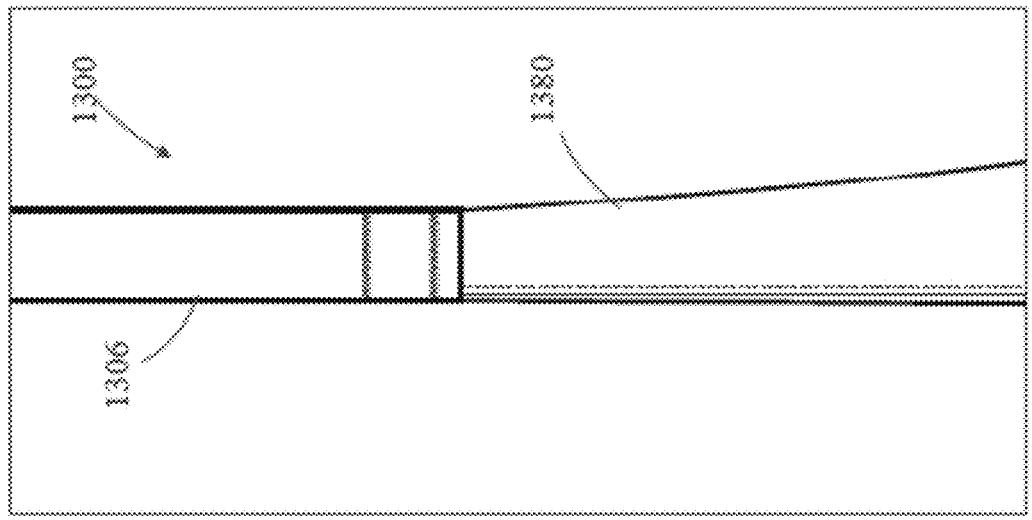
FIG. 23D is a back view of a portion of the garment of FIG. 23A showing the shoulder strap attached to the support strap.
Figure 23C:
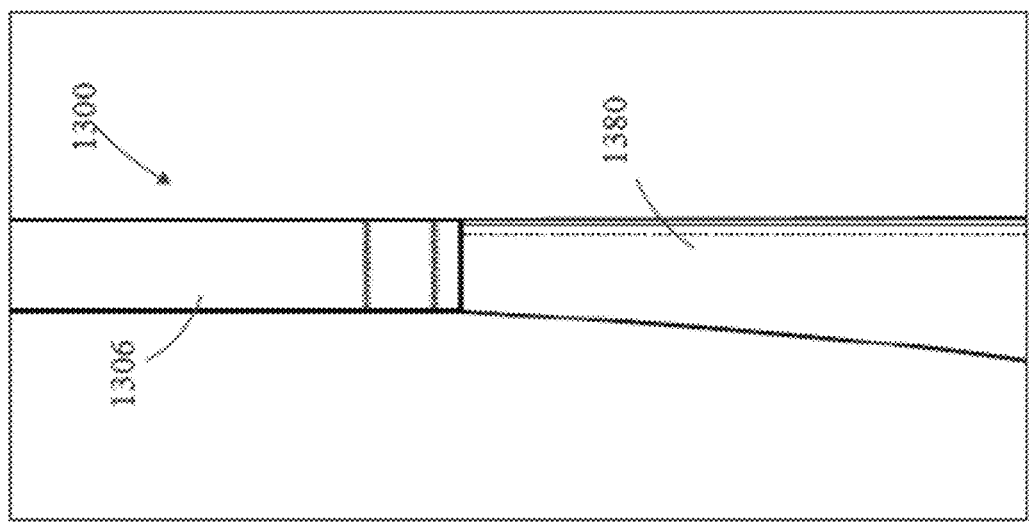
FIG. 23C is a front view of a portion of the garment of FIG. 23A shown with the extender removed for illustrative purposes.

FIGS. 23A-23C illustrate a portion of another embodiment of a garment that can be worn with a wearable breast pump or wearable milk collection device. The garment 1300 can include components that are the same or similar in structure and/or function to any of the garments described herein. For example, the garment 1300 can include an outer panel 1360, a support strap 1380 (best shown in FIGS. 23C and 23D), shoulder straps 1306 and a back panel (not shown). The outer panel 1360, support straps 1380, shoulder straps 1306 and back panel can be the same or similar in construction and function as the outer panel 1060, support straps 1080, shoulder straps 1006 and back panel 1020, respectively, and therefore, some features and details are not described with reference to this embodiment. For example, the various components can be coupled together in the same manner as described above for previous embodiments.

As with the previous embodiment, the garment 1300 includes extenders 1375 coupled to the support straps 1380 and the shoulder straps 1306. The extenders 1375 can be constructed the same as or similar to the extenders 1175 and 1275 described above and can include multiple loops that can provide for selective adjustment of the releasable attachment of the outer panel 1360 to the shoulder strap 1306 and the support strap 1380. In this embodiment, as shown in FIGS. 23A and 23B, the extenders 1375 include four loops, 1376, 1377, 1378 and 1379, for selective coupling of the outer panel 1360 to the support strap 1380 and shoulder strap 1306. The loops 1376, 1377, 1378, 1379 can be formed and constructed of the same materials as described above for previous embodiments and the extender 1375 can include more or less loops, such as, for example, two, three, five, six, seven, eight, nine, ten, etc.

In this embodiment, the extender 1375, the support strap 1380 and the shoulder strap 1306 are coupled to each other with stitching. In other words, no clip (e.g., clip 1282) or engagement mechanism (e.g., engagement mechanism 1150) is used. For example, the extender 1375 can be stitched to the support strap 1380 and/or the shoulder strap 1306. Similarly, the support strap 1380 can be stitched to the shoulder strap 1306 and/or to the extender 1375. FIG. 23C illustrates the support strap 1380 coupled (e.g., sewn/stitched) to the shoulder strap 1306 with the extender 1375 removed for illustrative purposes and FIG. 23D is a hack view showing the support strap 1380 coupled (e.g., sewn/stitched) to the shoulder strap 1306. In alternative embodiments, the support strap 1381) can be coupled (e.g., sewn/stitched) to the extender 1375 as described above for garment 1200 (see, e.g., FIG. 22C) and the extender 1375 can be coupled (e.g., sewn/stitched) to the shoulder strap 1306. To further secure extender 1375 to the support strap 1380 and maintain its position, a first coupler 1392 can be attached to the backside of the extender 1375 that can be releasably coupled to a mating coupler (not shown) disposed on the front side of the support strap 1380, in the same manner as described for garment 1100. The couplers can be, for example, snap connectors (e.g., a male and female snap connectors), a hook and loop coupling, VELCRO, buttons, etc.

A coupling member 1356 is coupled to the outer panel 1360 in the same or similar manner as described above for coupling member 1256. For example, a portion of the outer panel 1360 can be passed through an opening of the coupling member 1356 and secured to the coupling member 1356 with stitching. The coupling member 1356 includes a hook 1358 that can be selectively received within a loop of the extender 1375 to releasably couple the outer panel 1360 to the shoulder strap 1306 and the support strap 1380 as shown, for example, in FIG. 23B.

During normal use of the garment 1300, the outer panel 1360 (e.g., the left outer panel and the right outer panel) can be releasably coupled to the shoulder straps 1306 and the support straps 1380 by coupling the coupling member 1356 to extender 1375 at the top loop 1376. In this position, the outer panel 1360 is sized and positioned to be closest to the user's breast. To accommodate a wearable breast pump or milk collection device, the user can adjust the size and position of the outer panel 1361) relative to the user's breast and relative to the shoulder straps 1306 by releasably coupling the coupling member 1356 to a selected one of the loops 1377, 1378, 1379. For example, as shown in FIG. 23B, the loop 1358 of the coupling member 1356 is inserted through and coupled to the loop 1378 and the loop 1379 is tucked behind the outer panel 1360. Thus, in this position, the outer panel 1360 is extended further from the shoulder strap 1306 and thus can provide more space for the insertion of a wearable breast pump or collection device.

If a user wants to gain full access to one or both breasts to, for example, nurse, the outer panel 1360 can be detached from the extender 1375, as shown in FIG. 23A. As with previous embodiments, with the outer panel 1360 detached from the shoulder straps 1306 and support straps 1380, the garment 1300 can still be held in place on the body of the wearer via the shoulder straps 1306 and support straps 1380.

FIGS. 24-30D illustrate various views and components of a garment 1400 that can be used with a wearable breast pump or wearable milk collection device. As described above, such wearable breast pumps or milk collection devices are placed in contact with a user's breast between the breast and the outer panel of the garment (e.g., bra). In this embodiment, the garment 1400 includes a pumping panel that can be removably attached to the outer panel of the garment 1400 as described in more detail below. This allows the garment to be worn be a user with or without the pumping panel attached.

Figure 24:
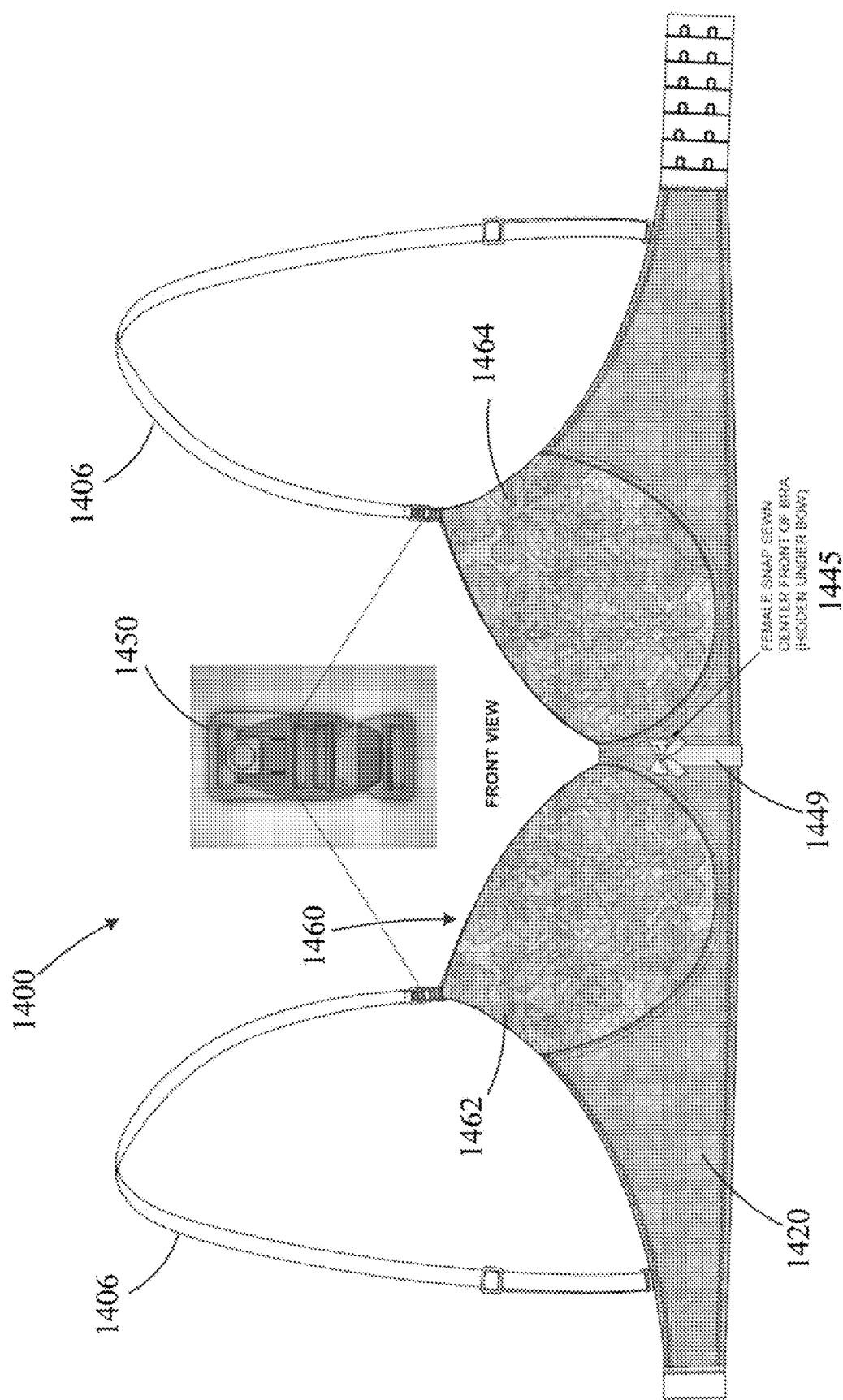
FIG. 24 is a front view of a garment, according to another embodiment.
Figure 25:
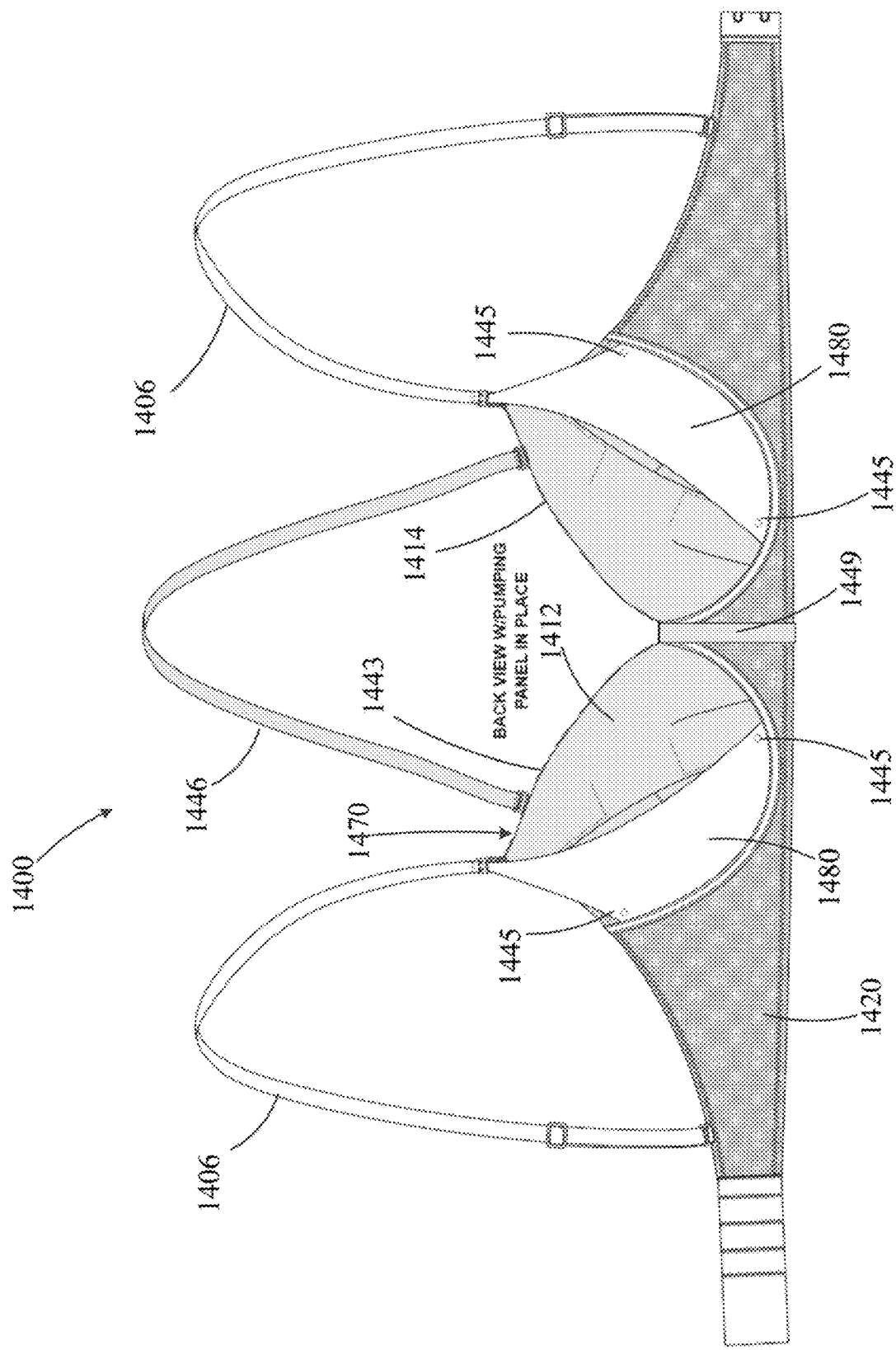
FIG. 25 is a back view of the garment of FIG. 24.
Figure 27:
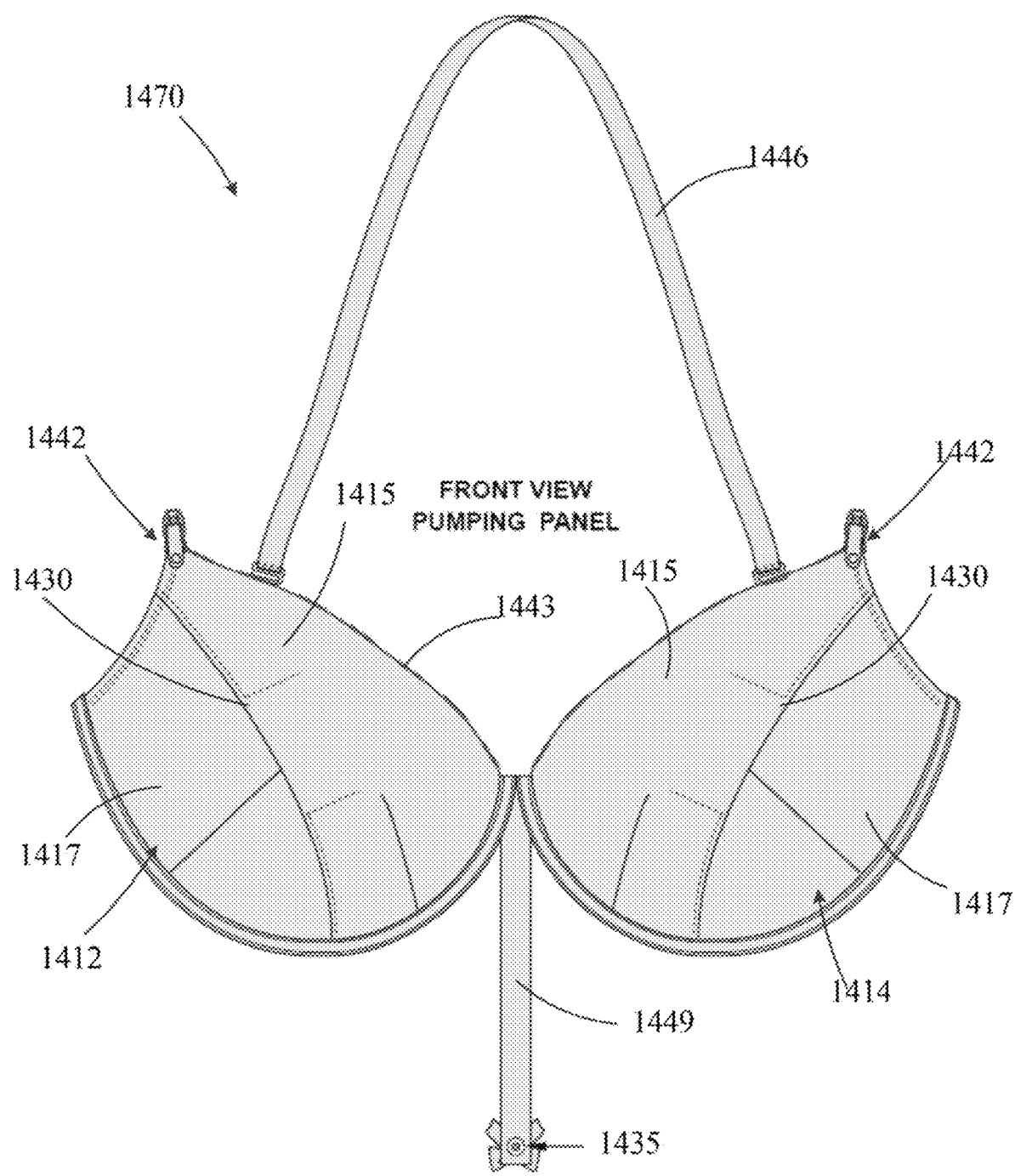
FIG. 27 is a front view of the pumping panel of the garment of FIG. 24.
Figure 28:
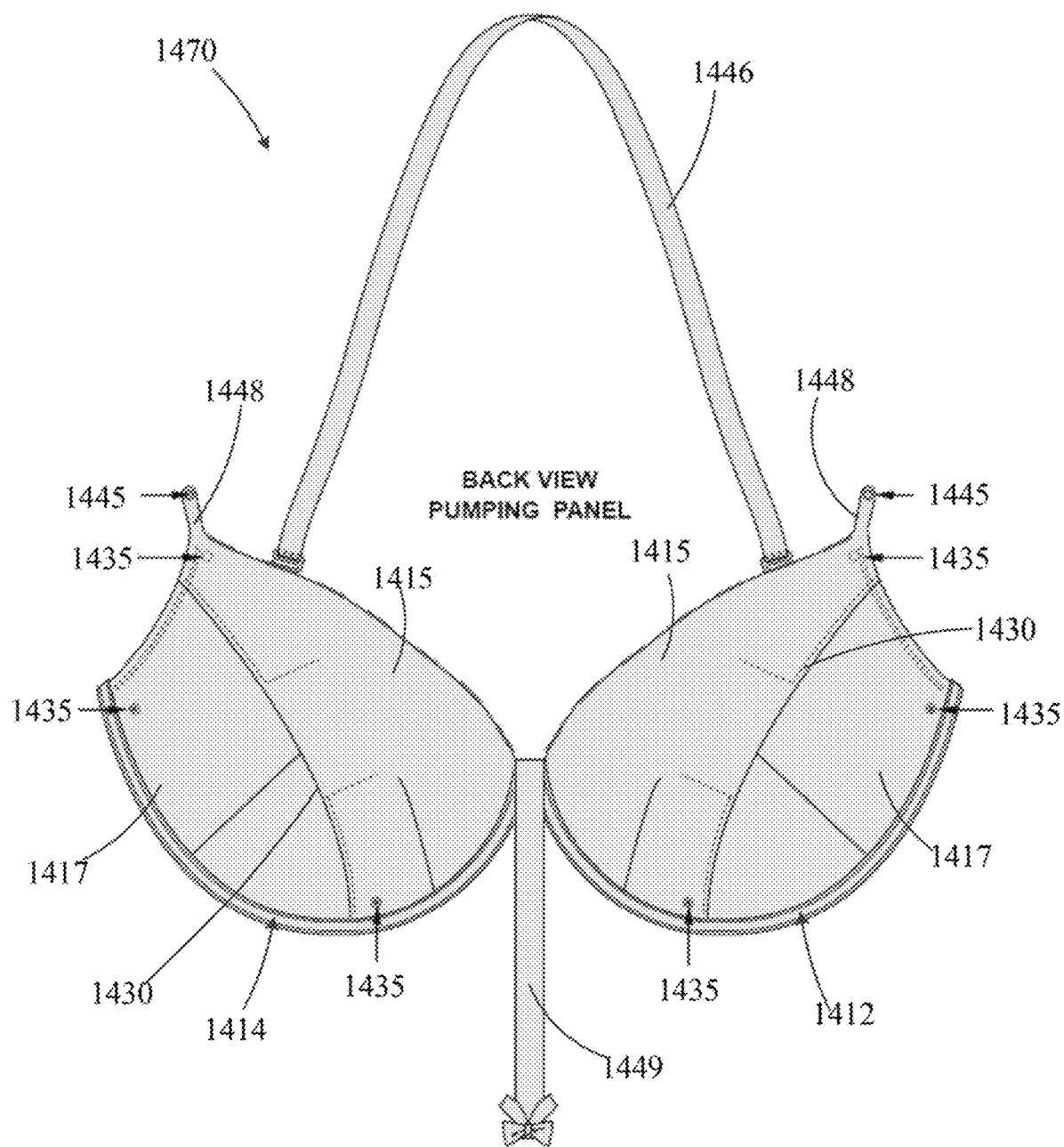
FIG. 28 is a back view of the pumping panel of the garment of FIG. 24.

FIG. 24 is a front view of the garment 1400 and FIG. 25 is a back view of the garment 1400. The garment 1400 can include the same or similar components and/or functions as any of the garments described herein. For example, the garment 1400 includes an outer panel 1460, an inner pumping panel 1470 (shown in FIG. 25), a back panel 1420, two support straps 1480 (shown in FIG. 25) and two shoulder straps 1406. The garment 1400 can also include a center or neck strap 1446 that can be removably coupled to the inner pumping panel 1470 as shown in FIGS. 25, 27 and 28. Each shoulder strap 1406 can be coupled to the outer panel 1460, the inner panel 1470, and a support strap 1480 via an engagement mechanism 1450 (also referred to herein as a "clasp"). The outer panel 1460, support straps 1480, shoulder straps 1406 and back panel 1420 can be the same or similar in construction and function as, for example, the outer panel 1060, support straps 1080, shoulder straps 1006 and back panel 1020, respectively, and therefore, some features and details are not described with reference to this embodiment. For example, the various components can be coupled together in the same manner as described above for previous embodiments. In some embodiments, the various components are coupled together via stitching.

The inner panel 1470 and the outer panel 1460 can each include one or more panels each formed with one or more layers of material. As shown, for example, in FIGS. 24 and 26, the outer panel 1460 includes a right outer panel 1462 and a left outer panel 1464. As shown, for example, in FIGS. 25, 27 and 28, the inner panel 1470 includes a right inner panel 1412 and a left inner panel 1414. The right inner panel 1412 and the left inner panel 1414 can be shaped and sized for coverage of a wearer's right breast and left breast, respectively. Each of the right inner panel 1412 and the left inner panel 1414 can include a first portion 1415 and a second portion 1417 that are coupled together such that a portion is unattached and can define an opening 1430 (see, e.g., FIGS. 27 and 28) between the first portion 1415 and the second portion 1417. In some embodiments, the first portion 1415 and the second portion 1417 can include an overlapping portion Which can define the opening 1430. The first portion 1415 and the second portion 1417 can be separated by, for example, moving the first portion 1415 and the second portion 1417 away from each other, thereby creating the opening 1430 and providing access to the user's breast. A breast pump can then be inserted through the opening 1430 and the inner pumping panel 1470 can help support the breast pump (e.g., pump 290 described above) during milk extraction.

Additionally, as shown in FIGS. 25, 27 and 28, the inner panel 1470 can include one or more holes 1443 defined in an upper edge of the inner panel 1470. For example, the inner panel 1470 can define the holes 1443 and/or the holes 1443 can be defined by a separate component coupled to the inner panel 1470. As described for previous embodiments, a center strap 1446 can be attached to the inner panel 1470 via selective releasable engagement with any of the holes 1443. The center strap 1446 can be the same or similar in structure and/or function to the center strap 246 described above.

The support straps 1480 can be coupled on a first end to the back panel 1420 and on a second end to one of the shoulder straps 1406 via the engagement mechanism 1450 as described in more detail below. In alternative embodiments, the support strap 1480 can be attached to a lower band of the garment 1400 rather than to the back panel 1420. Each of the shoulder straps 1406 can have a first end coupled to the support strap 1480 (via the engagement mechanism 1450) and a second end coupled to the back panel 1420, with for example, sewing/stitching. The outer panel 1460 can be attached to the back panel 1420, for example, along a bottom edge of the outer panel 1460, via, for example, sewing/stitching. In this embodiment, the inner pumping panel 1470 can be removably coupled to the shoulder straps 1406 (and therefore the back panel 1470), via a coupling mechanism 1442 that is removably coupleable to the engagement mechanism 1450 and is also removably coupleable to the support straps 1480 and the back panel 1420 with coupling members, as described in more detail below.

Figure 29:
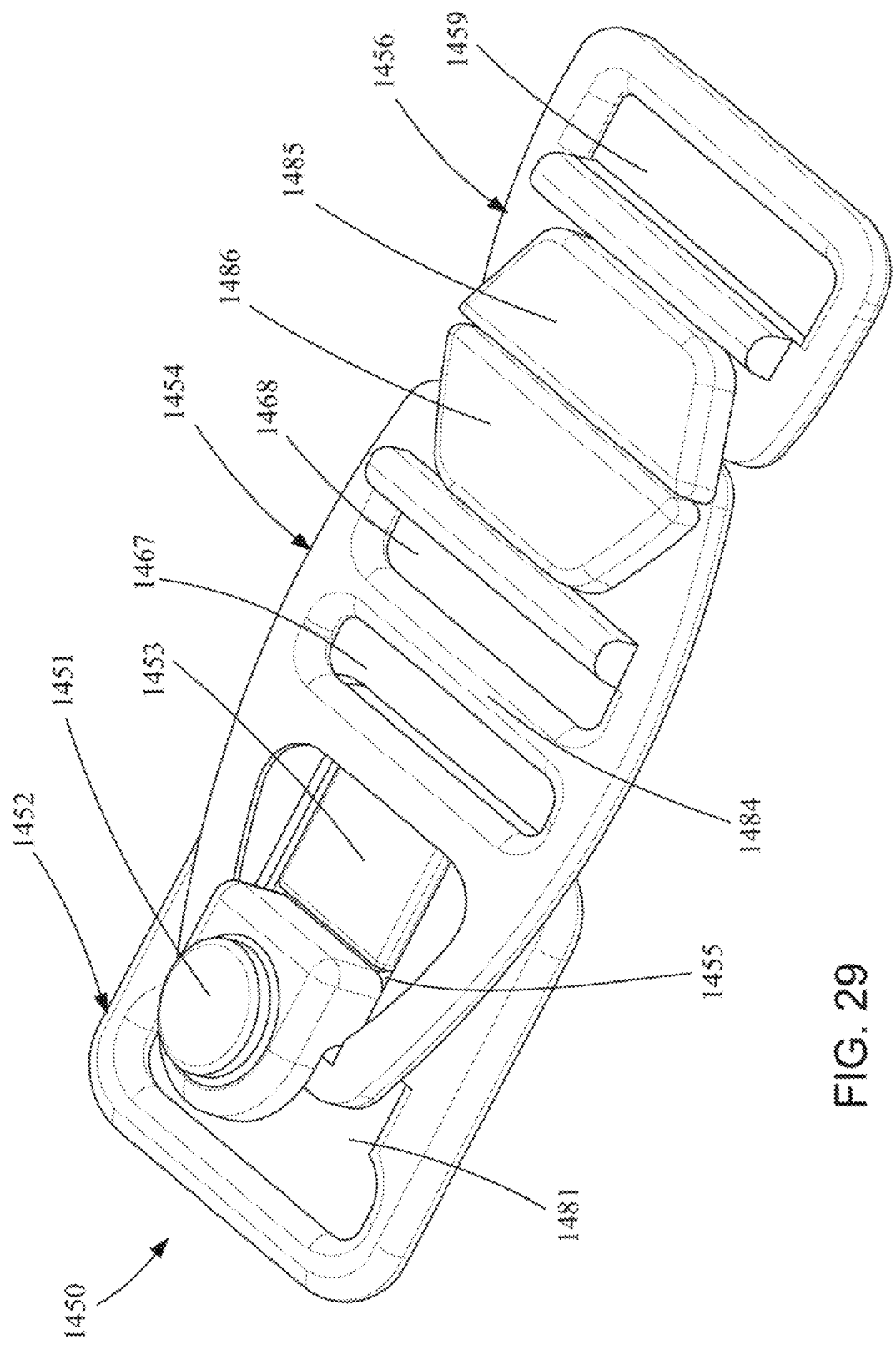
FIG. 29 is an enlarged perspective view of an engagement mechanism of the garment of FIG. 24.
Figure 30B:
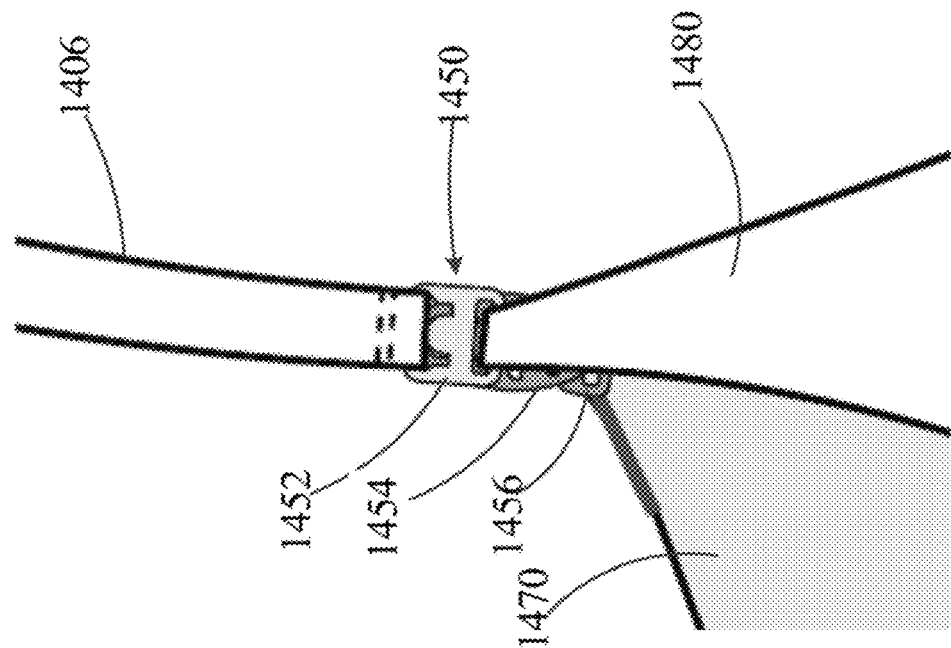
FIG. 30B is an enlarged hack view of a portion of the garment of FIG. 25.
Figure 30A:
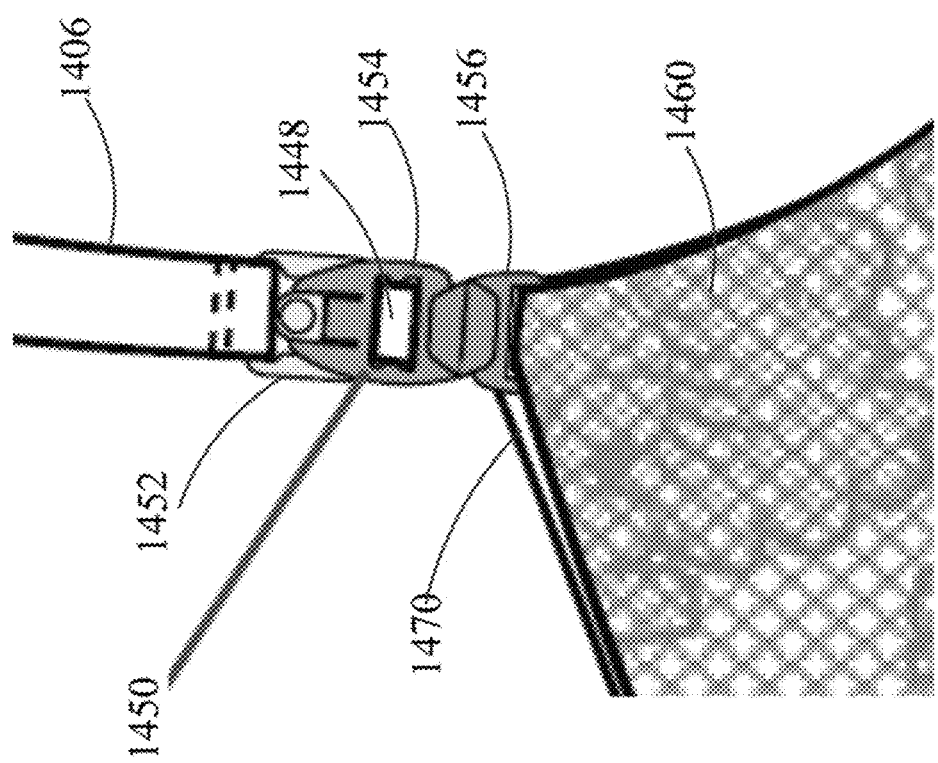
FIG. 30A is an enlarged front view of a portion of the garment of FIG. 24.
Figure 30D:
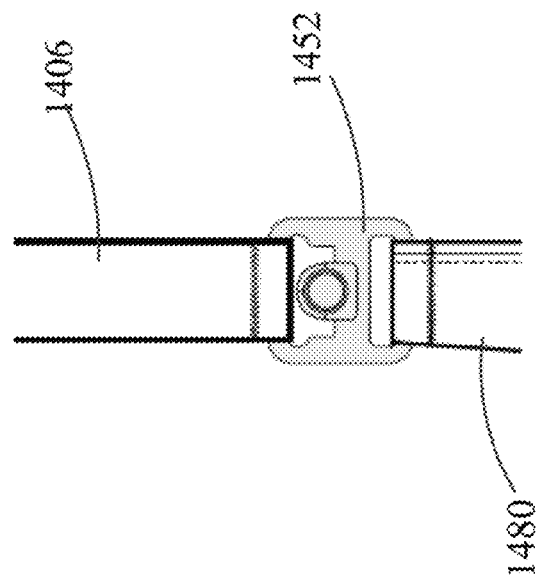
FIG. 30D is an enlarged front view of a portion of the garment of FIG. 24 illustrating the attachment of a support strap to the engagement mechanism.
Figure 30C:
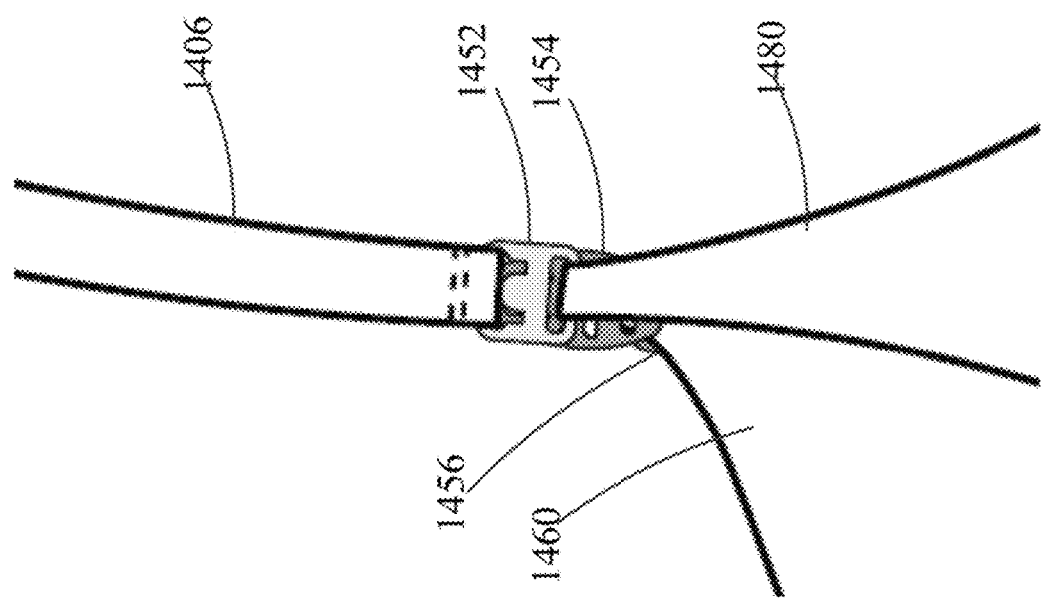
FIG. 30C is an enlarged back view of a portion of the garment of FIG. 26 with the inner pumping panel removed.

The engagement mechanism 1450 can be the same or similar in structure and/or function as the engagement mechanism 850 described above. As best shown in FIG. 29, which is an enlarged view of the engagement mechanism of FIG. 24, the engagement mechanism 1450 can include a first portion 1452, a second portion 1454, and a third portion 1456. The first portion 1452 can be releasably engageable with the second portion 1454, and the second portion 1454 can be releasably engageable with the third portion 1456. The first portion 1452 can include an extension portion 1451, a first opening 1481, and a second opening (not visible in FIG. 24B) (see, e.g., 883 in FIG. 14B) on an opposite side of the extension portion 1451 than the first opening 1481. The second portion 1454 can include a tab portion 1453, a first opening 1455, a securement bar 1484, a second opening 1467, a third opening 1468, and an engagement portion 1085. The third portion 1456 can include an engagement portion 1486 and an opening 1459.

The first portion 1452 of the engagement mechanism 1450 is coupled to one of the shoulder straps 1406 with, for example, stitching. For example, an end portion of one of the shoulder straps 1406 can be looped through the first opening 1481 and attached to itself (e.g., with stitching) such that a top portion of the first portion 1452 is secured within the loop of the shoulder strap 1406 (see e.g., FIGS. 30A-30D). Additionally, the first portion 1452 can receive a portion of the support strap 1480 through the second opening 1483 such that the support strap 1480 can be secured to the first portion 1452 (see, e.g., FIGS. 30B-30D). For example, an end portion of the support strap 1480 can be looped through the second opening of the first portion 1452 and attached to itself (e.g., with stitching) such that a bottom portion the first portion 1452 is secured within the loop of the support strap 1480 (see e.g., FIGS. 30B-30D).

As described above, in this embodiment, rather than permanently stitching the inner pumping panel 1470 to the second portion 1454 of the engagement member 1450, the inner pumping panel 1470 can be removably coupled to the second portion 1454 of the engagement mechanism 1450. As shown in FIGS. 27 and 28, each of the right and left panels 1414 and 1412 includes a coupling mechanism 1442 that includes a first coupling member 1445 attached to an end portion of an extended tab 1448 and a mating second coupling member 1435 attached to a portion of the panels 1462 and 1464. To removably couple the inner pumping panel 1470 to the engagement mechanism 1450, the extended tab 1448 is inserted through the opening 1468 of the second portion 1454 and passing the extended tab 1448 around the securement bar 1484, out through opening 1467, and folding it upon itself such that the coupling member 1445 can be coupled to the coupling member 1435 as shown in FIG. 27. FIG. 27 illustrates the extended tab 1448 folded over and the coupling members 1445 and 1435 coupled together without the second portion 1464 of the engagement mechanism 1450 shown for illustrative purposes.

Figure 26:
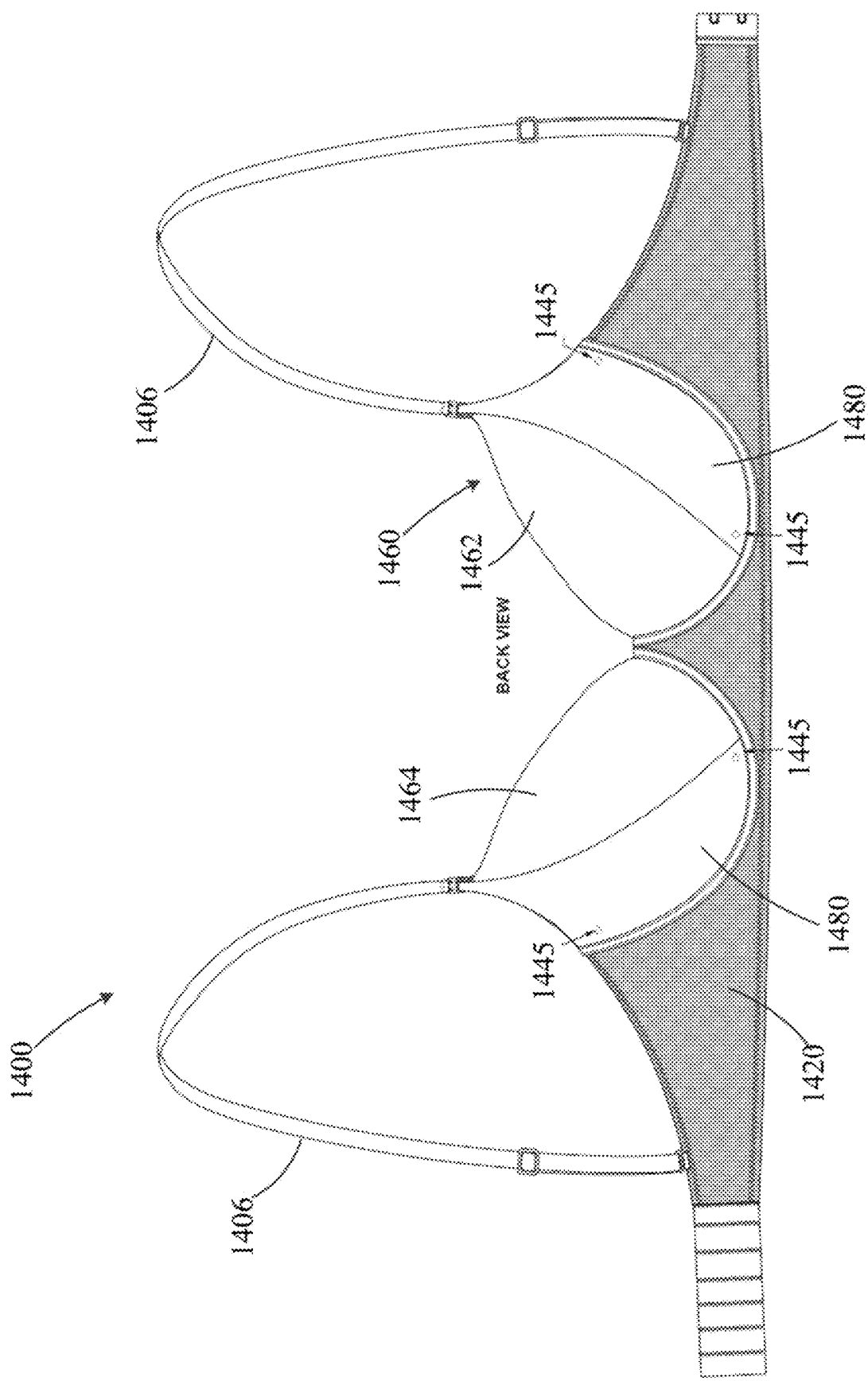
FIG. 26 is a back view of the garment of FIG. 24 with the inner pumping panel removed.

To removably couple the inner panel 1470 to the support straps 1480, the panels 1412 and 1414 of the inner panel 1470 include coupling members 1445 disposed on a back side of the panels 1412 and 1414 that can be removably coupled to corresponding coupling members 1445 disposed on a front side of the support panels 1480. FIGS. 25 and 26 show the back side of the support straps 1480 and indicate where the coupling members 1445 are disposed thereon, and FIG. 28 illustrates the back side of the inner panel 1470 and indicates where the coupling members 1435 are disposed thereon. In addition, the inner panel 1470 includes a coupling strap 1449 that extends from a center portion of the inner panel and has a coupling member 1435 disposed thereon, as shown in FIGS. 27 and 28. The coupling strap 1449 can wrap around the back panel 1420 (as shown in FIG. 25) and the coupling member 1435 disposed thereon can be coupled to a corresponding coupling member 1445 (not visible) disposed on a front side of the back panel 1420. FIG. 24 indicates where the coupling member 1435 is hidden underneath a bow on the coupling strap 1449.

In some embodiments, the coupling members 1445 and 1435 can be, for example, a female and male snap connector, respectively. It should be understood that in alternative embodiments, the coupling members 1445 can be a female snap connector and the coupling members 1435 can be a male snap connector, and vice versa. In addition, other types of coupling members can alternatively be used such as, for example, hook and loop fasteners such as VELCRO, or buttons, hooks, etc. The coupling members 1445 and 1435 can be attached to the inner panel 1470, outer panel 1460 and support straps 1480 by, for example, sewing or stitching.

In this embodiment, the outer panel 1460 can be attached to the third portion 1456 of the engagement mechanism 1450 in the same or similar manner as described for previous embodiments. More specifically, a portion of each of the panels 1462 and 1464 of the outer panel 1460 can pass through the opening 1459 of the third portion 1456 and looped over a bottom portion of the second portion 1456 of the engagement mechanism 1450 and then attached to itself (e.g., sewn or stitched) in a similar manner as how the support straps 1480 are attached to the second portion 1454 (see, e.g., FIG. 30A).

As with previous embodiments (e.g., engagement mechanism 850), the extension portion 1451 of the first portion 1452 can be shaped and sized to be inserted through the first opening 1455 of the second portion 1454 to releasably couple the second portion 1454 to the first portion 1452 and, therefore, releasably couple the inner panel 1470 (when the inner panel 1470 is coupled to the second portion 1454) to the support strap 1480 and shoulder straps 1406 (both attached to the first portion 1452) similarly as described above for previous embodiments. The tab portion 1453 of the second portion 1454 can be shaped and sized such that, when the extension portion 1451 of the first portion 1452 is received through the first opening 1455 of the second portion 1454, the tab portion 1453 contacts or engages the extension portion 1451 and such that it is flexed or clicked into locking engagement with the first portion 1452. In some embodiments, the tab portion 1453 can be sufficiently elastic such that as the second portion 1054 is moved into engagement with the first portion 1452, the tab portion 1453 can bend slightly and then snap into locking engagement.

Similarly, the engagement portion 1486 of the third portion 1456 can be releasably engaged with the engagement portion 1485 of the second portion 1454. Although the engagement portion 1486 and the engagement portion 1485 are shown as being formed in the interlocking shapes shown in FIG. 29, the engagement portion 1486 and the engagement portion 1485 can include any suitable releasably interlocking shapes.

As described above, the first portion 1452 and the second portion 1454 of the engagement mechanism 1450 can be engaged/coupled to couple the inner panel 1470 to the support strap 1480 and the shoulder straps 1406 (when the inner panel 1470 is coupled to the second portion 1454). The coupling members 1435 on the inner panel 1470 can be coupled to the corresponding coupling members 1445 on the support straps 1480 and back panel 1420. Additionally, the third portion 1456 can be coupled to the second portion 1454 via engagement of the engagement portion 1486 with the engagement portion 1485 to couple the outer panel 1460 (i.e., the panels 1462 and 1464) to the inner panel 1470 (i.e., panels 1412 and 1414) and the shoulder straps 1406 such that the outer panel 1460 substantially covers the inner panel 1470 as shown in FIG. 24. Although the outer panel 1460 is shown as covering the entire inner panel 1470 in FIG. 24, in some embodiments, the outer panel 1460 can be shaped and sized to only cover a portion of the inner panel 1470.

In use, the garment 1400 can be worn by a wearer and if access to a breast of the wearer is desired, such as for breast pumping, the outer panel 1460 (e.g., the right outer panel 1462 and/or the left outer panel 1464) can be detached from the inner panel 1470 (e.g., the right inner panel 1412 and/or the left inner panel 1414) by detaching or uncoupling the third portion 1456 from the second portion 1454 of the engagement mechanism 1450 and the outer panel 1460 can be moved (e.g., folded down) such that the inner panel 1470 is accessible. As described above, the first portion 1415 and the second portion 1417 of the inner panel 1470 (e.g., of the right inner panel 1412 and/or the left inner panel 1414) can be separated (e.g., stretched or folded) to create an opening 1430 through which the wearer's breast is accessible and a portion of a breast pump can be inserted. If further access to the breast of the wearer is desired, the inner panel 1470 can be detached from the shoulder straps 1406 by removing/detaching the second portion 1454 of the engagement mechanism 1450 from the first portion 1452 of the engagement mechanism 1450. The inner panel 1470 can also optionally be decoupled from the support straps 1480 by decoupling the coupling members 1445 and 1435. When desired, the inner panel 1470 and the outer panel 1460 can be reattached to shoulder strap 1406 by recoupling the second portion 1454 to the first portion 1452 of the engagement mechanism 1450, and recoupling the third portion 1456 to the second portion 1454 of the engagement mechanism 1450. In some embodiments, the outer panel 1460 and the inner panel 1470 can be detached from the shoulder straps 1406 simultaneously by detaching the second portion 1454 from the first portion 1452 but not detaching the third portion 1456 from the second portion 1454.

As described above, the garment 1400 can also be used with the inner panel 1470 completely removed from the garment 1400. In such a use, if desired, the outer panel 1460 can be detached from the shoulder straps 1406 and folded or moved downward to expose and gain access to one or both breast. For example, the third portion 1456 of the engagement mechanism 1450 can be detached from the second portion 1454 of the engagement mechanism 1450.

FIGS. 31-35 illustrate various views and components of a garment 1500 that is similar to the garment 1400 and can be used with a wearable breast pump or wearable milk collection device. As described above, such wearable breast pumps or milk collection devices are placed in contact with a user's breast between the breast and the outer panel of the garment (e.g., bra). In this embodiment, the garment 1500 includes a pumping panel that can be removably attached to the outer panel and the support straps of the garment 1500, and entirely removed, as described in more detail below. This allows the garment to be worn by a user with or without the pumping panel attached.

Figure 31:
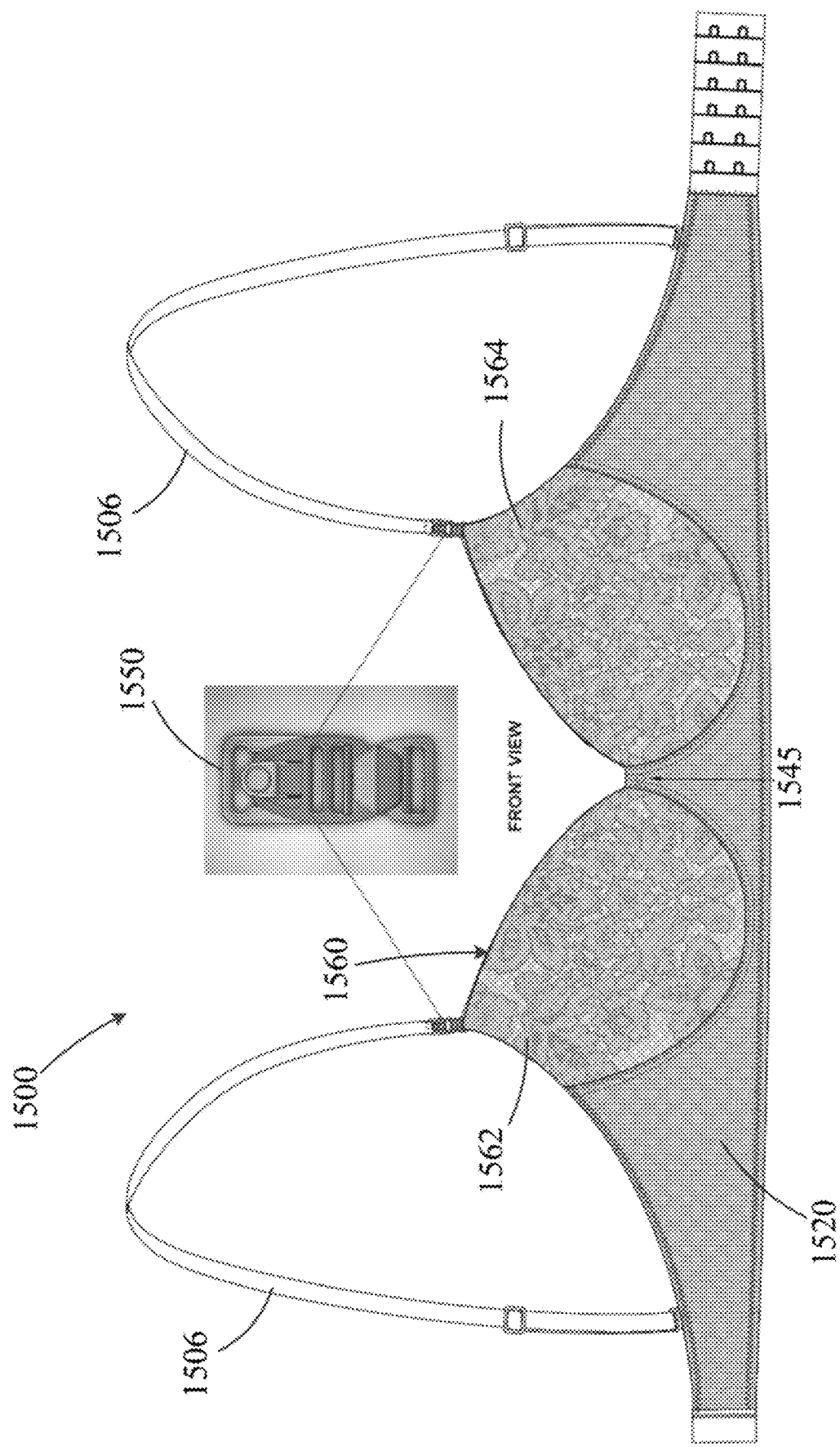
FIG. 31 is a front view of a garment, according to another embodiment.
Figure 32:
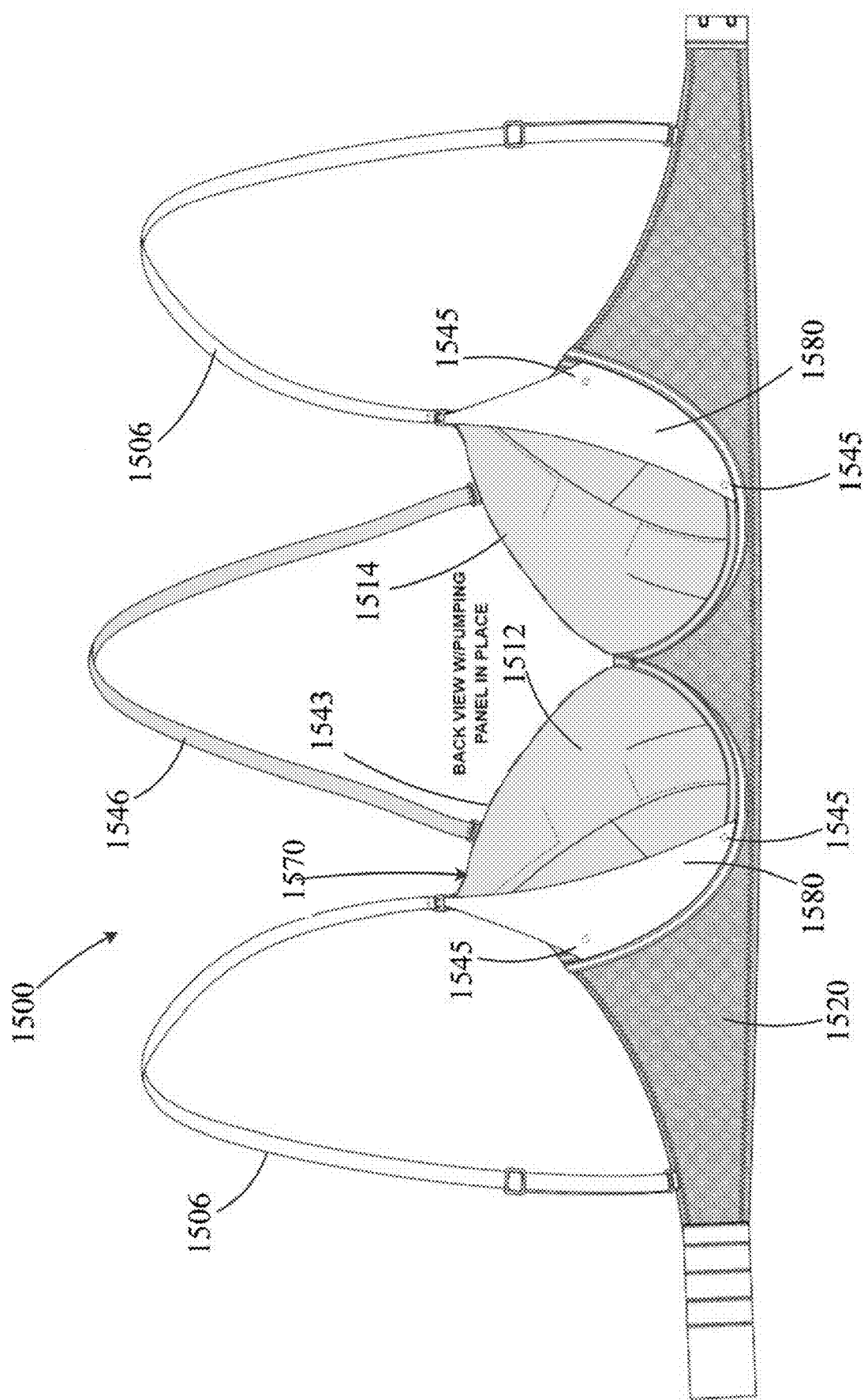
FIG. 32 is a back view of the garment of FIG. 31.
Figure 34:
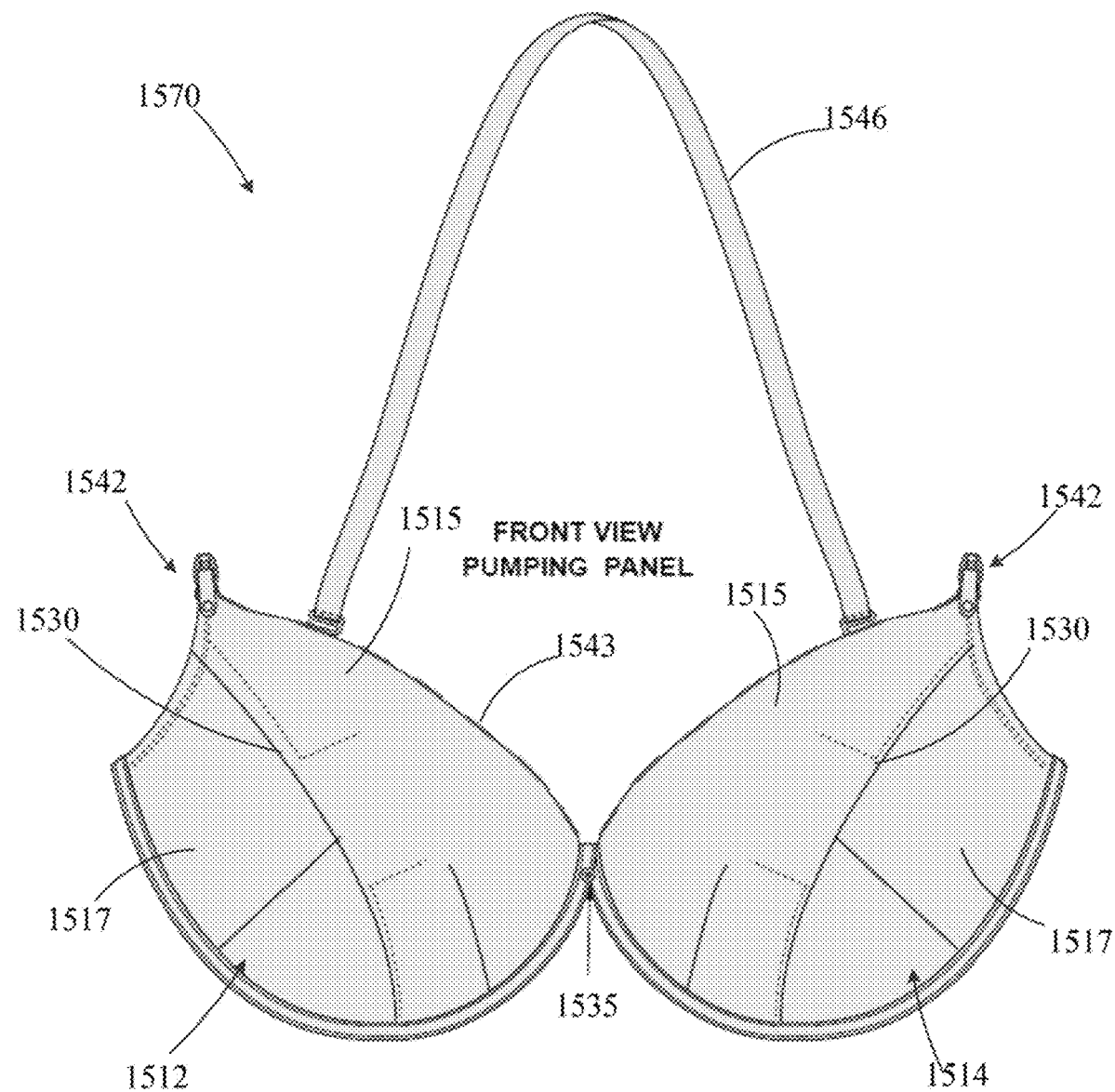
FIG. 34 is a front view of the pumping panel of the garment of FIG. 31.
Figure 35:
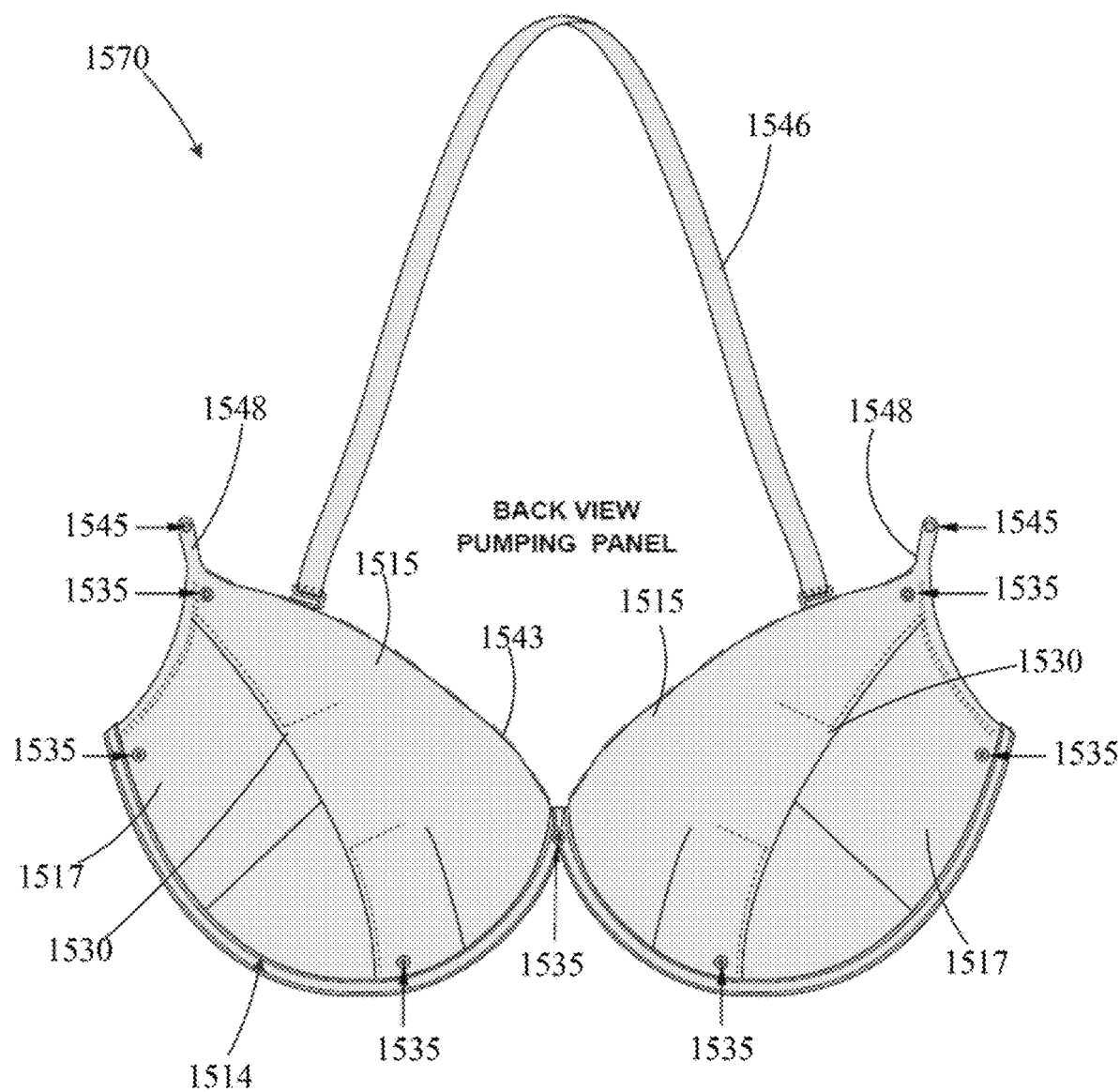
FIG. 35 is a back view of the pumping panel of the garment of FIG. 31.

FIG. 31 is a front view of the garment 1500 and FIG. 32 is a back view of the garment 1500. The garment 1500 can include the same or similar components and/or functions as any of the garments described herein. For example, the garment 1500 includes an outer panel 1560, an inner pumping panel 1570 (also referred to as inner panel 1570) (shown in FIG. 32), a back panel 1520, two support straps 1580 (shown in FIG. 32) and two shoulder straps 1506. The garment 1500 can also include a center or neck strap 1546 that can be removably coupled to the inner pumping panel 1570 as shown in FIGS. 32, 34 and 35. Each shoulder strap 1506 can be coupled to the outer panel 1560, the inner panel 1570, and a support strap 1580 via an engagement mechanism 1550 (also referred to herein as a "clasp"). The outer panel 1560, support straps 1580, shoulder straps 1506 and back panel 1520 can be the same or similar in construction and function as, for example, the outer panel 1060, support straps 1080, shoulder straps 1006 and back panel 1020, respectively, and therefore, some features and details are not described with reference to this embodiment. For example, the various components can be coupled together in the same manner as described above for previous embodiments. In some embodiments, the various components are coupled together via stitching.

The inner panel 1570 and the outer panel 1560 can each include one or more panels each formed with one or more layers of material. As shown, for example, in FIGS. 31 and 33, the outer panel 1560 includes a right outer panel 1562 and a left outer panel 1564. As shown, for example, in FIGS. 32, 34 and 35, the inner panel 1570 includes a right inner panel 1512 and a left inner panel 1514. The right inner panel 1512 and the left inner panel 1514 can be shaped and sized for coverage of a wearer's right breast and left breast, respectively. Each of the right inner panel 1512 and the left inner panel 1514 can include a first portion 1515 and a second portion 1517 that are coupled together such that a portion is unattached and can define an opening 1530 (see, e.g., FIGS. 34 and 35) between the first portion 1515 and the second portion 1517. In some embodiments, the first portion 1515 and the second portion 1517 can include an overlapping portion which can define the opening 1530. The first portion 1515 and the second portion 1517 can be separated by, for example, moving the first portion 1515 and the second portion 1517 away from each other, thereby creating the opening 1530 and providing access to the user's breast. A breast pump can then be inserted through the opening 1530 and the inner pumping panel 1570 can help support the breast pump (e.g., pump 290 described above) during milk extraction.

Additionally, as shown in FIGS. 32, 34 and 35, the inner panel 1570 can include one or more holes 1543 defined in an upper edge of the inner panel 1570. For example, the inner panel 1570 can define the holes 1543 and/or the holes 1543 can be defined by a separate component coupled to the inner panel 1570. As described for previous embodiments, a center strap 1546 can be attached to the inner panel 1570 via selective releasable engagement with any of the holes 1543. The center strap 1546 can be the same or similar in structure and/or function to the center strap 246 described above.

The support straps 1580 can be coupled on a first end to the back panel 1520 and on a second end to one of the shoulder straps 1506 via the engagement mechanism 1550 in the same manner as described above for garment 1400. In alternative embodiments, the support strap 1580 can be attached to a lower band of the garment 1500 rather than to the back panel 1520. Each of the shoulder straps 1506 can have a first end coupled to the support strap 1580 (via the engagement mechanism 1550) and a second end coupled to the back panel 1520, with for example, sewing/stitching. The outer panel 1560 can be attached to the back panel 1520, for example, along a bottom edge of the outer panel 1560, via, for example, sewing/stitching. In this embodiment, the inner pumping panel 1570 can be removably coupled to the shoulder straps 1506 (and therefore the back panel 1520), via a coupling mechanism 1542 that is removably coupleable to the engagement mechanism 1550 and is also removably coupleable to the support straps 1580 and the back panel 1520 with coupling members, as described in more detail below.

The engagement mechanism 1550 can be the same or similar in structure and/or function as the engagement mechanism 850 and the engagement mechanism 1450 described above. The engagement mechanism 1550 can be coupled to the various components of the garment 1500 in the same manner as described above for garment 1400

As described above, in this embodiment, rather than permanently stitching the inner pumping panel 1570 to the engagement member 1550, the inner pumping panel 1570 can be removably coupled to the engagement mechanism 1550. As shown in FIGS. 34 and 35, each of the right and left panels 1514 and 1512 includes a coupling mechanism 1542 that includes a first coupling member 1545 attached to an end portion of an extended tab 1548 and a mating second coupling member 1535 attached to a portion of the panels 1562 and 1564. To removably couple the inner pumping panel 1570 to the engagement mechanism 1550, the extended tab 1548 is removably coupled to engagement mechanism 1550 in the same manner as described for extended tab 1448 and engagement mechanism 1450 by folding it upon itself such that the first coupling member 1545 can be coupled to the second coupling member 1535 as shown in FIG. 34.

Figure 33:
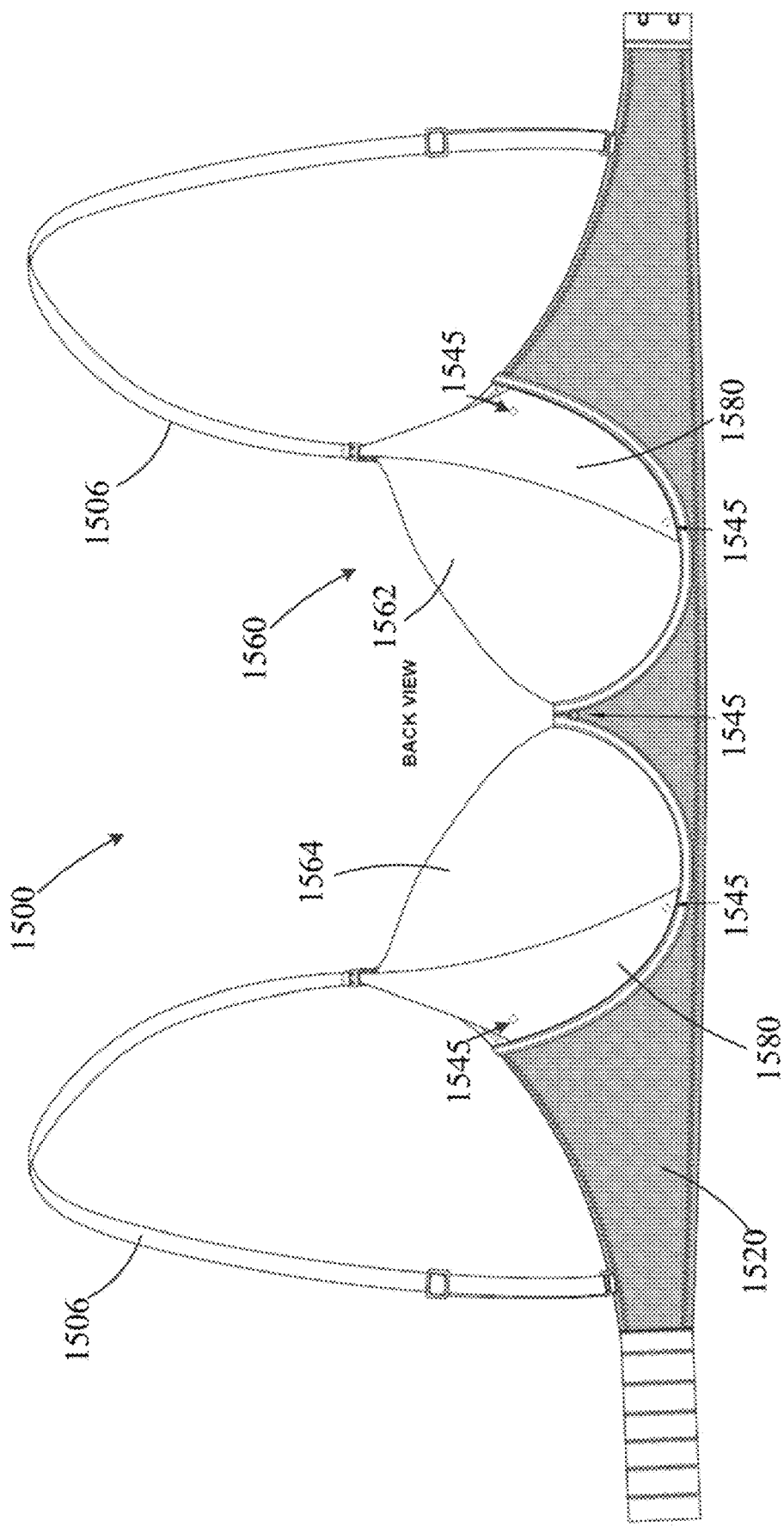
FIG. 33 is a back view of the garment of FIG. 31 with the inner pumping panel removed.

To removably couple the inner panel 1570 to the support straps 1580, the panels 1512 and 1514 of the inner panel 1570 include coupling members 1535 disposed on a back side of the panels 1512 and 1514 that can be removably coupled to corresponding coupling members 1545 disposed on a front side of the support panels 1580. FIGS. 32 and 33 show the back side of the support straps 1580 and indicate where the coupling members 1545 are disposed thereon (but on the front side of the support straps 1580), and FIG. 35 illustrates the back side of the inner panel 1570 and indicates where the coupling members 1535 are disposed thereon. In addition, in this embodiment, the inner panel 1570 includes a coupling member 1535 disposed on a front side at a center portion between the panels 1515, as shown in FIG. 34. The coupling member 1535 can be removably coupled to a coupling member 1545 disposed on the back panel 1520 at a center portion between the panels 1562 and 1564, as shown, for example, in FIG. 33, to couple the inner panel 1570 to the back panel 1520.

In some embodiments, the coupling members 1545 and 1535 can be, for example, a female and male snap connector, respectively. It should be understood that in alternative embodiments, the coupling members 1545 can be a female snap connector and the coupling members 1535 can be a male snap connector, and vice versa. In addition, other types of coupling members can alternatively be used such as, for example, hook and loop fasteners such as VELCRO, or buttons, hooks, etc. The coupling members 1545 and 1535 can be attached to the inner panel 1570, outer panel 1560, back panel, and support straps 1580 by, for example, sewing or stitching.

In this embodiment, the outer panel 1560 can be attached to the engagement mechanism 1550 in the same or similar manner as described for previous embodiments. Further, as described above, the inner panel 1570 can be coupled to the support strap 1580 and the shoulder straps 1506 (when the inner panel 1570 is coupled to the engagement mechanism 1550). The coupling members 1535 on the inner panel 1570 can be coupled to the corresponding coupling members 1545 on the support straps 1580 and back panel 1520. Additionally, the outer panel 1560 (i.e., the panels 1562 and 1564) can be coupled to the inner panel 1570 (i.e., panels 1512 and 1514) and the shoulder straps 1506 such that the outer panel 1560 substantially covers the inner panel 1570 as shown in FIG. 31. Although the outer panel 1560 is shown as covering the entire inner panel 1570 in FIG. 31, in some embodiments, the outer panel 1560 can be shaped and sized to only cover a portion of the inner panel 1570.

In use, the garment 1500 can be worn by a wearer and if access to a breast of the wearer is desired, such as for breast pumping, the outer panel 1560 (e.g., the right outer panel 1562 and/or the left outer panel 1564) can be detached from the inner panel 1570 (e.g., the right inner panel 1512 and/or the left inner panel 1514) in the same manner as described above for garment 1400. As described above, the first portion 1515 and the second portion 1517 of the inner panel 1570 (e.g., of the right inner panel 1512 and/or the left inner panel 1514) can be separated (e.g., stretched or folded) to create an opening 1530 through which the wearer's breast is accessible and a portion of a breast pump can be inserted. If further access to the breast of the wearer is desired, the inner panel 1570 can be detached from the shoulder straps 1506 as described above for garment 1400. The inner panel 1570 can also optionally be decoupled from the support straps 1580 by decoupling the coupling members 1545 and 1534. When desired, the inner panel 1570 and the outer panel 1560 can be reattached to shoulder strap 1506 in the same manner as described above for garment 1400. In some embodiments, the outer panel 1560 and the inner panel 1570 can be detached from the shoulder straps 1506 simultaneously.

As described above, the garment 1500 can also be used with the inner pumping panel 1570 completely removed from the garment 1500. In such a use, if desired, the outer panel 1560 can be detached from the shoulder straps 1506 and folded or moved downward to expose and gain access to one or both breast.

FIGS. 36-40C illustrate a garment 1600 according to yet another embodiment. In this embodiment, the garment 1600 can be similarly constructed as the garments described above, and in particular, the garments 1400 and 1500, and therefore some features are not described below in detail. The garment 1600 can be used with a wearable breast pump or wearable milk collection device. As described above, such wearable breast pumps or milk collection devices are placed in contact with a user's breast between the breast and the outer panel of the garment (e.g., bra). As with the previous embodiment, in this embodiment, the garment 1600 includes an inner pumping panel that can be removably attached to the outer panel and the support straps of the garment 1600, and entirely removed, as described in more detail below. This allows the garment to be worn by a user with or without the inner pumping panel attached. This embodiment also includes extenders that can be optionally used in place of the inner pumping panel similar to the extenders 1175 and 1275 described above for previous embodiments. The extenders in this embodiment are removable and can be used in place of the inner pumping panel to provide adjustability to support and fit a wearable pumping device. Thus, a user can either attach the inner pumping panel to use the garment for supporting a breast pump, or attach the extenders to adjust the cup size of the outer panel to be used when wearing a wearable breast pump.

Figure 36:
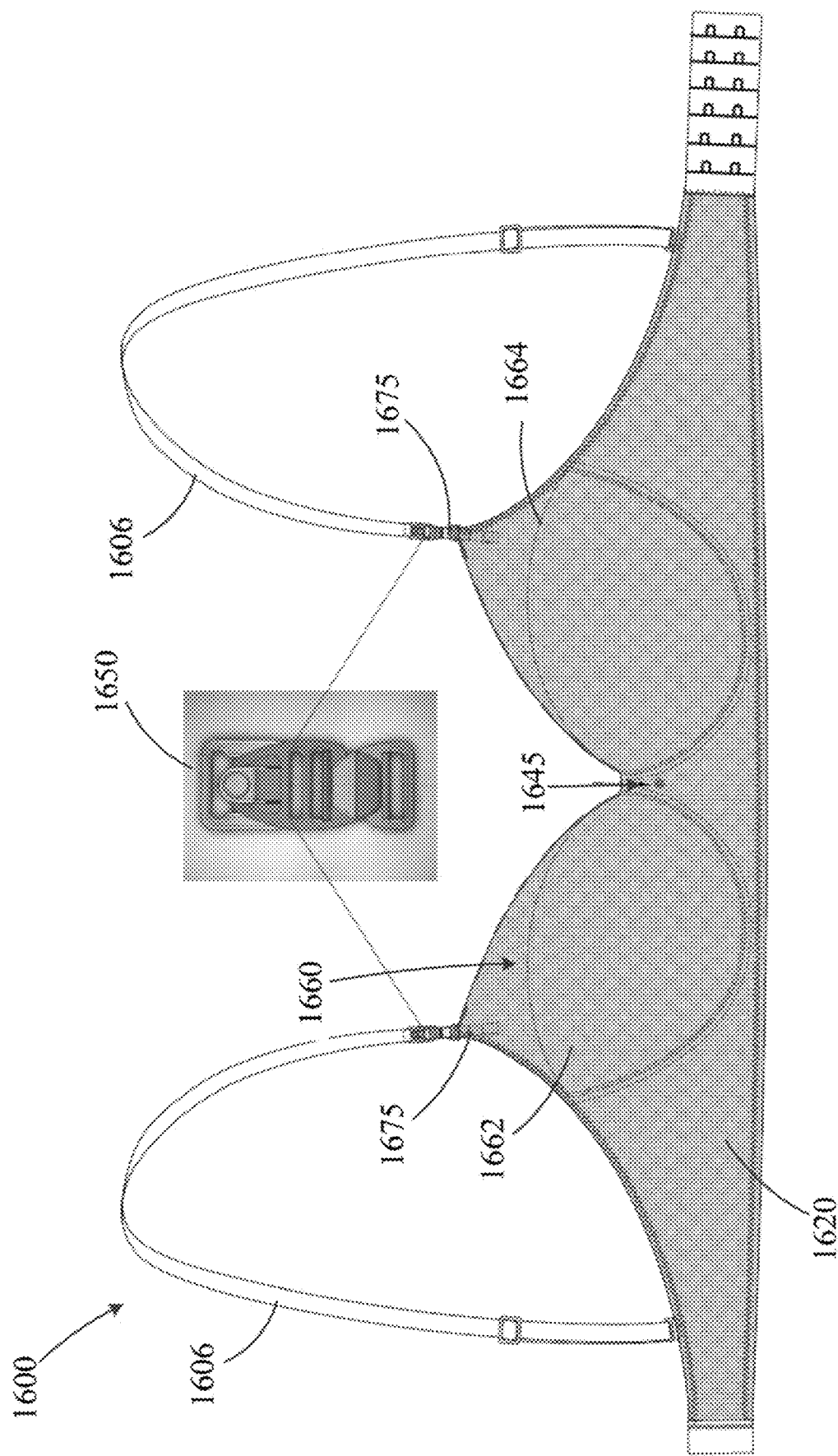
FIG. 36 is a front view of a garment and showing an enlarged view of an engagement mechanism, according to another embodiment.
Figure 37:
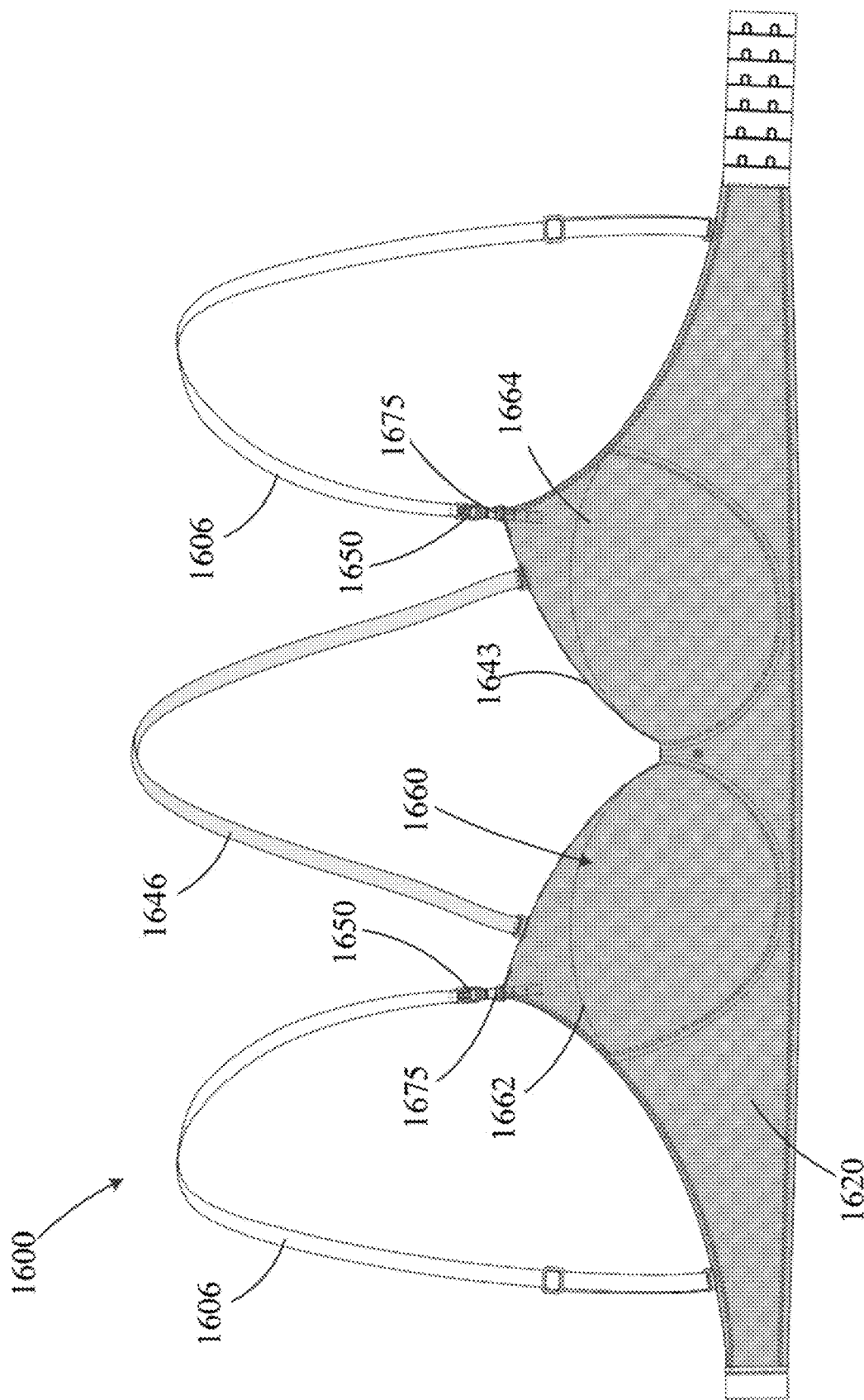
FIG. 37 is a front view of the garment of FIG. 36 showing a neck strap coupled to the outer panel.
Figure 38:
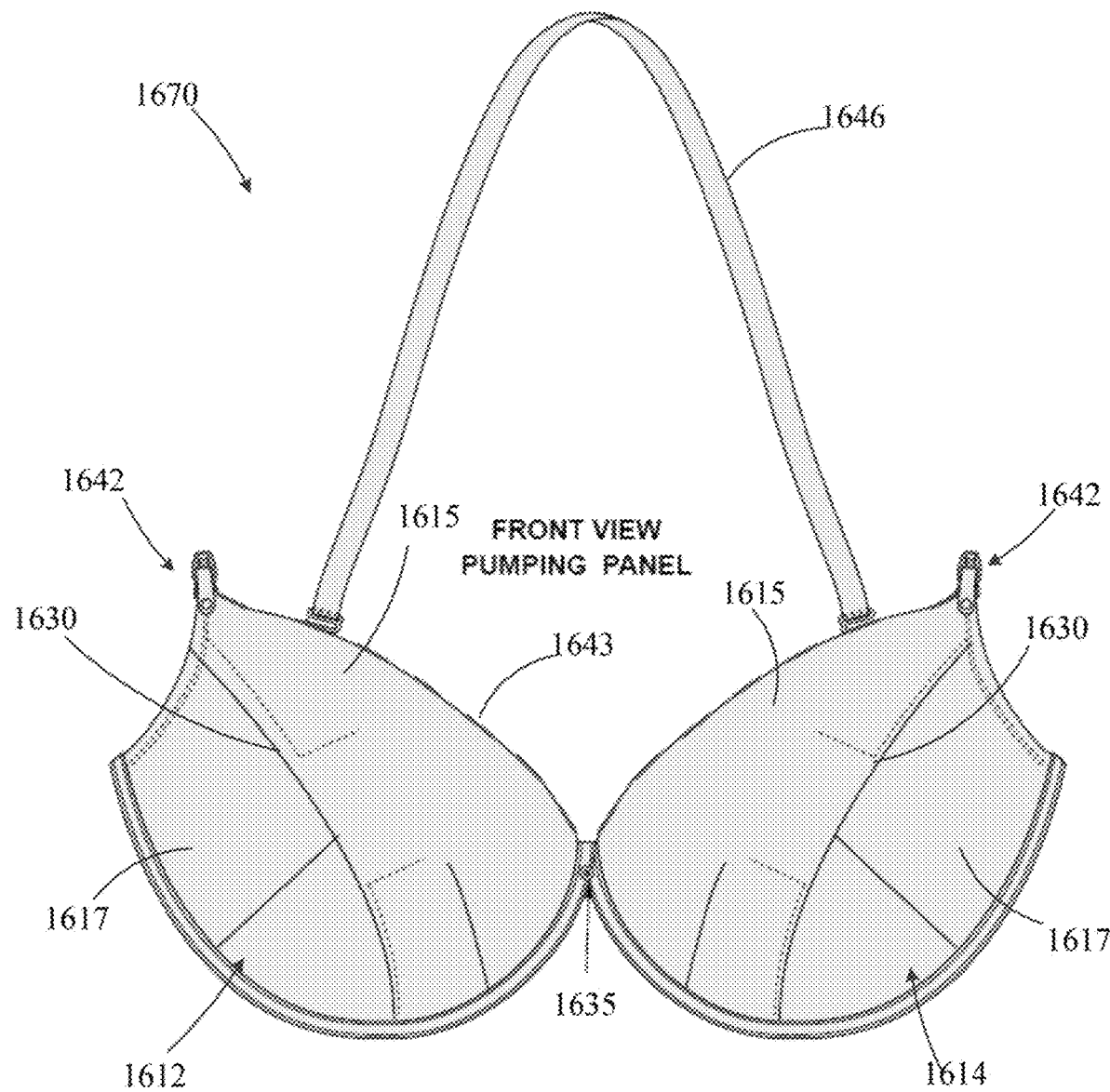
FIG. 38 is a front view of an inner pumping panel of the garment of FIG. 36.
Figure 39C:
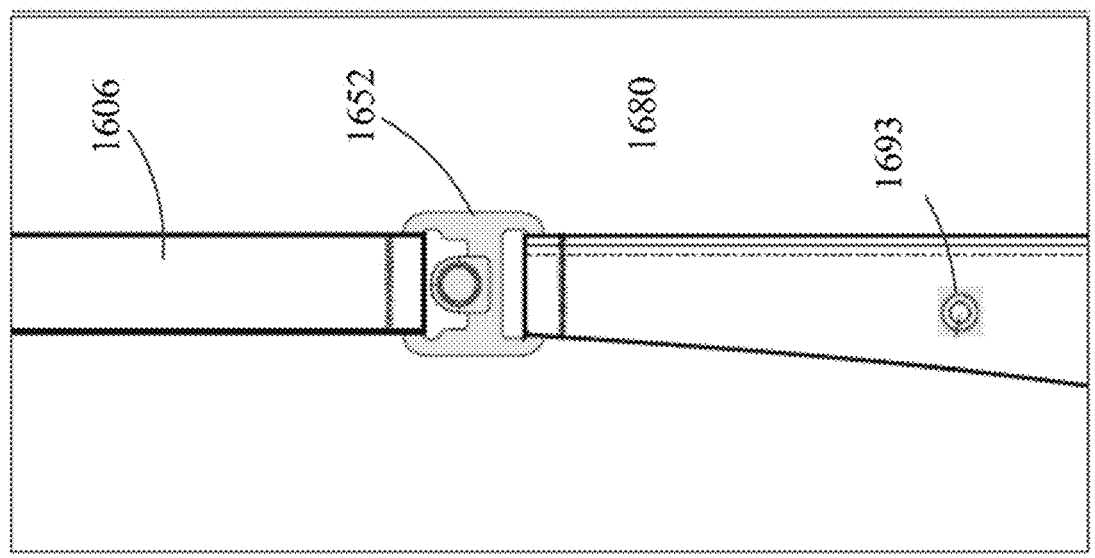
FIG. 39C is a front view of a portion of the garment of FIG. 36 with the third portion and second portion of the engagement mechanism detached from the first portion of the engagement mechanism and thus, the outer panel and inner panel detached from the support strap and shoulder strap.

FIGS. 36 and 37 are each a front view of the garment 1600, with FIG. 36 illustrating an enlarged view of an engagement mechanism 1650 (also referred to herein as a "clasp"), and FIG. 37 illustrating a neck support 1646 that can be used with the garment 1600. The garment 1600 can include the same or similar components and/or functions as any of the garments described herein. The garment 1600 includes an outer panel 1660, an inner pumping panel 1670 (also referred to as inner panel 1670) (shown in FIG. 38), a back panel 1620, two support straps 1680 (only a portion of a support strap 1680 is shown in FIGS. 39A-39C) and two shoulder straps 1606. The garment 1600 can also include the center or neck strap 1646 that can be removably and selectively coupled to a portion of the inner pumping panel 1670 as shown in FIG. 38 or removably and selectively coupled to a portion of the outer panel 1660 as shown in FIG. 37. Each shoulder strap 1606 can be coupled to the outer panel 1660, the inner panel 1670, and a support strap 1680 via an engagement mechanism 1650 (also referred to herein as a "clasp"). The outer panel 1660, support straps 1680, shoulder straps 1606 and back panel 1620 can be the same or similar in construction and function as, for example, the outer panel 1060, support straps 1080, shoulder straps 1006 and back panel 1020, respectively, and therefore, some features and details are not described with reference to this embodiment. For example, the various components can be coupled together in the same manner as described above for previous embodiments. In some embodiments, the various components are coupled together via stitching.

The inner panel 1670 and the outer panel 1660 can each include one or more panels each formed with one or more layers of material. As shown, for example, in FIGS. 36 and 37, the outer panel 1660 includes a right outer panel 1662 and a left outer panel 1664. As shown, for example, in FIG. 38, the inner panel 1670 includes a right inner panel 1612 and a left inner panel 1614. The right inner panel 1612 and the left inner panel 1614 can be shaped and sized for coverage of a wearer's right breast and left breast, respectively. Each of the right inner panel 1612 and the left inner panel 1614 can include a first portion 1615 and a second portion 1617 that are coupled together such that a portion is unattached and can define an opening 1630 between the first portion 1615 and the second portion 1617. In some embodiments, the first portion 1615 and the second portion 1617 can include an overlapping portion which can define the opening 1630. The first portion 1615 and the second portion 1617 can be separated by, for example, moving the first portion 1615 and the second portion 1617 away from each other, thereby creating the opening 1630 and providing access to the user's breast. A breast pump can then be inserted through the opening 1630 and the inner pumping panel 1670 can help support the breast pump (e.g., pump 290 described above) during milk extraction.

Additionally, as shown in FIG. 38, the inner panel 1670 can include one or more holes or loops 1643 defined in an upper edge of the inner panel 1670. For example, the inner panel 1670 can define the holes 1643 and/or the holes 1643 can be defined by a separate component coupled to the inner panel 1670. The center strap 1646 can be attached to the inner panel 1670 via selective releasable engagement with any of the holes 1643. The center strap 1646 can be the same or similar in structure and/or function to the center strap 246 described above.

In this embodiment, the outer panel 1660 can also include one or more holes or loops 1643 defined in an upper edge of the outer panel 1660. As with the inner panel 1670, the outer panel 1660 can define the holes 1643 and/or the holes 1643 can be defined by a separate component coupled to the outer panel 1660. The center strap 1646 can be attached to the outer panel 1670 via selective releasable engagement with any of the holes 1643. The center strap 1646 can be the same or similar in structure and/or function to the center strap 246 described above.

The support straps 1680 can be coupled on a first end to the back panel 1620 and on a second end to one of the shoulder straps 1606 via the engagement mechanism 1650 in the same manner as described above for garment 1400. In alternative embodiments, the support strap 1680 can be attached to a lower band of the garment 1600 rather than to the back panel 1620. Each of the shoulder straps 1606 can have a first end coupled to the support strap 1680 (via the engagement mechanism 1650) and a second end coupled to the hack panel 1620, with for example, sewing/stitching. The outer panel 1660 can be attached to the back panel 1620, for example, along a bottom edge of the outer panel 1660, via, for example, sewing/stitching. In this embodiment, the inner pumping panel 1670 can be removably coupled to the shoulder straps 1606 (and therefore the back panel 1670), via a coupling mechanism 1642 that is removably coupleable to the engagement mechanism 1650 and is also removably coupleable to the support straps 1680 and the back panel 1620 with coupling members, in the same or similar manner as described above for inner panels 1470 and 1570.

The engagement mechanism 1650 can be the same or similar in structure and/or function as the engagement mechanism 850 and the engagement mechanism 1450 described above. As best shown in FIGS. 39A-39C, the engagement mechanism 1650 can include a first portion 1652, a second portion 1654, and a third portion 1656. The first portion 1652 can be releasably engageable with the second portion 1654, and the second portion 1654 can be releasably engageable with the third portion 1656. The first portion 1652, second portion 1654 and third portion 1656 can be configured the same as the respective portions of the engagement mechanisms 850 and 1450. The first portion 1652 of the engagement mechanism 1650 is coupled to one of the shoulder straps 1606 with, for example, stitching. The first portion 1652 is also coupled to a support strap 1680 in the same manner as described for previous embodiments.

As described above, in this embodiment, rather than permanently or fixedly coupling the inner pumping panel 1670 to the engagement mechanism 1650 with stitching, the inner pumping panel 1670 can be removably coupled to the engagement mechanism 1650. As shown in FIG. 38, each of the right and left panels 1614 and 1612 includes a coupling mechanism 1642 that can be used to removably couple the inner panel 1670 to the second portion 1654 (shown in FIGS. 39A and 39B) of the engagement mechanism 1650 in the same manner as described for inner panel 1570.

The inner panel 1670 can also be removably coupled to the support straps 1680 and the back panel 1620 with releasable coupling members (not shown) in the same or similar manner as described above for inner panels 1470 or 1570. Thus, as with the previous embodiment, the inner panel 1670 can be entirely removed from the garment 1600.

In this embodiment, the outer panel 1660 can be attached to the third portion 1656 of the engagement mechanism 1650 in the same or similar manner as described for previous embodiments and as shown in FIGS. 39A and 39B. Thus, the outer panel 1660 can be coupled to the support strap 1680 and the shoulder strap 1606 when the third portion 1656 is coupled to the second portion 1654 and the second portion 1654 is coupled to the first portion 1652. Additionally, if the inner panel 1670 is coupled to the support strap 1680 and shoulder strap 1606 (via the second portion 1654), the outer panel 1660 can be coupled to the inner panel 1670 such that the outer panel 1660 substantially covers the inner panel 1670.

As described above, in this embodiment, the garment 1600 can also include extenders 1675 that can be removably coupled to the second portion 1654 of the engagement mechanism 1650. For example, with the inner pumping panel being removable, if desired, a user can add the extenders 1675 in place of the inner pumping panel 1670 to use the garment when wearing a wearable breast pump or to otherwise provide a larger cup size for the outer panel 1660.

Figures 40A, 40B, 40C:
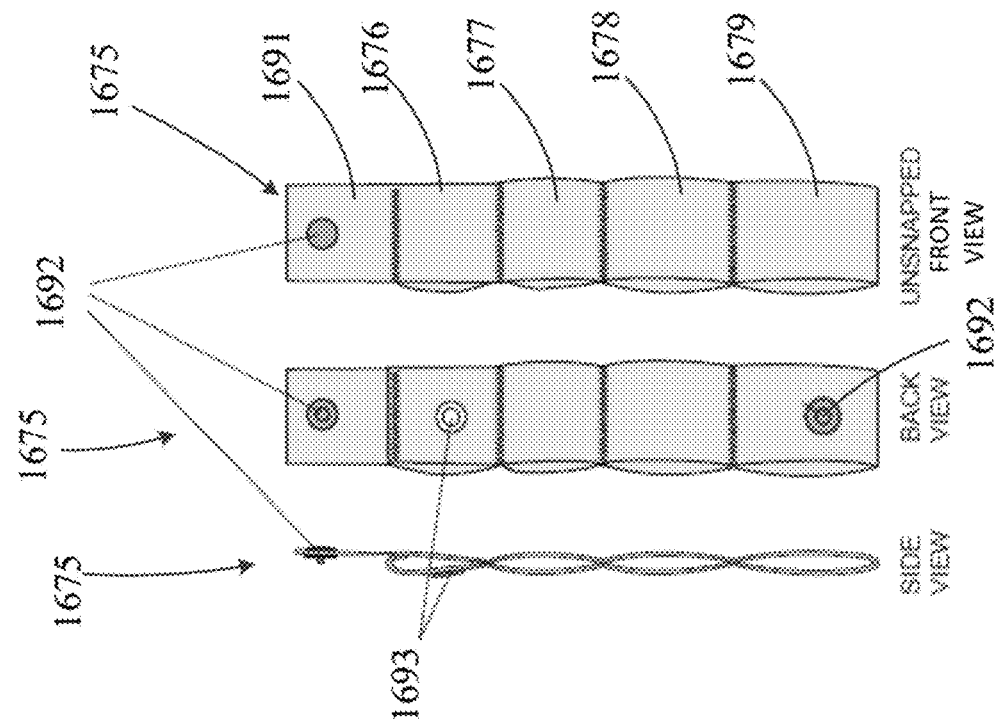
FIGS. 40A-40C illustrate a side view, a back view and a front view, respectively, of the extender of the garment of FIG. 36.

More specifically, as with previous embodiments, and as shown in FIGS. 39A-39B and 40A-40B, the extenders 1675 can include multiple loops that can provide for selective adjustment of the releasable attachment of the outer panel 1660 to the shoulder strap 1606 and the support strap 1680. In this embodiment, the extenders 1675 include four loops, 1676, 1677, 1678 and 1679. As described above, in this embodiment, the extenders 1675 can be removably coupled to the engagement mechanism 1650. More specifically, as shown in FIGS. 40A-40C, the extenders 1675 also include a tab portion 1691 that has a first coupler 1692 disposed on a back side of the tab portion 1691 that can matingly couple with a second coupler 1693 disposed on the back side of the first loop 1676. The tab portion 1691 can be inserted or looped through an opening 1668, around a securement bar 1684 and through an opening 1667 (see FIG. 39A) in the second portion 1654 of the engagement mechanism and the coupler 1692 can then be coupled to the coupler 1693 to removably couple the extender 1675 to the second portion 1654. The openings 1667 and 1668 and securement bar 1684 can be the same as openings 867 and 868 and securement bar 884, respectively, described above for engagement mechanism 850. The couplers 1692 and 1693 can be, for example, snap connectors (e.g., a male and female snap connectors), a hook and loop coupling, VELCRO, buttons, etc. To further secure extender 1675 to the support strap 1680 and maintain its position, a first coupler 1692 can be attached to the backside of the extender 1675 that can be releasably coupled to a mating coupler 1693 disposed on the front side of the support strap 1680, as shown in FIGS. 39C and 40B. For example, the coupler 1692 can be disposed on the backside of loop 1679 such that the extender 1675 is releasably attachable at a top portion to the first portion 1652 of the engagement mechanism 1650 and can be releasably attached at a bottom portion to the support strap 1680.

The loops 1676, 1677, 1678, 1679 can be formed from one or more pieces of material or fabric as described above for extenders 1175. It should be understood that an extender 1675 can include more or less loops, such as, for example, two, three, five, six, seven, eight, nine, ten, etc. Thus, the extender 1675 can have various lengths depending on the number of loops included. In some embodiments, the extenders 1675 can be formed with, for example, an elastic material or fabric to accommodate additional adjustment of the outer panel 1660 (e.g., the cup size) through the stretchability of the extender 1675. In other words, the overall length of the extender 1675 can be increased. In some embodiments, the extenders 1675 can be formed with a non-stretchable material or fabric, in which case the length of the extender would not vary during use.

With the extender 1675 coupled to the second portion 1654 of the engagement mechanism 1650 and the outer panel coupled to the first portion 1652, the outer panel 1660 can be releasably coupled to a select loop 1676, 1677, 1678, 1679 of the extender 1675 to achieve a cup size for outer panel 1660. The extender 1675 and outer panel 1660 can thus be releasably coupled to the shoulder strap 1606 and support strap 1680 when the second portion 1654 of the engagement mechanism 1650 is coupled to the first portion 1652.

In use, the garment 1600 can be worn by a wearer and if access to a breast of the wearer is desired, such as for breast pumping, the inner panel 1670 can be used and the outer panel 1660 (e.g., the right outer panel 1662 and/or the left outer panel 1664) can be detached from the inner panel 1670 (e.g., the right inner panel 1612 and/or the left inner panel 1614) in the same manner as described above for garment 1400. As described above, the first portion 1615 and the second portion 1617 of the inner panel 1670 (e.g., of the right inner panel 1612 and/or the left inner panel 1614) can be separated (e.g., stretched or folded) to create an opening 1630 through which the wearer's breast is accessible and a portion of a breast pump can be inserted. As described above, the center strap 1643 can be selectively coupled to the inner panel 1670 to provide additional support for the breast pump. The inner panel 1670 can thus support the breast pump during milk extraction. If further access to the breast of the wearer is desired, the inner panel 1670 can be detached from the shoulder straps 1606 and support straps 1680 in the same manner as described above for garment 1400. The inner panel 1670 and the outer panel 1660 can be reattached to shoulder strap 1606 and support strap 1680 in the same manner as described above for garment 1400.

As described above, the garment 1600 can also be used with the inner pumping panel 1670 completely removed from the garment 1600. In such a use, if desired, the outer panel 1660 can be detached from the shoulder straps 1606 and folded or moved downward to expose and gain access to one or both breast. In addition, if a user desires to increase the size of the cups of the outer panel 1660, to for example, wear a wearable breast pump, the user can add the extenders 1675 as described above. As described above, the center strap 1643 can be selectively coupled to the outer panel 1660 to provide additional support.

While various embodiments have been described above, it should be understood that they have been presented by way of example only, and not limitation. Where methods described above indicate certain events occurring in certain order, the ordering of certain events may be modified. Additionally, certain of the events may be performed concurrently in a parallel process when possible, as well as performed sequentially as described above.

Where embodiments described above indicate certain components arranged in certain orientations or positions, the arrangement of components may be modified. While the embodiments have been particularly shown and described, it will be understood that various changes in form and details may be made. Any portion of the apparatus and/or methods described herein may be combined in any combination and/or sub-combination, except mutually exclusive combinations. The embodiments described herein can include various combinations and/or sub-combinations of the functions, components and/or features of the different embodiments described.

What is claimed is:

1. A garment, comprising:
   a clasp having a first portion, a second portion, and a third portion, the first portion of the clasp being releasably couplable to and decouplable from each of the second portion of the clasp and the third portion of the clasp;
   a support strap coupled to the first portion of the clasp;
   an inner panel configured to cover a portion of a first breast of a wearer, the inner panel fully defining an opening, the inner panel configured to support at least a portion of a breast pump inserted at least partially through the opening, the inner panel coupled to the second portion of the clasp; and
   an outer panel coupled to the third portion of the clasp, the outer panel removably couplable to the inner panel via coupling the third portion of the clasp to the second portion of the clasp, the outer panel removably couplable to the support strap via coupling the third portion of the clasp to the first portion of the clasp.

2. The garment of claim 1, wherein at least a portion of the inner panel is fixedly coupled to the outer panel.

3. The garment claim 1, further comprising:
   a neck strap removably couplable to the inner panel.

4. The garment of claim 1, wherein the inner panel is fixedly coupled to the second portion of the clasp.

5. The garment of claim 1, wherein the inner panel is removably couplable to the second portion of the clasp.

6. The garment of claim 1, further comprising:
   a shoulder strap coupled to the first portion of the clasp.

7. The garment of claim 1, further comprising:
   an extender removably couplable to the clasp and including multiple coupling portions, the outer panel configured to be selectively coupled to one of the multiple coupling portions to adjust a position of the outer panel.

8. The garment of claim 1, further comprising:
   an extender fixedly coupled to the clasp and including multiple coupling portions, the outer panel configured to be selectively coupled to one of the multiple coupling portions to adjust a position of the outer panel.

9. A garment, comprising:
   a clasp having a first portion and a second portion;
   a support strap coupled to the first portion of the clasp, the support strap configured to be releasably coupled to an inner panel via coupling the first portion of the clasp to the clasp portion of the inner panel such that the first portion of the clasp can support the inner panel relative to a breast of a wearer when the first portion of the clasp is coupled to the clasp portion of the inner panel and the inner panel is supporting at least a portion of a breast pump inserted at least partially through an opening fully defined by the inner panel; and
   an outer panel coupled to the second portion of the clasp, the outer panel configured to cover a portion of a breast of a wearer, the outer panel configured to be releasably coupled to the inner panel via coupling the second portion of the clasp to a clasp portion of the inner panel.

10. The garment of claim 9, further comprising:
    a shoulder strap coupled to the first portion of the clasp.

11. The garment of claim 9, further comprising:
    an extender removably couplable to the clasp and including multiple coupling portions, the outer panel configured to be selectively coupled to one of the multiple coupling portions to adjust a position of the outer panel.

12. The garment of claim 9, further comprising:
    an extender fixedly coupled to the clasp and including multiple coupling portions, the outer panel configured to be selectively coupled to one of the multiple coupling portions to adjust a position of the outer panel.

13. The garment of claim 9, wherein the outer panel includes a first coupling member disposed on a back side of the outer panel, the first coupling member configured to releasably engage with a second coupling member disposed on a front side of the inner panel.

14. The garment of claim 9, wherein the support strap includes a first coupling member disposed on a front side of the support strap, the first coupling member configured to releasably engage with a second coupling member disposed on a back side of the inner panel.

15. A garment, comprising:
   a clasp having a first portion, a second portion, and a third portion, the first portion of the clasp being releasably couplable to and decouplable from each of the second portion of the clasp and the third portion of the clasp, the second portion of the clasp configured to be releasably coupled to an inner panel;
   a support strap coupled to the first portion of the clasp, the support strap configured to be releasably coupled to the inner panel via coupling the second portion of the clasp to the inner panel and coupling the first portion of the clasp to the second portion of the clasp such that the first portion of the clasp can support the second portion of the clasp and the inner panel relative to a breast of a wearer when the inner panel is supporting at least a portion of a breast pump inserted at least partially through an opening fully defined by the inner panel; and
   an outer panel coupled to the third portion of the clasp, the outer panel configured to be releasably coupled to the inner panel via coupling the second portion of the clasp to the inner panel and coupling the third portion of the clasp to the second portion of the clasp.

16. The garment of claim 15, further comprising:
   a shoulder strap coupled to the first portion of the clasp.

17. The garment of claim 15, further comprising:
   an extender removably couplable to the clasp and including multiple coupling portions, the outer panel configured to be selectively coupled to one of the multiple coupling portions to adjust a position of the outer panel.

18. The garment of claim 15, further comprising:
   an extender fixedly coupled to the clasp and including multiple coupling portions, the outer panel configured to be selectively coupled to one of the multiple coupling portions to adjust a position of the outer panel.

19. The garment of claim 15, wherein the outer panel includes a first coupling member disposed on a back side of the outer panel, the first coupling member configured to releasably engage with a second coupling member disposed on a front side of the inner panel.

20. The garment of claim 15, wherein the support strap includes a first coupling member disposed on a front side of the support strap, the first coupling member configured to releasably engage with a second coupling member disposed on a back side of the inner panel.

* * * * *